(12) United States Patent
Steffan et al.

(10) Patent No.: US 7,585,871 B2
(45) Date of Patent: Sep. 8, 2009

(54) PHENANTHRIDINE CARBONYL PHENOLS

(75) Inventors: Robert John Steffan, Langhorne, PA (US); William Jay Moore, Collegeville, PA (US); Eugene J. Trybulski, Huntingdon Valley, PA (US); Albert John Molinari, Pottstown, PA (US)

(73) Assignee: Wyeth, Madison, NJ (US)

( * ) Notice: Subject to any disclaimer, the term of this patent is extended or adjusted under 35 U.S.C. 154(b) by 600 days.

(21) Appl. No.: 11/215,333

(22) Filed: Aug. 30, 2005

(65) Prior Publication Data

US 2006/0058337 A1 Mar. 16, 2006

Related U.S. Application Data

(60) Provisional application No. 60/606,784, filed on Sep. 2, 2004.

(51) Int. Cl.
*C07D 221/12* (2006.01)
*A61K 31/435* (2006.01)
(52) U.S. Cl. .................................. 514/290; 546/79
(58) Field of Classification Search ................. None
See application file for complete search history.

(56) References Cited

U.S. PATENT DOCUMENTS

| 4,206,225 | A | 6/1980 | Johnson | 514/232.8 |
| 4,228,169 | A | 10/1980 | Johnson et al. | 514/298 |
| 5,869,483 | A | 2/1999 | Albright et al. | 514/217 |
| 6,894,061 | B2 | 5/2005 | Molinari et al. | 514/298 |

FOREIGN PATENT DOCUMENTS

| EP | 0 009 386 A1 | 4/1980 |
| WO | 02/05616 A1 | 1/2002 |
| WO | 03/050095 A1 | 6/2003 |
| WO | 2004/031159 A1 | 4/2004 |
| WO | 2004/050631 A1 | 6/2004 |

OTHER PUBLICATIONS

Adams, M. R. et al., "Inhibition of Coronary Artery Atherosclerosis by 17-beta Estradiol in Ovariectomized Monkeys," *Arterio.*, 1990, 10(6),1051-1057.
Alexander et. al., "Initiation of Hormone Replacement Therapy After Acute Myocardial Infarction Is Associated With More Cardiac Events During Follow-Up," *J. Am. Coll. Cardio.*, 2001, 38, 1-7.
Bauer M. A., Herrmann F., "Interleukin-6 in clinical medicine," *Ann. Hematol.*, 1991, 62, 203-210.
Cefalu, W., "The Use of Hormone Replacement Therapy in Postmenopausal Women with Type 2 Diabetes," *J Womens Health & Gender-based Med.*, 2001, 10(3), 241-255.
Chandrasekar, B. et al. "Ischemia-Reperfusion of Rat Myocardium Activates Nuclear Factor- κB and Induces Neutrophil Infiltration Via Lipopolysaccharide-Induced CXC Chemokine," *Circulation*, 2001 103, 2296-2302.

Curtin, D. Y. et al., "Intramolecular Oxygen-Nitrogen Benzoyl Migration of 6-Aroyloxyphenanthridines," *J. Org. Chem.*, 1972, 37(22), 3439-3443.
Cuzzocrea, S. et al., "17β-Estradiol Antiinflammatory Activity in Carrageenan-Induced Pleurisy," *Endocrinology*, 2000, 141, 1455-1463.
Delyani, J. A. et al., "Protection from Myocardial Reperfusion Injury by Acute Administration of 17 β-Estradiol," *J. Molec. Cell. Cardiol.*, 1996, 28, 1001-1008.
Dietrich, H. et al., "Mouse Model of Transplant Arteriosclerosis," *Arterioscler. Thromb. Vasc. Biol.*, 2000, 20, 343-352.
Dubal, D. B. et al., "Estradiol Modulates bcl-2 in Cerebral Ischemia: A Potential Role for Estrogen Receptors," *J. Neurosci.*, 1999, 19, 6385-6393.
Dubal, D. B. et al., "Estrogen receptor α, not β, is a critical link in estradiol-mediated protection against brain injury," *PNAS, USA*, 2001, 98, 1952-1957.
Felson, D. T. et al., "The effects of estrogen on osteoarthritis," *Curr Opinion Rheum*, 1998, 10, 269-272.
Grodstein F. et. al., "Postmenopausal Hormone Use and Secondary Prevention of Coronary Events in the Nurses' Health Study," *Ann. Int. Med*, 2001, 135, 1-8.
Grodstein, F. et. al., "A Prospective, Observational Study of Postmenopausal Hormone Therapy and Primary Prevention of Cardiovascular Disease," *Ann. Int. Med.*, 2000, 133, 933-41.
Hulley, S. et. al., "Randomized Trial of Estrogen Plus Progestin for Secondary Prevention of Coronary Heart Disease in Postmenopausal Women," *J. Am. Med. Assoc.*, 1998, 280, 605-13.
Izumi, T. et al., "Blockade of the natriuretic peptide receptor guanylyl cyclase-A inhibits NF-κB activation and alleviates myocardial ischemia/reperfusion injury," *J. Clin. Invest.*, 2001, 108, 203-213.

(Continued)

*Primary Examiner*—Rita J Desai
(74) *Attorney, Agent, or Firm*—Pepper Hamilton LLP

(57) ABSTRACT

The present invention relates generally to phenanthridine carbonyl compositions such as substituted phenanthridine carbonyl phenols of Formula 1:

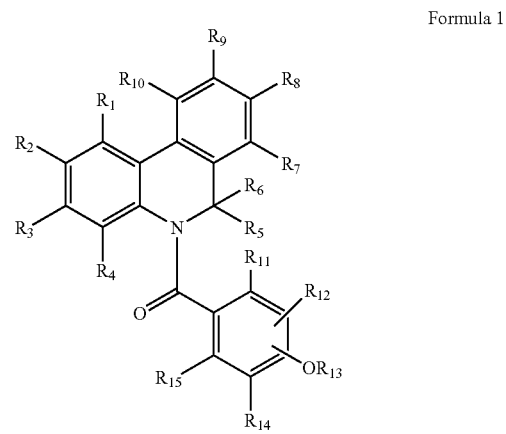

Formula 1 wherein $R_1$ to $R_{15}$ are as defined in the specification, or pharmaceutically acceptable salts thereof; and methods of using them.

27 Claims, No Drawings

OTHER PUBLICATIONS

Kadokami, T. et al., "Anti-Tumor Necrosis Factor-α Antibody Limits Heart Failure in a Transgenic Model," *Circulation*, 2001, 104, 1094-1097.

Karas, R. H. et al., "Effects of Estrogen on the Vascular Injury Response in Estrogen Receptor α,β (Double) Knockout Mice," *Circ. Res.*, 2001, 89, 534-539.

Kurebayashi S. et al., "Characterization of Mechanisms of Interleukin-6 Gene Repression by Estrogen Receptor," *J. Steroid Biochem. Molec. Biol.*, 1997, 60, 11-17.

Lin, C. C. et al., "Pulmonary function changes and increased Th-2 cytokine expression and nuclear factor κB activation in the lung after sensitization and allergen challenge in brown Norway rats," *Immunol. Lett.*, 2000, 73, 57-64.

Lou, H. et al., "Inhibition of Transplant Coronary Arteriosclerosis in Rabbits by Chronic Estradiol Treatment Is Associated With Albolition of MHC Class II Antigen Expression," *Circulation*, 1996, 94, 3355-3361.

Lundeen, S. G. et al., "Rat uterine complement C3 expression as a model for progesterone receptor modulators: characterization of the new progestin trimegestone," *J. Steroid Biochem Biol.*, 2001, 78, 137-143.

Lysén, M. et al., "Convergent Synthesis of 6-Substituted Phenanthridines via Anionic Ring Closure," *Organic Letters*, 2002, 4(2), 257-259.

Merchenthaler, I. et al., "The effect of estrogens and antiestrogens in a rat model for hot flush," *Maturitas*, 1998, 30, 307-316.

Nathan, L. et al., "Estradiol Inhibits Leukocyte Adhesion and Transendothelial Migration in Rabbits In Vivo," *Circ. Res.*, 1999, 85, 377-385.

Patra, P. K. et al., "A New Regiospecific Method for the Synthesis of Substituted Phenanthridines and Benzo[j]phenanthridines via Aromatic Annelation of 1-N-Benzenesulfonyl-3-[Bis(methylthio)methylene]-1,2,3,4-tetrahydroquinoline-4-one," *Tetrahedron*, 1998, 54, 10167-10178.

Pelletier et al., "Osteoarthritis, an Inflammatory Disease," *Arthr. & Rheum.*, 2001, 44:1237-1247.

Popp, F. D., et al. "Reissert Compound Studies. Part V. Nature of the Acid Chloride," *J. Chem. Soc.*, 1963, 1760-1763.

Prokai, L. et al., "Synthesis and Biological Evaluation of 17β-Alkoxyestra-1,3,5(10)-trienes as Potential Neuroprotectants Against Oxidative Stress," *J. Med. Chem.*, 2001, 44, 110-114.

Reis et. al., "Estrogen Is Associated With Improved Survival in Aging Women With Congestive Heart Failure: Analysis of the Vesnarinone Studies," *J. Am. Coll. Cardio.*, 2000, 36, 529-33.

Roth, A. et. al., "Phytoestrogen Kaempferol (3,4',5,7-Tetrahydroxylflavone) Protects PC12 and T47D Cells From β-Amyloid-Induced Toxicity," *J. Neurosci. Res.*, 1999, 57, 399-404.

Schonknecht, P. et. al., "Reduced cerebrospinal fluid estradiol levels are associated with increased β-amyloid levels in female patients with Alzheimer's disease," *Neurosci. Lett.*, 2001, 307, 122-124.

Shughrue, P. J. et al., "Regulation of Progesterone Receptor Messenger Ribonucleic Acid in the Rat Medial Preoptic Nucleus by Estrogenic and Antiestrogenic Compounds: An in Situ Hybridization Study," *Endocrinology*, 1997, 138, 5476-5484.

Stetson, S. J. et al., "Cardiac Hypertrophy After Transplantation Is Associated With Persistent Expression of Tumor Necrosis Factor-α," *Circulation*, 2001, 104, 676-681.

Sullivan, T. R. et al. "Estrogen Inhibits the Response-to-Injury in a Mouse Carotid Artery Model," *J. Clin. Invst.*, 1995, 96, 2482-8.

Wallen, W. J. et al., "Gender-Differences in Myocardial Adaptation to Afterload in Normotensive and Hypertensive Rats," *Hypertension*, 2000, 36, 774-779.

Yagi, K., "Short Communications. A Simple Fluorometric Assay for Lipoperoxide in Blood Plasma," *Biochemical Medicine*, 1976, 15, 212-216.

Yokoseki, O. et al., "*cis* Element Decoy Against Nuclear Factor-κB Attenuates Development of Experimental Autoimmune Myocarditis in Rats," *Circ. Res.*, 2001, 89, 899-906.

Yuan et al., "Reversal of Obesity- and Diet-Induced Insulin Resistance with Salicylates or Targeted Disruption of *Ikkβ*," *Science*, 2001, 293, 1673-1677.

Zaulyanov, L. L. et al., "Glutamate Receptor Requirement for Neuronal Death from Anoxia-Reoxygenation: An in Vitro Model for Assessment of the Neuroprotective Effects of Estrogens," *Cellular & Molecular Neurobiology*, 1999, 19, 705-718.

PHENANTHRIDINE CARBONYL PHENOLS

CROSS-REFERENCE TO RELATED APPLICATIONS

This application claims priority to provisional application Ser. No. 60/606,784 filed on Sep. 2, 2004 incorporated herein by reference in its entirety.

BACKGROUND

The present invention relates generally to phenanthridine carbonyl compounds such as substituted phenanthridine carbonyl phenols and methods of using them.

The ability of ligands for the estrogen receptor to inhibit inflammatory gene expression and cause a reduction of cytokines, chemokines, adhesion molecules and inflammatory enzymes is well known. A common component of chronic inflammatory conditions is polymorphonuclear leukocyte and monocyte infiltration into the site of damage through increased expression of cytokines and adhesion molecules responsible for their recruitment. Overproduction of the cytokine interleukin (IL-6) has been associated with states of chronic inflammation (Bauer M. A., Herrmann F., *Ann. Hematol.*, 1991, 62, 203). Synthesis of the IL-6 gene is believed to be induced by the transcription factor nuclear factor κB (NF-κB). Interference at this step in the inflammatory process can effectively regulate the uncontrolled proliferative process that occurs in these chronic conditions.

Activation of the estrogen receptor provides a means to treat the inflammatory component of diseases such as atherosclerosis, myocardial infarction (MI), congestive heart failure (CHF), inflammatory bowel disease and arthritis, in part by interfering with cytokine expression. Other therapeutic indications for these type of molecules include type II diabetes (Cefalu, *J Womens Health & Gender-based Med.* 2001, 10, 241; Yuan et al., *Science*, 2001, 293, 1673), osteoarthritis (Pelletier et al., *Arthr. & Rheum.*, 2001, 44:1237; Felson et al., *Curr Opinion Rheum*, 1998, 10, 269) asthma (Chin-Chi Lin et. al., *Immunol. Lett.*, 2000, 73, 57), Alzheiemer's disease (Roth, A. et. al.,; *J. Neurosci. Res.*, 1999, 57, 399) and autoimmune diseases such as multiple sclerosis and rheumatoid arthritis.

In view of the foregoing, there exists a need for the identification of ligands for the estrogen receptor and for methods of using the identified ligands to modulate the activity of the receptor and, preferably, treat disease.

SUMMARY

The present invention provides, inter alia, phenanthridine carbonyl compounds and compositions, particularly those that find use as ligands for the estrogen receptor, and methods of using them. Representative compounds of the invention include those of Formula 1:

Formula 1

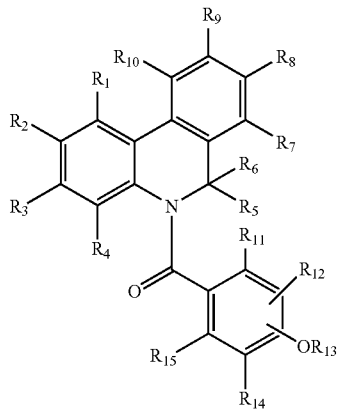

wherein $R_1$, $R_2$, $R_3$, and $R_4$, are, independently, hydrogen, lower alkyl, halogen, or aryl;

$R_7$, $R_8$, $R_9$, and $R_{10}$, are, independently, hydrogen, lower alkyl or halogen;

$R_{11}$, $R_{12}$, $R_{14}$, and $R_{15}$ are, independently, hydrogen, hydroxy, lower alkyl, alkoxy, or halogen;

one of $R_5$ and $R_6$ is hydrogen and the other is lower alkyl;

$R_{13}$ is hydrogen, —(C=O)$R_{16}$, —S(O)$_2R_{17}$, —S(O)$_2$N($R_{18}$)($R_{19}$), or D-glucuronidate;

$R_{16}$ is alkyl, aralkyl or aryl;

$R_{17}$ is alkyl, aryl, heteroaryl, cycloalkyl, alkenyl, cycloalkenyl, or alkynyl;

$R_{18}$ and $R_{19}$ are, independently, hydrogen, alkyl, alkenyl, alkynyl, cycloalkyl, monofluoroalkyl, perfluoroalkyl, aryl, arylalkyl, cycloalkenyl, heteroaryl, heteroarylalkyl, hydroxy-($C_2$-$C_6$)alkyl, alkoxyalkyl, alkylthioalkyl, carbonyl, acyl, alkoxycarbonyl, —C(O)NH$_2$, alkylaminocarbonyl, dialkylaminocarbonyl, alkylaminoalkyl, or dialkylaminoalkyl;

or $R_{18}$ and $R_{19}$ are taken together with the nitrogen atom to which they are attached to form a saturated, unsaturated or partially saturated $C_4$-$C_6$ carbon ring.

In some compounds of the present invention, $R_1$, $R_2$, $R_3$, $R_4$, $R_7$, $R_8$, $R_9$, and $R_{10}$, are, independently, hydrogen, lower alkyl or halogen;

$R_{11}$, $R_{12}$, $R_{14}$, and $R_{15}$ are, independently, hydrogen, hydroxy, lower alkyl, alkoxy, or halogen;

one of $R_5$ and $R_6$ is hydrogen and the other is lower alkyl;

$R_{13}$ is hydrogen, —(C=O)$R_{16}$, —S(O)$_2R_{17}$, —S(O)$_2$N($R_{18}$)($R_{19}$), or D-glucuronidate;

$R_{16}$ is alkyl, aralkyl or aryl;

$R_{17}$ is alkyl, aryl, heteroaryl, cycloalkyl, alkenyl, cycloalkenyl, or alkynyl;

$R_{18}$ and $R_{19}$ are, independently, hydrogen, alkyl, alkenyl, alkynyl, cycloalkyl, monofluoroalkyl, perfluoroalkyl, aryl, arylalkyl, cycloalkenyl, heteroaryl, heteroarylalkyl, hydroxy-($C_2$-$C_6$)alkyl, alkoxyalkyl, alkylthioalkyl, carbonyl, acyl, alkoxycarbonyl, —C(O)NH$_2$, alkylaminocarbonyl, dialkylaminocarbonyl, alkylaminoalkyl, or dialkylaminoalkyl or $R_{18}$ and $R_{19}$ are taken together with the nitrogen atom to which they are attached to form a saturated, unsaturated or partially saturated $C_4$-$C_6$ carbon ring.

The present invention also provides, inter alia, prodrugs, enantiomers, hydrates, solvates, or pharmaceutically acceptable salts or esters of Formula 1.

Methods of using the compounds of the present ivnention are also provided. For example, exemplary compounds can be used to modulate cytokine expression in a cell. In some embodiments, an effective amount of one or more compounds of the present invention can be provided to a subject to inhibit cytokine expression in the subject. In one aspect, the cytokine is interleukin, e.g, IL-6. In some embodiments, the subject suffers from chronic inflammatory disease. In some embodiments, the subject suffers from atherosclerosis, myocardial infarction, congestive heart failure, inflammatory bowel disease, or arthritis.

The present invention also provides, inter alia, methods of treating a condition or disease characterized by increased cytokine expression or activity. Such methods comprise providing to a subject a pharmaceutically effective amount of a compound of the present invention. In one aspect, the disease is a chronic inflammatory disease. In some embodiments, the compound is useful in treating the inflammatory component of a disease such as atherosclerosis, myocardial infarction, congestive heart failure, inflammatory bowel disease, or arthritis.

The present invention also provides, inter alia, methods of determining the activity of a compound of the present invention. The method can include the step of contacting a compound of the present invention with a cell and measuring cytokine expression in the cell, e.g., by Western or Northern Blot. In some embodiments, the cell will be one that overexpresses cytokines. The step of measuring cytokine expression in the cell can occur before or after the contacting step. In one aspect, the cytokine is interleukin, e.g., IL-6.

The present invention also provides, inter alia, kits for inhibiting cytokine expression and/or for treating chronic inflammatory disease in a subject comprising a container, a pharmaceutical composition contained therein comprising a compound of the present invention, and a package insert indicating that the pharmaceutical composition can be used for the inhibition of cytokine expression and/or for the treatment of chronic inflammatory disease.

DETAILED DESCRIPTION

The present invention provides substituted phenanthridine carbonyl phenols and substituted phenanthridine carbonyl phenol derivatives, processes for preparing such compounds, pharmaceutical compositions comprising such compounds, and methods for using such compounds. Preferred compounds have properties that are useful for the treatment, including the prevention and inhibition, of a wide variety of diseases and disorders affected by the estrogen receptor.

Compounds of the present invention include those of Formula 1:

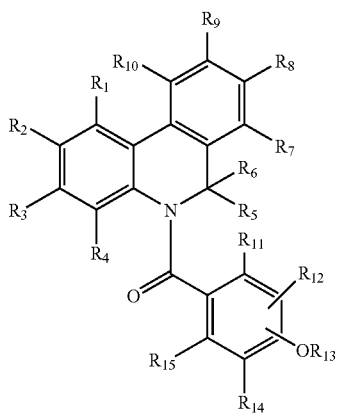

Formula 1 wherein
$R_1$, $R_2$, $R_3$, and $R_4$, are, independently, hydrogen, lower alkyl, halogen, or aryl;
$R_7$, $R_8$, $R_9$, and $R_{10}$, are, independently, hydrogen, lower alkyl or halogen;
$R_{11}$, $R_{12}$, $R_{14}$, and $R_{15}$ are, independently, hydrogen, hydroxy, lower alkyl, alkoxy, or halogen;
one of $R_5$ and $R_6$ is hydrogen and the other is lower alkyl;
$R_{13}$ is hydrogen, —(C═O)$R_{16}$, —S(O)$_2$$R_{17}$, —S(O)$_2$N($R_{18}$)($R_{19}$), or D-glucuronidate;
$R_{16}$ is alkyl, aralkyl or aryl;
$R_{17}$ is alkyl, aryl, heteroaryl, cycloalkyl, alkenyl, cycloalkenyl, or alkynyl;

$R_{18}$ and $R_{19}$ are, independently, hydrogen, alkyl, alkenyl, alkynyl, cycloalkyl, monofluoroalkyl, perfluoroalkyl, aryl, arylalkyl, cycloalkenyl, heteroaryl, heteroarylalkyl, hydroxy-($C_2$-$C_6$)alkyl, alkoxyalkyl, alkylthioalkyl, carbonyl, acyl, alkoxycarbonyl, —C(O)NH$_2$, alkylaminocarbonyl, dialkylaminocarbonyl, alkylaminoalkyl, or dialkylaminoalkyl;
or $R_{18}$ and $R_{19}$ are taken together with the nitrogen atom to which they are attached to form a saturated, unsaturated or partially saturated $C_4$-$C_6$ carbon ring.

In some compounds of the present invention,
$R_1$, $R_2$, $R_3$, $R_4$, $R_7$, $R_8$, $R_9$, and $R_{10}$, are, independently, hydrogen, lower alkyl or halogen;
$R_{11}$, $R_{12}$, $R_{14}$, and $R_{15}$ are, independently, hydrogen, hydroxy, lower alkyl, alkoxy, or halogen;
one of $R_5$ and $R_6$ is hydrogen and the other is lower alkyl;
$R_{13}$ is hydrogen, —(C═O)$R_{16}$, —S(O)$_2$$R_{17}$, —S(O)$_2$N($R_{18}$)($R_{19}$), or D-glucuronidate;
$R_{16}$ is alkyl, aralkyl or aryl;
$R_{17}$ is alkyl, aryl, heteroaryl, cycloalkyl, alkenyl, cycloalkenyl, or alkynyl;
$R_{18}$ and $R_{19}$ are, independently, hydrogen, alkyl, alkenyl, alkynyl, cycloalkyl, monofluoroalkyl, perfluoroalkyl, aryl, arylalkyl, cycloalkenyl, heteroaryl, heteroarylalkyl, hydroxy-($C_2$-$C_6$)alkyl, alkoxyalkyl, alkylthioalkyl, carbonyl, acyl, alkoxycarbonyl, —C(O)NH$_2$, alkylaminocarbonyl, dialkylaminocarbonyl, alkylaminoalkyl, or dialkylaminoalkyl
or $R_{18}$ and $R_{19}$ are taken together with the nitrogen atom to which they are attached to form a saturated, unsaturated or partially saturated $C_4$-$C_6$ carbon ring.

In some compounds of the present invention
$R_1$, $R_2$, $R_3$, and $R_4$, are, independently, hydrogen, $C_{1-6}$ alkyl, halogen, or $C_{6-14}$ aryl;
$R_7$, $R_8$, $R_9$, and $R_{10}$, are, independently, hydrogen, $C_{1-6}$ alkyl or halogen;
$R_{11}$, $R_{12}$, $R_{14}$, and $R_{15}$ are, independently, hydrogen, hydroxy, $C_{1-6}$ alkyl, $C_{1-6}$ alkoxy, or halogen;
one of $R_5$ and $R_6$ is hydrogen and the other is $C_{1-6}$ alkyl;
$R_{13}$ is hydrogen, —(C═O)$R_{16}$, —S(O)$_2$$R_{17}$, —S(O)$_2$N($R_{18}$)($R_{19}$), or D-glucuronidate;
$R_{16}$ is $C_{1-6}$ alkyl, $C_{6-14}$ ar($C_{1-6}$)alkyl or $C_{6-14}$ aryl;
$R_{17}$ is $C_{1-6}$ alkyl, $C_{6-14}$ aryl, heteroaryl, $C_{1-6}$ cycloalkyl, $C_{2-15}$ alkenyl, $C_{4-15}$ cycloalkenyl, or $C_{2-15}$ alkynyl,
$R_{18}$ and $R_{19}$ are, independently, hydrogen, $C_{1-6}$ alkyl, $C_{2-15}$ alkenyl, $C_{2-15}$ alkynyl, $C_{3-15}$ cycloalkyl, monofluoro($C_{1-10}$)alkyl, perfluoro($C_{1-6}$)alkyl, $C_{6-14}$ aryl, $C_{6-14}$aryl($C_{1-6}$)alkyl, $C_{2-15}$ cycloalkenyl, heteroaryl, heteroaryl($C_{1-6}$)alkyl, hydroxy-($C_2$-$C_6$)alkyl, $C_{1-6}$ alkoxy($C_{1-6}$)alkyl, $C_{1-6}$ alkylthio($C_{1-6}$)alkyl, carbonyl, acyl, $C_{1-6}$ alkoxycarbonyl, —C(O)NH$_2$, $C_{1-6}$ alkylaminocarbonyl, di($C_{1-6}$)alkylaminocarbonyl, $C_{1-6}$ alkylamino($C_{1-6}$) alkyl, or di($C_{1-6}$)alkylamino($C_{1-6}$)alkyl
or $R_{18}$ and $R_{19}$ are taken together with the nitrogen atom to which they are attached to form a saturated, unsaturated or partially saturated $C_4$-$C_6$ carbon ring.

Compounds of the present invention also include prodrugs, enantiomers, diastereomers, racemates, geometric isomers, hydrates, solvates, or pharmaceutically acceptable salts or esters of Formula 1.

Exemplary compounds of Formula 1 include those wherein at least one of $R_1$, $R_2$, $R_3$, $R_4$, $R_7$, $R_8$, $R_9$, and $R_{10}$, is halogen. For example, in one exemplary embodiment, $R_3$ or $R_8$ is halogen. In another exemplary embodiment, both $R_3$ and $R_8$ are halogen. In another exemplary embodiment, $R_3$ or $R_8$ is chlorine or fluorine or $R_3$ and $R_8$ are chlorine or fluorine.

Exemplary embodiments of compounds of Formula 1 include those wherein $R_1$, $R_2$, $R_3$, $R_4$, $R_7$, $R_8$, $R_9$, and $R_{10}$ are hydrogen or halogen.

Exemplary compounds of Formula 1 include those wherein $R_{12}$, $R_{14}$ and $R_{15}$ are hydrogen, halogen, hydroxy, or alkoxy. For example in some embodiments, $R_{12}$, $R_{14}$ and $R_{15}$ are hydrogen, chlorine, bromine, fluorine, hydroxy, or methoxy.

Exemplary compounds of Formula 1 include those wherein $R_{13}$ is hydrogen.

Exemplary embodiments of Formula 1 include those wherein at least one of $R_1$, $R_2$, $R_3$, $R_4$, $R_7$, $R_8$, $R_9$, and $R_{10}$, is halogen, $R_{12}$, $R_{14}$ and $R_{15}$ are hydrogen, chlorine, bromine, fluorine, hydroxy, or alkoxy (e.g., methoxy) and $R_{13}$ is hydrogen.

Further exemplary embodiments of Formula 1 include those wherein at least one of $R_1$, $R_2$, $R_3$, $R_4$, $R_7$, $R_8$, $R_9$, and $R_{10}$, is halogen and the others are hydrogen. Further embodiments include those where at least one of $R_{12}$, $R_{14}$ and $R_{15}$ is hydrogen, chlorine, bromine, fluorine, hydroxy, or alkoxy (e.g., methoxy) and the others are hydrogen. For both of these embodiments $R_{13}$ is preferably hydrogen.

Representative compounds of the present invention include compounds of formulas 2 to 12:

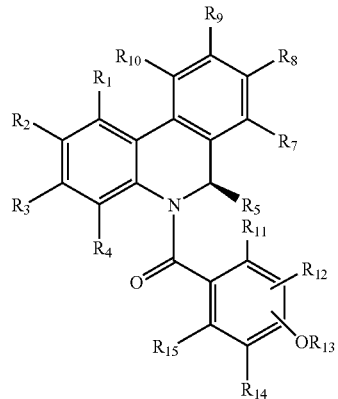

Formula 2

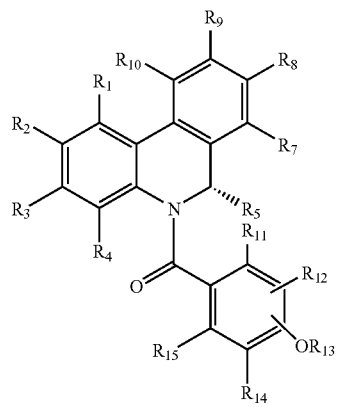

Formula 3

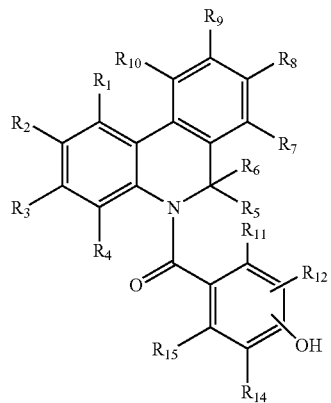

Formula 4

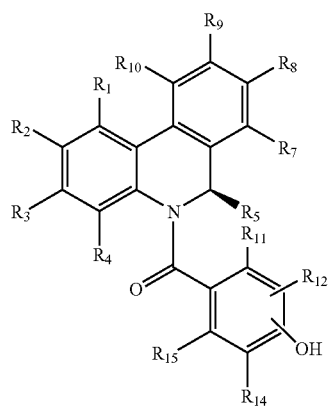

Formula 5

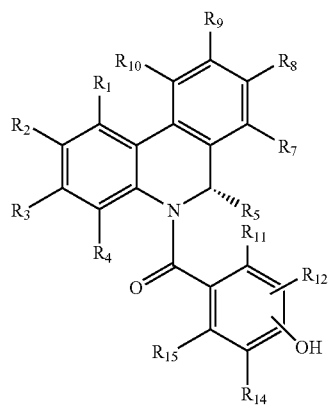

Formula 6

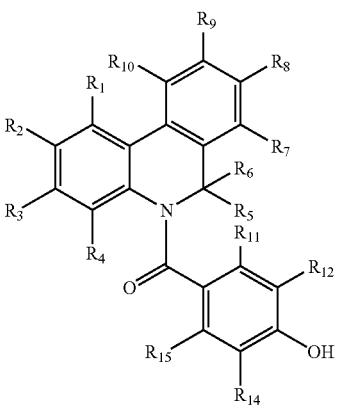

Formula 7

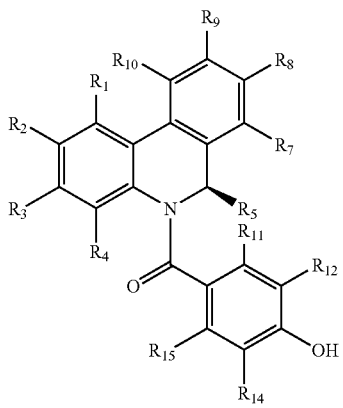

Formula 8

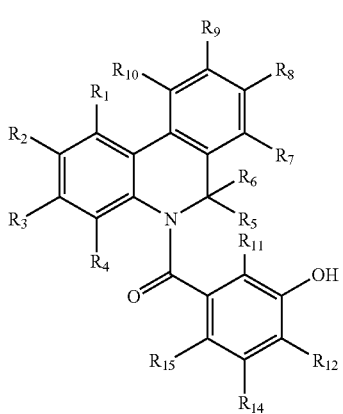

Formula 9

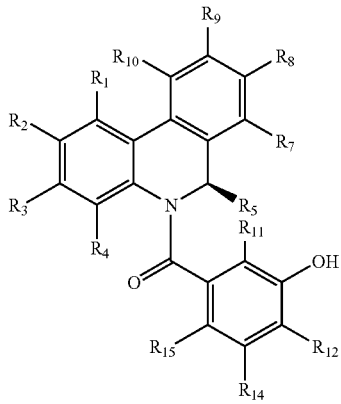

Formula 11

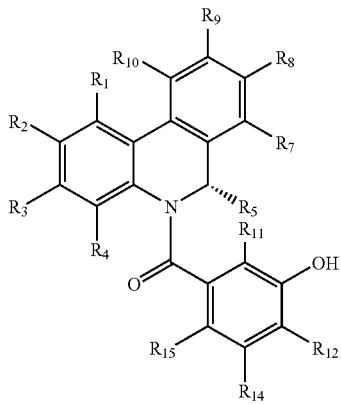

Formula 12

Formula 10 wherein $R_1$, $R_2$, $R_3$, $R_4$, $R_5$, $R_6$ $R_7$, $R_8$, $R_9$, $R_{10}$, $R_{11}$, $R_{12}$, $R_{14}$, and $R_{15}$ are as defined herein for Formula 1.

The present invention also provides, inter alia, prodrugs, enantiomers, diastereomers, racemates, geometric isomers, hydrates, solvates, or pharmaceutically acceptable salts or esters of compounds of Formulas 2 to 12.

Compounds of Formulas 2 to 12 include those wherein at least one of $R_1$, $R_2$, $R_3$, $R_4$, $R_7$, $R_8$, $R_9$, and $R_{10}$, is halogen. For example, in one exemplary embodiment, $R_3$ or $R_8$ is halogen. In another exemplary embodiment, both $R_3$ or $R_8$ are halogen. In another exemplary embodiment, $R_3$ or $R_8$ is chlorine or fluorine or $R_3$ and $R_8$ are chlorine or fluorine. Exemplary compounds of Formulas 2 to 12 include those wherein at $R_1$, $R_2$, $R_3$, $R_4$, $R_7$, $R_8$, $R_9$, and $R_{10}$ are hydrogen or halogen.

Exemplary compounds of Formulas 2 to 12 include those wherein $R_{12}$, $R_{14}$ and $R_{15}$ are hydrogen, halogen, hydroxy, or alkoxy. For example in some embodiments, $R_{12}$, $R_{14}$ and $R_{15}$ are hydrogen, chlorine, bromine, fluorine, hydroxy, or methoxy.

Exemplary embodiments of Formulas 2 to 12 include those wherein at least one of $R_1$, $R_2$, $R_3$, $R_4$, $R_7$, $R_8$, $R_9$, and $R_{10}$, is halogen and $R_{12}$, $R_{14}$ and $R_{15}$ are hydrogen, chlorine, bromine, fluorine, hydroxy, or methoxy.

Exemplary substituted 6-substituted-phenanthridin-5 (6H)-ylcarbonylphenyl derivatives of the present invention include, but are not limited to, 4-{[(6R)-8-fluoro-6-methylphenanthridin-5(6H)-yl]carbonyl}phenol; 3-{[(6S)-8-fluoro-6-methylphenanthridin-5(6H)-yl]carbonyl}phenol; 4-{[(6S)-8-fluoro-6-methylphenanthridin-5(6H)-yl]carbonyl}phenol; 3-{[(6R)-8-fluoro-6-methylphenanthridin-5(6H)-yl]carbonyl}phenol; 3-fluoro-4-{[(6R)-8-fluoro-6-methylphenanthridin-5(6H)-yl]carbonyl}phenol; 3-fluoro-4-{[(6S)-8-fluoro-6-methylphenanthridin-5(6H)-yl]carbonyl}phenol; 4-fluoro-3-{[(6R)-8-fluoro-6-methylphenanthridin-5(6H)-yl]carbonyl}phenol; 4-fluoro-3-{[(6S)-8-fluoro-6-methylphenanthridin-5(6H)-yl]carbonyl}phenol; 2-fluoro-4-{[(6R)-8-fluoro-6-methylphenanthridin-5(6H)-yl]carbonyl}phenol; 2-fluoro-4-{[(6S)-8-fluoro-6-methylphenanthridin-5(6H)-yl]carbonyl}phenol; 2-chloro-5-{[(6R)-8-fluoro-6-methylphenanthridin-5(6H)-yl]carbonyl}phenol; 2-chloro-5-{[(6S)-8-fluoro-6-methylphenanthridin-5(6H)-yl]carbonyl}phenol; 2-bromo-4-{[(6R)-8-fluoro-6-methylphenanthridin-5(6H)-yl]carbonyl}phenol; 2-bromo-4-{[(6S)-8-fluoro-6-methylphenanthridin-5(6H)-yl]carbonyl}phenol; 4-bromo-3-{[(6R)-8-fluoro-6-methylphenanthridin-5(6H)-yl]carbonyl}phenol; 4-bromo-3-{[(6S)-8-fluoro-6-methylphenanthridin-5(6H)-yl]carbonyl}phenol; 4-{[(6R)-8-fluoro-6-methylphenanthridin-5(6h)-yl]carbonyl}-2-methoxyphenol; 4-{[(6S)-8-fluoro-6-methylphenanthridin-5(6H)-yl]carbonyl}-2-methoxyphenol; 4-{[(6S)-6-ethyl-8-fluorophenanthridin-5(6H)-yl]carbonyl}phenol; 4-{[(6R)-6-ethyl-8-fluorophenanthridin-5(6H)-yl]carbonyl}phenol; 3-{[(6R)-6-ethyl-8-fluorophenanthridin-5(6H)-yl]carbonyl}phenol; 4-{[(6R)-6-ethyl-8-fluorophenanthridin-5(6H)-yl]carbonyl}benzene-1,3-diol; 4-[(6-ethyl-8-fluorophenanthridin-5(6H)-yl) carbonyl)-3-fluorophenol; 3-[(3-chloro-6-methylphenanthridin-5(6H)-yl)carbonyl]phenol; 3-{[(6R)-3-chloro-6-methylphenanthridin-5(6H)-yl]carbonyl}phenol; 3-{[(6S)-3-chloro-6-methylphenanthridin-5(6H)-yl]carbonyl}phenol; 4-[(3-chloro-6-methylphenanthridin-5(6H)-yl)carbonyl]phenol; 4-{[(6R)-3-chloro-6-methylphenanthridin-5(6H)-yl]carbonyl}phenol; 4-{[(6S)-3-chloro-6-methylphenanthridin-5(6H)-yl]carbonyl}phenol; 4-[3-chloro-6-methylphenanthridin-5(6H)-yl]carbonyl]benzene-1,3-diol; 4-{[(6R)-3-chloro-6-methylphenanthridin-5(6H)-yl]carbonyl}benzene-1,3-diol; 4-{[(6S)-3-chloro-6-methylphenanthridin-5(6H)-yl]carbonyl}benzene-1,3-diol; 3-[(3-fluoro-6-methylphenanthridin-5(6H)-yl)carbonyl]phenol; 3-{[(6R)-3-fluoro-6-methylphenanthridin-5(6H)-yl]carbonyl}phenol; 3-{[(6S)-3-fluoro-6-methylphenanthridin-5(6H)-yl]carbonyl}phenol; 4-[(3-fluoro-6-methylphenanthridin-5(6H)-yl)carbonyl]phenol; 4-{[(6R)-3-fluoro-6-methylphenanthridin-5(6H)-yl]carbonyl}phenol; 4-{[(6S)-3-fluoro-6-methylphenanthridin-5(6H)-yl]carbonyl}phenol; 4-[(3-fluoro-6-methylphenanthridin-5(6H)-yl)carbonyl]benzene-1,3-diol; 4-{[(6R)-3-fluoro-6-methylphenanthridin-5(6H)-yl]carbonyl}benzene-1,3-diol; 4-{[(6S)-3-fluoro-6-methylphenanthridin-5(6H)-yl]carbonyl}benzene-1,3-diol; 4-[(3,8-difluoro-6-methylphenanthridin-5(6H)-yl)carbonyl]phenol; 4-{[(6R)-3,8-Difluoro-6-methylphenanthridin-5(6H)-yl]carbonyl}phenol; 4-{[(6S)-3,8-Difluoro-6-methylphenanthridin-5(6H)-yl]carbonyl}phenol; and pharmaceutically acceptable salt and ester forms thereof.

As used herein alone or as part of a group, the term "alkyl" includes both branched and straight-chain saturated aliphatic hydrocarbon groups having the specified number of carbon atoms, e.g. methyl (Me), ethyl (Et), propyl (Pr), isopropyl (i-Pr), isobutyl (i-Bu), secbutyl (s-Bu), tertbutyl (t-Bu), isopentyl, isohexyl and the like. The term "alkyl" further includes both unsubstituted and mono-, di- and tri-substituted hydrocarbon groups, suitable substituents are selected from acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, amino, amino substituted by one or two alkyl groups of from 1 to 6 carbon atoms, aminoacyl, acylamino, azido, cyano, halo, nitro, thioalkoxy of from 1 to 6 carbon atoms, thioalkoxy of from 1 to 6 carbon atoms mono- or di-substituted with lower alkyl or alkoxy, trihalomethyl, aryl, and heteroaryl, with halogen substitution particularly preferred. Preferred alkyl groups have from 1 to 12 carbon atoms, more preferably from 1 to 6 carbon atoms unless otherwise defined. A lower alkyl has from 1 to 6 carbon atoms The carbon number as used in the definitions herein refers to carbon backbone and carbon branching, but does not include carbon atoms of the substituents, such as alkoxy substitutions and the like.

The term "alkenyl" as used herein alone or as part of a group refers to an unsaturated or partially unsaturated aliphatic hydrocarbon group having the specified number of carbon atoms, for example ethenyl, 1-propenyl, 2, butenyl, etc. The term "alkenyl" further includes both unsubstituted and mono-, di- and tri-substituted hydrocarbon groups, suitable substituents are selected from acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, amino, amino substituted by one or two alkyl groups of from 1 to 6 carbon atoms, aminoacyl, acylamino, azido, cyano, halo, nitro, thioalkoxy of from 1 to 6 carbon atoms, thioalkoxy of from 1 to 6 carbon atoms mono- or di-substituted with lower alkyl or alkoxy, trihalomethyl, aryl, and heteroaryl, with halogen substitution particularly preferred. Preferred alkenyl groups have from 1 to 12 carbon atoms.

The term "alkynyl", as used herein alone or as part of a group refers to a substituted or unsubstituted aliphatic hydrocarbon chain and includes, but is not limited to, straight and branched chains and containing at least one triple bond. Preferably, the alkynyl moiety has 2 to 10 carbon atoms. In certain embodiments, the alkynyl can contain more than one triple bond and, in such cases, the alknyl group must contain at least three carbon atoms. Specifically included within the definition of "alkynyl" are those aliphatic hydrocarbon chains that are optionally substituted. Suitable substituents are selected from acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, amino, amino substituted by one or two alkyl groups of from 1 to 6 carbon atoms, aminoacyl, acylamino, azido, cyano, halo, nitro, thioalkoxy of from 1 to 6 carbon atoms, thioalkoxy of from 1 to 6 carbon atoms mono- or di-substituted with lower alkyl or alkoxy, trihalomethyl, aryl, and heteroaryl.

The term "perfluoroalkyl", as used herein, whether used alone or as part of another group, refers to an alkyl group substituted with two or more fluorine atoms and includes, but is not limited to, straight or branched chains, such as —$CF_3$, —$CH_2CF_3$, —$CF_2CF_3$ and —$CH(CF_3)_2$.

The term "carbonyl" as used herein alone or as part of a group refers to the group —C(=O).

The term "acyl", employed alone or in combination with other terms, is defined herein as, unless otherwise stated, either an arylalkyl, heteroarylalkyl, ($C_2$-$C_{10}$) straight chain, or ($C_4$-$C_{11}$) branched-chain monovalent hydrocarbon moiety; wherein the carbon atom, covalently linked to the defined chemical structure, is oxidized to the carbonyl oxidation state. Such hydrocarbon moieties may be mono or polyunsaturated, and may exist in the E or Z configurations. The compounds of this invention are meant to include all possible E and Z configurations. Examples of acyl moieties include, but are not limited to, chemical groups such as acetyl, propionyl, butyryl, 3,3-dimethylbutyryl, trifluoroacetyl, pivaloyl, hexanoyl, hexenoyl, decanoyl, benzoyl, nicotinyl, isonicotinyl, and homologs, isomers, and the like.

The term "alkylamino" as used herein alone or as part of a group refers to the group —NH-alkyl The term "alkylaminocarbonyl" as used herein alone or as part of a group refers to an alkylamino group bonded through a carbonyl group.

The term "dialkylamino" herein alone or as part of a group refers to the group —N(alkyl)$_2$, where the alkyl group is the same or different.

The term "dialkylaminocarbonyl" as used herein alone or as part of a group refers to a dialkylamino group bonded through a carbonyl group.

The term "alkylaminocarbonyl" as used herein alone or as part of a group refers to an alkylamino group bonded through a carbonyl group.

The term "alkoxy" as used herein alone or as part of a group refers to the group $R_a$—O— wherein $R_a$ is an alkyl group as defined above.

The term" alkoxycarbonyl" as used herein alone or as part of a group refers to an alkoxy group bonded through a carbonyl group.

The term "cycloalkyl" includes cyclized alkyl chains having the specified number of carbon atoms, e.g., cyclopropyl, cyclobutyl, cyclopentyl, and cyclohexyl.

The term "cycloalkenyl" includes cyclized alkyl chains containing an alkenyl group having the specified number of carbon atoms, e.g., cyclopentenyl, cyclohexenyl, and the like. Specifically included within the definition of cyclolalkyl and cycloalkenyl are those cycloalkyl groups that are optionally substituted. Suitable substituents are selected from acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, amino, amino substituted by one or two alkyl groups of from 1 to 6 carbon atoms, aminoacyl, acylamino, azido, cyano, halo, nitro, thioalkoxy of from 1 to 6 carbon atoms, thioalkoxy of from 1 to 6 carbon atoms mono- or di-substituted with lower alkyl or alkoxy, trihalomethyl, aryl, and heteroaryl. Preferred cycloalkyl and cycloalkenyl groups contain from 3 to 15 carbon atoms.

The term "halogen" includes fluorine, chlorine, iodine, and bromine.

The term "aryl" refers to an aromatic carbocyclic moiety of up to 20 carbon atoms, which can be a single ring (monocyclic) or multiple rings (bicyclic, up to three rings) fused together or linked covalently. Any suitable ring position of the aryl moiety can be covalently linked to the defined chemical structure. Examples of aryl moieties include, but are not limited to, chemical groups such as phenyl, 1-naphthyl, 2-naphthyl, dihydronaphthyl, tetrahydronaphthyl, biphenyl, anthryl, phenanthryl, fluorenyl, indanyl, biphenylenyl, acenaphthenyl, acenaphthylenyl, and the like. Specifically included with the term "aryl" are those aryl groups that are optionally substituted. Suitable substituents are selected from acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, amino, amino substituted by one or two alkyl groups of from 1 to 6 carbon atoms, aminoacyl, acylamino, azido, cyano, halo, nitro, thioalkoxy of from 1 to 6 carbon atoms, thioalkoxy of from 1 to 6 carbon atoms mono- or di-substituted with lower alkyl or alkoxy, trihalomethyl, aryl, and heteroaryl. Preferred aryl groups contain from 6 to 14 carbon atoms.

The term "arylalkyl", as used herein, whether used alone or as part of another group, refers to the group —$R_a$—$R_b$, where $R_a$ is an alkyl group as defined above, substituted by $R_b$, an aryl group, as defined above. In a preferred embodiment, the alkyl chain is either a ($C_1$-$C_6$) straight or ($C_2$-$C_7$) branched-chain saturated hydrocarbon moiety. Examples of arylalkyl moieties include, but are not limited to, chemical groups such as benzyl, 1-phenylethyl, 2-phenylethyl, diphenylmethyl, 3-phenylpropyl, 2-phenylpropyl, fluorenylmethyl, and homologs, isomers, and the like. These may be optionally substituted as discussed for the aryl and alkyl groups defined above.

The term "heterocyclic ring or ring system", employed alone or in combination with other terms, is defined herein as an unsaturated, partially unsaturated or saturated ring or ring system, which can be a single ring (monocyclic) or multiple rings (bicyclic, up to three rings) fused together or linked covalently. The rings can contain from one to four hetero atoms selected from nitrogen (N), oxygen (O), or sulfur (S), wherein the nitrogen or sulfur atom(s) are optionally oxidized, or the nitrogen atom(s) are optionally quarternized. Any suitable ring position of the heteroaryl moiety can be covalently linked to the defined chemical structure. Examples of unsaturated heterocyclic rings or ring systems include, but are not limited to, heterocycles such as furan, thiophene, pyrrole, N-methylpyrrole, pyrazole, N-methylpyrazole, imidazole, N-methylimidazole, oxazole, isoxazole, thiazole, isothiazole, 1H-tetrazole, 1-methyltetrazole, 1,3,4-oxadiazole, 1H-1,2,4-triazole, 1-methyl-1,2,4-triazole 1,3,4-triazole, 1-methyl-1,3,4-triazole, pyridine, pyrimidine, pyrazine, pyridazine, benzoxazole, benzisoxazole, benzothiazole, benzofuran, benzothiophene, thianthrene, dibenzo[b,d]furan, dibenzo[b,d]thiophene, benzimidazole, N-methylbenzimidazole, indole, indazole, quinoline, isoquinoline, quinazoline, quinoxaline, purine, pteridine, 9H-carbazole, β-carboline, and the like. Examples of saturated or partially unsaturated heterocyclic rings or ring systems include, but are not limited to, chemical groups such as azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothienyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydro-1,4-dioxanyl, tetrahydrofuranyl, tetrahydrothienyl, tetrahydroquinolinyl, tetrahydroisoquinolinyl, and the like. Specifically included within the term "heterocycle" are those heterocyclic groups that are optionally substituted. Suitable substituents are selected from acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, amino, amino substituted by one or two alkyl groups of from 1 to 6 carbon atoms, aminoacyl, acylamino, azido, cyano, halo, nitro, thioalkoxy of from 1 to 6 carbon atoms, thioalkoxy of from 1 to 6 carbon atoms mono- or di-substituted with lower alkyl or alkoxy, and trihalomethyl.

As used herein, the term "heteroaryl", whether used alone or as part of another group, is defined as a substituted or unsubstituted aromatic heterocyclic ring system (monocyclic or bicyclic). Heteroaryl groups can have, for example, from about 3 to about 50 carbon atoms (unless explicitly specified otherwise) with from about 4 to about 10 being preferred. In some embodiments, heteroaryl groups are aromatic heterocyclic rings systems having about 4 to about 14 ring atoms and containing carbon atoms and 1, 2, 3, or 4 heteroatoms selected from oxygen, nitrogen or sulfur. Representative heteroaryl groups are furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, and isoquinoline. Bicyclic aromatic heteroaryl goups include phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Specifically included within the definition of "heteroaryl" are those aromatic heterocyclic rings that are substituted, for example with 1 to 5 substituents selected from the group consisting of acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, amino, amino substituted by one or two alkyl groups of from 1 to 6 carbon atoms, aminoacyl, acylamino, azido, cyano, halo, nitro, thioalkoxy of from 1 to 6 carbon atoms, thioalkoxy of from 1 to 6 carbon atoms mono- or di-substituted with lower alkyl or alkoxy, and trihalomethyl. Where there is more than one substituent the substituents may be the same or different.

The compounds of the present invention can be converted to salts, in particular pharmaceutically acceptable salts using art recognized procedures. The compounds of formulas 1 to 12 that have a basic center can form acid addition salts. These are formed, for example, with strong inorganic acids, such as mineral acids for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid such as saturated or unsaturated dicarboxylic acids, for example oxalic, malonic, succinic, maleic, fumaric, phthalic, or terephthalic acid, such as hydroxycarboxylic acids, for example ascorbic, glycolic, lactic, malic, tartaric or citric acid, such as amino acids, for example aspartic or glutamic acid, or such as benzoic acid, or with organic sulfonic acids, such as alkane- (of 1 to 4 carbon atoms) or arylsulfonic acids, for example methane- or p-toluenesulfonic acid. Corresponding acid addition salts can also be formed having, if desired, an additionally present basic center. The compounds of formulas 1 to 12 having at least one acid group can form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-tert-butyl-, diethyl-, diisopropyl-, triethyl-, tributyl- or dimethylpropylamine, or a mono-, di-, or trihydroxy lower alkylamine, for example mono-, di- or triethanolamine. Internal salts can furthermore be formed. Salts which are unsuitable for pharmaceutical uses but which can be employed, for example, for the isolation or purification of free compounds of formulas 1 to 12 or their pharmaceutically acceptable salts, are also included.

Pharmaceutically acceptable esters refers to esters that are pharmaceutically acceptable and have the desired pharmacological properties. Pharmaceutically acceptable esters include esters formed from carboxy, sulfonyloxy, and phosphonoxy groups present in the compounds, e.g. $C_{1-6}$ alkyl esters. When there are two acidic groups present, a pharmaceutically acceptable ester can be a mono-acid-mono-ester or a di-ester; and similarly where there are more than two acidic groups present, some or all of such groups can be esterified.

As used in accordance with this invention, the term "providing," with respect to providing a compound or substance covered by this invention, means either directly administering such a compound or substance, or administering a prodrug, derivative, or analog which will form the effective amount of the compound or substance within the body.

Certain of the compounds of Formulas 1 to 12 contain stereogenic carbon atoms or other chiral elements and thus give rise to stereoisomers, including enantiomers and diastereomers. All stereoisomers of the compounds of the instant invention are contemplated, either in admixture or in pure or substantially pure form. The definition of the compounds according to the invention embraces all possible stereoisomers and their mixtures. Throughout this application, the name of the product, where the absolute configuration of an asymmetric center is not indicated is intended to embrace the individual stereoisomers as well as mixtures of stereoisomers.

Where an enantiomer (or a particular blend of enantiomers) is preferred, it can, in some embodiments, be provided substantially free of the corresponding enantiomer(s). Thus, an enantiomer substantially free of the corresponding enantiomer refers to a compound that is isolated or separated via separation techniques or prepared free of the corresponding enantiomer. "Substantially free," as used herein, means that the compound is made up of a significantly greater proportion of one enantiomer. In preferred embodiments, the compound is made up of at least about 90% by weight of a preferred enantiomer. In other embodiments of the invention, the compound is made up of at least about 99% by weight of a preferred enantiomer. Preferred enantiomers can be isolated from racemic mixtures by any method known to those skilled in the art, including high performance liquid chromatography (HPLC) and the formation and crystallization of chiral salts, or preferred enantiomers can be prepared by methods described herein. The racemic forms can be resolved by physical methods, such as, for example, fractional crystallization, separation or crystallization of diastereomeric derivatives or separation by chiral column chromatography. The individual optical isomers can be obtained from the racemates by conventional methods, such as, for example, salt formation with an optically active acid followed by crystallization. Methods for the preparation of preferred enantiomers are described, for example, in Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); and Wilen, S. H. Tables of Resolving Agents and Optical Resolutions p. 268 (E. L. Eliel, Ed., Univ. of Notre Dame Press, Notre Dame, IN 1972), each of which is incorporated herein by reference in its entirety and for all purposes. Accordingly, the present invention embraces the racemic forms of the claimed compounds and the isolated optical isomers having the specified activity.

It should be understood that the present invention includes prodrug forms of the compounds of Formulas 1 to 12. Various forms of prodrugs are well known in the art. For examples of such prodrug derivatives, see: (a) Design of Prodrugs, edited by H. Bundgaard (Elsevier, 1985); and Methods in Enzymology, Vol. 42, pp. 309-396, edited by K. Widder et al., (Academic Press, 1985); (b) A Textbook of Drug Design and Development, edited by Krosgaard-Larsen and H. Bundgaard, Chapter 5, "Design and Application of Prodrugs," by H. Bundgaard, pp. 113-191 (1991); (c) H. Bundgaard, Advanced Drug Deliver Reviews, 8, pp. 1-38 (1992); (d) H. Bundgaard et al., Journal of Pharmaceutical Sciences, 77, 285 (1988); and (e) N. Kayeka et al., Chem. Phar. Bull., 32, 692 (1984), each of which is incorporated herein by reference in its entirety and for all purposes. For example, a representative scheme for synthesizing an exemplary prodrug of the present invention is as follows:

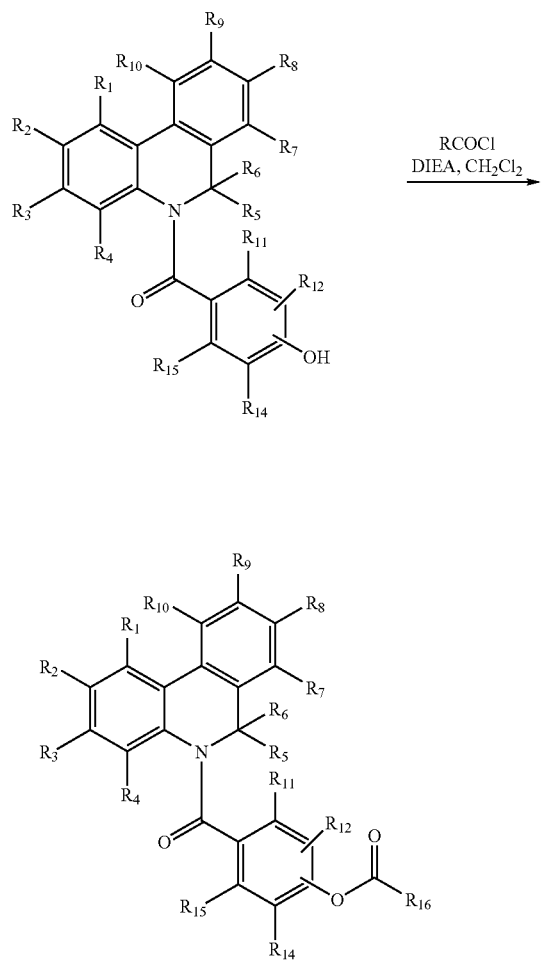

Solvates (e.g., hydrates) are also within the scope of the present invention. Methods of solvation are generally known in the art. Accordingly, the compounds of the instant invention can be in the free or hydrate form, and can be obtained by methods exemplified by the following schemes below.

Compounds of the present invention can be prepared by those skilled in the art of organic synthesis employing conventional methods that utilize readily available reagents and starting materials. The compounds of the present invention can be prepared from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. Although not limited to any one or several sources, classic texts such as Smith, M. B.; March, J. *March's Advanced Organic Chemistry: Reactions, Mechanisms, and Structure,* 5$^{th}$ ed.; John Wiley & Sons: New York, 2001; and Greene, T. W.; Wuts, P. G. M. *Protective Groups in Organic Synthesis,* 3$^{rd}$ ed.; John Wiley & Sons: New York, 1999 are useful and recognized reference textbooks of organic synthesis known to those in the art. The following synthetic schemes are designed to illustrate, but not limit, general procedures for the preparation of representative compounds of the present invention. The skilled practitioner will know how to make use of variants of these process steps.

In scheme I the compounds can be conveniently prepared from an appropriately substituted phenanthridine. A general preparation of the phenanthridines is described by M. Lysen, J. L. Kristensen, M. Begtrup; *Organic Letters,* 2002, 4, 257. Several other methods of preparation of substituted phenanthridines are known in the literature (see P K. Patra, J. R. Suresh, H. Ila, H. Junjappa, *Tetrahedron,* 1998, 54, 10167). In scheme I, step a, a suitably substituted phenanthridine (1), either commercially available, known in the literature, or prepared according to methods known and established for the preparation of said phenanthridines, including the schemes described below; wherein, $R_1$ through $R_{15}$ are herein before defined, is reacted with an $R_5$—Li reagent, either commercially available, known in the literature, or prepared according to methods known and established for the formation of lithium reagents, in a suitable solvent, such as diethyl ether, tetrahydrofuran, 1,4-dioxane, or the like, at temperatures between —78° C. and room temperature. The lithium amide salt (2A) is reacted in situ with a suitably substituted benzoyl chloride (3), either commercially available, known in the literature, or prepared according to methods known and established for the preparation of said benzoyl chlorides. Alternatively, the suitably substituted phenanthridine is reduced in situ to the intermediate dihydrophenanthridine (2B) in the presence of a suitable benzoyl chloride (3), as previously described, in a non-reactive solvent, such as diethyl ether, tetrahydrofuran, and the like, at temperatures between –78° C. and room temperature to provide the protected phenol (4). A methyl ether (4); wherein, $R_{13}$ is a methyl group, can be de-methylated in step d to the corresponding phenol (5) by reacting (4) with boron tribromide in the presence of an excess of olefin or cycloolefin, such as cyclohexene, acting as a bromine and hydrogen bromide scavenger, in a suitably halogenated solvent such as chloroform, 1,2-dichloroethane, or dichloromethane, and the like. Alternatively, the methyl ether (4) can be de-methylated to phenol (5) by reacting (4) with boron trichloride, in the presence of quaternary ammonium iodides, such as tetrabutylammonium iodide, in a suitably halogenated solvent such as chloroform, 1,2-dichloroethane, or dichloromethane, and the like, at temperatures between –78° C. and room temperature for two to twenty-four hours.

If $R_{13}$ is a benzyl or diphenylmethyl protecting group, removal by suitably compatible hydrogenolysis techniques, known in the literature for effecting such transformations, such as hydrogen and 5% palladium-on-carbon catalysts will afford the desired phenol (5).

If —$OR_{13}$ is a carbonate moiety, treatment of (4) with a 1 N sodium hydroxide solution in methanol at typically 40° C. to 75° C., for a length of time, typically about twelve hours, will remove the protecting group to afford the desired phenol (5).

Scheme I
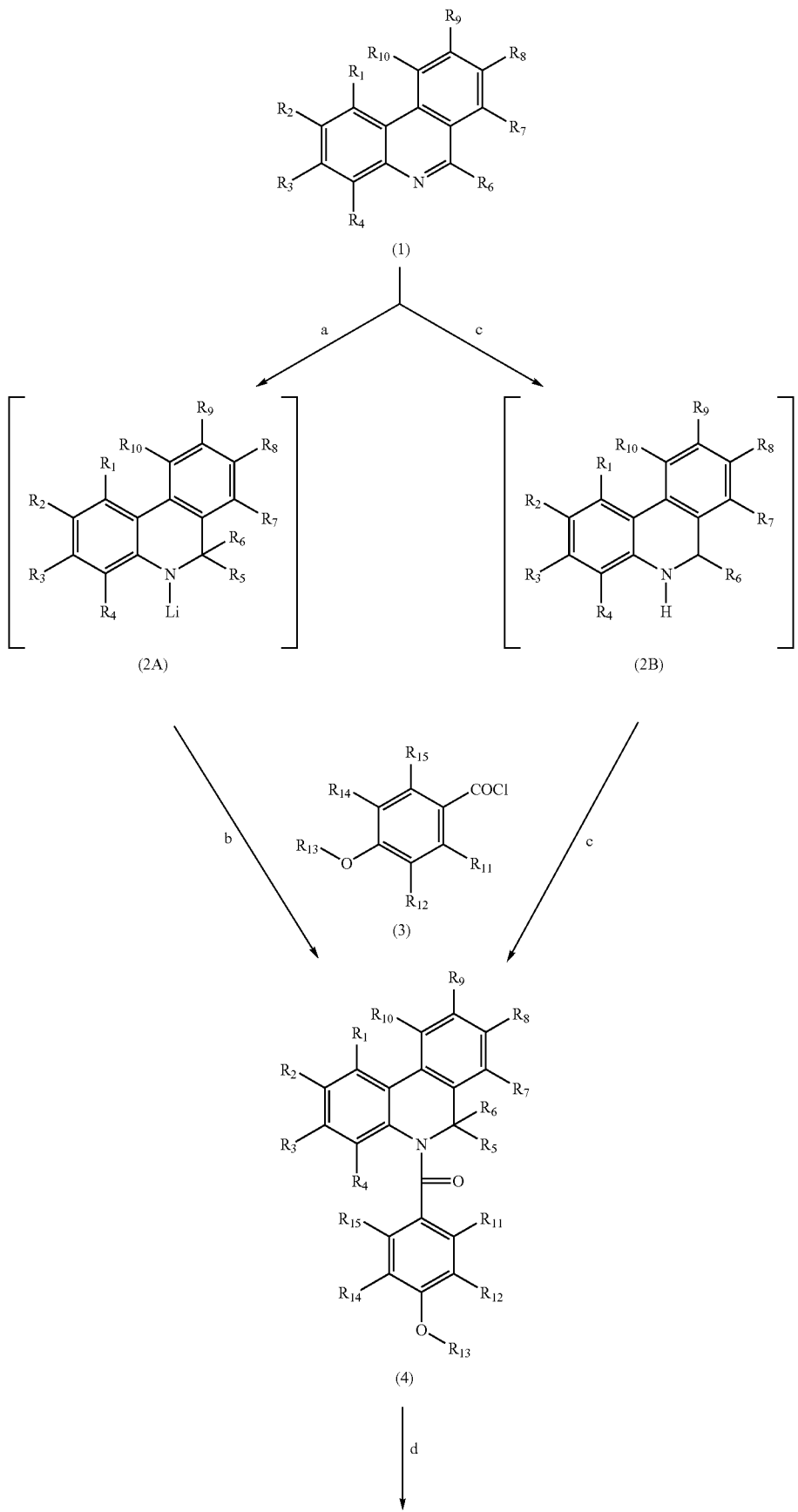

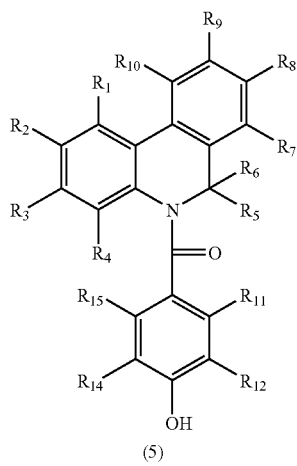

(5)

a. R$_5$Li, ether solvent, -78° C. to RT;
b. (3) at -78° C. to RT;
c. (3), DIPEA, THF; or when R$_5$ = H
   (CH$_3$)$_2$——BH$_3$, (S)-2-methly-CBS-oxazaborolidine, THF
d. When R$_{13}$ is methyl: BBr$_3$, cyclohexene, methylene chloride, 2-24 h.,
   (when R$_5$ = H, preparative chiral HPLC resolution)

In Scheme II, step aa, a suitably substituted arylboronic acid or ester (6), either commercially available, known in the literature, or prepared according to methods known and established for the preparation of said arylboronic acids or esters, including procedures exemplified in the experimental section of this application; wherein, L is a fluorine or chlorine atom, R$_1$ through R$_{15}$, are herein before defined and R$_{20}$ and R$_{21}$ can be hydrogen, lower alkyl or bridged alkyl, in the presence of a coupling catalyst, is reacted with a suitably substituted alkyl aryl ketone (7), either commercially available, known in the literature, or prepared according to methods known and established for the preparation of said alkyl aryl ketones, including procedures exemplified in the experimental section of this application; wherein, W and R$_6$ through R$_{10}$ are herein before defined. The biphenylketone (8) is reacted in step bb with an ammonium source, such as ammonium chloride or ammonium acetate, and the like, either commercially available, or known in the literature, in a suitable solvent such as methanol, toluene, tetrahydrofuran, 1,2-dichloroethane, and the like, optionally in the presence of an acid catalyst such as p-toluenesulfonic acid or pyridinium p-toluenesulfonate, followed in a second step cc by reduction of the intermediate imine with an acceptable hydride source, such as sodium cyanoborohydride, sodium borohydride, lithium aluminum hydride, or diisobutylaluminum hydride, or the like. The intermediate imine can be isolated or not isolated. The conjugate base of a suitable, nucleophilic R$_5$, such as methyllithium, tert-butyllithium, and the like, can be substituted for the hydride source to afford a tertiary biphenylamine as the product of step cc. The biphenylamine (9) can be separated into it's respective enantiomers (9S) and (9R) by subjecting (9) to either an analytical chiral separation, an enzymatic or chemical resolution, or a de novo enantiospecific synthesis of either (9S) or (9R) according to methods known and established in the literature for the enantiospecific synthesis of benzylic amines. The chemical resolution of (9) is carried out by employing a suitable chiral acid, either commercially available or known in the literature, according to methods known and established for the resolution of benzylic amines. The biphenylamine (9), either as the racemate or enantiomerically pure, is then reacted in step dd with an acid chloride or anhydride, in a suitable solvent such as acetonitrile, 1,2-dichloroethane, or dichloromethane, and the like, optionally in the presence of an acid scavenger such as triethylamine, diisopropylethylamine, pyridine, or potassium carbonate, and the like, and further optionally in the presence of a known acylation promoter or catalyst, such as 4-(N,N-dimethylamino)pyridine at −20° C. to room temperature for several hours. In step ee, treatment of the carboxamideamide (10) with lithium or potassium hexamethyldisilamide, LDA and the like, either commercially available, or known in the literature in a suitable solvent such as tetrahydrofuran at 70° C. for 24-48 hours afforded phenanthridine (4). The protected phenol can be de-protected in step ff to phenol (5) as previously described.

Scheme II.
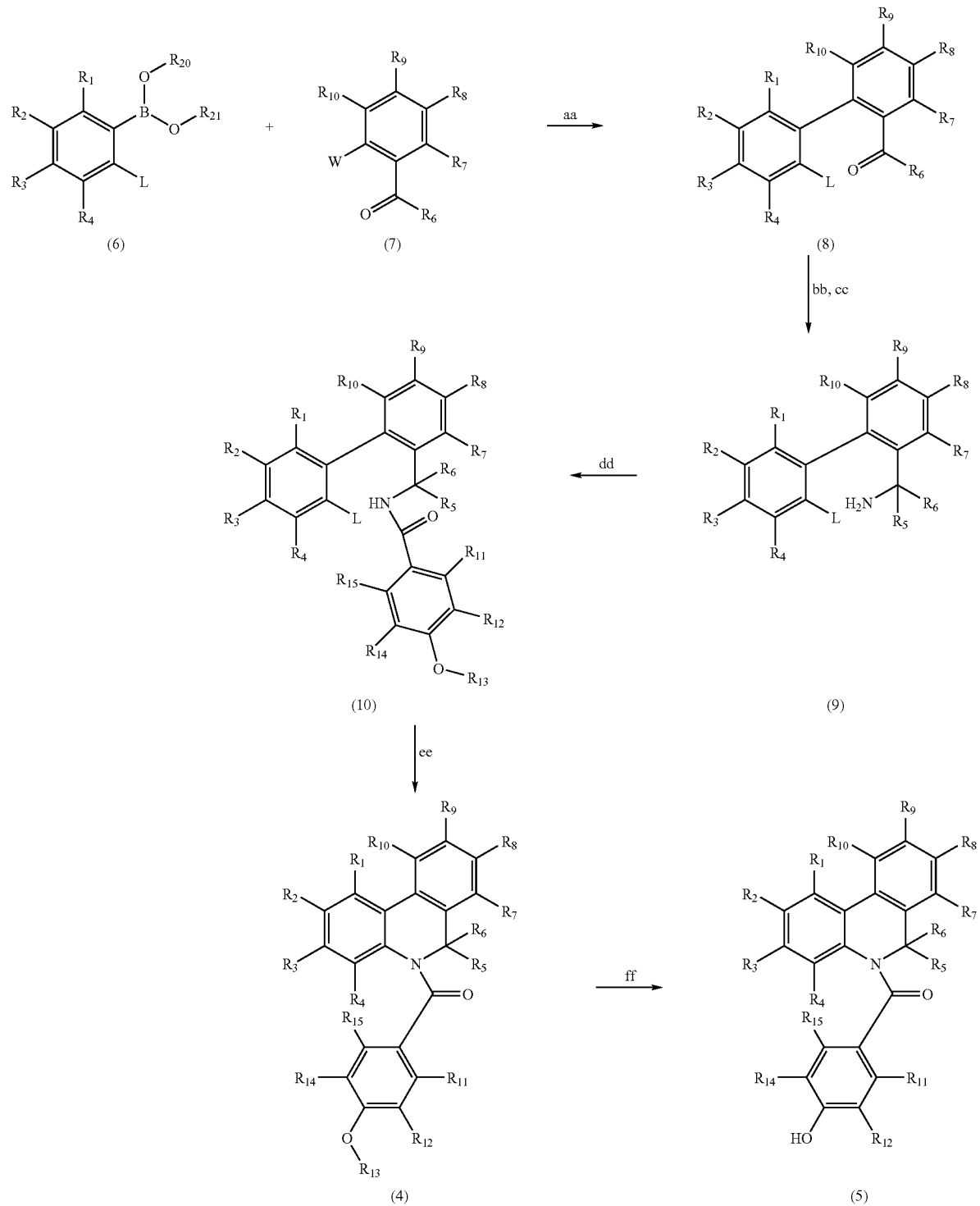
aa. Pd(OAc)$_2$, K$_2$CO$_3$, tetrabutylammonium bromide, THf, 60° C., 2-12 h;
bb. NH$_4$OAc, MeOH, 60° C.;
cc. When R$_5$ is hydrogen, NaCNBH$_3$, MeOH, 60° C., 12 h;
dd. ArCOCl wherein R$_{13}$ is methyl: triethylamine, CH$_2$Cl$_2$, 2-12 h;
ee. KHMDS, THF, 70° C., 16 h;
ff. When R$_{13}$ is methyl: BBr$_3$, cyclohexane, dichloromethane, 2-24 h.

In preferred embodiments, the present invention concerns methods of treating a subject comprising the step of providing a therapeutically effective amount of a ligand which modulates NF-kB transcription factor by interaction with estrogen receptor ER-α, estrogen receptor ER-β, or both ER-α and ER-β estrogen receptors, preferably with a substantial absence of creatine kinase stimulation. In certain preferred embodiments, the administration is with a substantial absence of uterotropic activity. Preferred compounds of the present invention modulate NF-kB transcription factor by interaction with estrogen receptor ER-α, estrogen receptor ER-β, or both ER-α and ER-β estrogen receptors preferably with a substantial absence of creatine kinase stimulation.

Preferred compounds of the present invention modulate, e.g., inhibit cytokine expression. For example, preferred compounds inhibit NF-$_κ$B activity and thus IL-6 expression. Accordingly, preferred compounds of the present invention possess anti-inflammatory activity and are anti-inflammatory compounds useful for the treatment of diseases associated with increased cytokine, e.g., IL-6, expression, such as chronic inflammatory disease. In a particularly preferred embodiment, compounds of the present invention do not induce creatine kinase expression and accordingly, unlike classic estrogens, do not stimulate uterine and breast cell proliferation.

The compounds according to the present invention have pharmacological properties that can be confirmed by a number of pharmacological assays, including the IL-6 and creatine kinase assays described in the example section herein. Preferably the compounds of the present invention can be used to treat chronic inflammatory disease such as atherosclerosis, myocardial infarction (MI), congestive heart failure (CHF), inflammatory bowel disease, e.g., ulcerative colitis and Crohn's disease, and arthritis, e.g., rheumatoid arthritis, and other diseases and conditions including those disclosed herein. For the purposes of the present invention, a chronic inflammatory disease is any disease characterized by chronic inflammation.

Preferred compounds of this invention are useful in treating osteoporosis and in the inhibition of bone demineralization, which may result from an imbalance in an individual's formation of new bone tissues and the resorption of older tissues, leading to a net loss of bone. Such bone depletion results in a range of individuals, particularly in post-menopausal women, women who have undergone bilateral oophorectomy, those receiving or who have received extended corticosteroid therapies, those experiencing gonadal dysgenesis, and those suffering from Cushing's syndrome. Special needs for bone, including teeth and oral bone, replacement can also be addressed using these compounds in individuals with bone fractures, defective bone structures, and those receiving bone-related surgeries and/or the implantation of prosthesis. In addition, preferred compounds can be used in treatment or inhibition for osteoarthritis, hypocalcemia, hypercalcemia, Paget's disease, osteomalacia, osteohalisteresis, multiple myeloma and other forms of cancer having deleterious effects on bone tissues.

Preferred compounds of the present invention are also active in the brain and are therefore useful for inhibiting or treating Alzheimer's disease, cognitive decline, decreased libido, senile dementia, neurodegenerative disorders, depression, anxiety, insomnia, schizophrenia, and infertility. Preferred compounds of the present invention are also useful in treating benign or malignant abnormal tissue growth including, glomerulosclerosis, prostatic hypertrophy, uterine leiomyomas, breast cancer, scleroderma, fibromatosis, endometriosis, endometrial cancer, polycystic ovary syndrome, endometrial polyps, benign breast disease, adenomyosis, ovarian cancer, melanoma, prostate cancer, cancers of the colon, CNS cancers, such as glioma or astioblastomia.

Preferred compounds of the present invention are cardioprotective and are antioxidants, and are useful in lowering cholesterol, triglycerides, Lp(a), and LDL levels; inhibiting or treating hypercholesteremia, hyperlipidemia, cardiovascular disease, atherosclerosis, peripheral vascular disease, restenosis, and vasospasm, and inhibiting vascular wall damage from cellular events leading toward immune mediated vascular damage.

Preferred compounds of the present invention are also useful in treating disorders associated with inflammation or autoimmune diseases, including inflammatory bowel disease (Crohn's disease, ulcerative colitis, indeterminate colitis), arthritis (rheumatoid arthritis, spondyloarthropathies, osteoarthritis), pleurisy, ischemia/reperfusion injury (e.g., stroke, transplant rejection, myocardial infarction, etc.), asthma, giant cell arteritis, prostatitis, uveitis, psoriasis, multiple sclerosis, systemic lupus erythematosus and sepsis.

Preferred compounds of the present invention are also useful in treating ocular disorders including cataracts, uveitis, and macular degeneration and in treating skin conditions such as aging, alopecia, and acne.

Preferred compounds of the present invention are also useful in treating metabolic disorders such as type-II diabetes, of lipid metabolism, appetite (e.g. anorexia nervosa and bulimia).

Preferred compounds of the present invention are also useful in treating bleeding disorders such as hereditary hemorrhagic telangiectasia, dysfunctional uterine bleeding, and combating hemorrhagic shock.

Preferred compounds of the present invention are useful in disease states where amenorrhea is advantageous, such as leukemia, endometrial ablations, chronic renal or hepatic disease or coagulation diseases or disorders.

The compounds of the present invention can be administered to a subject for a variety of purposes. Except when noted, the terms "subject" or "patient" are used interchangeably and refers to all mammalian species. For example, the term includes mammals such as human patients and non-human primates, as well as experimental animals such as rabbits, rats, and mice, and other animals. Accordingly, the term "subject" or "patient" as used herein means any mammalian patient or subject to which the compounds of the invention can be administered. Patients for treatment according to the methods of the invention preferably are identified using accepted screening methods to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and formulations of the present invention. A subject "in need thereof" is a subject suffering or suspected to be suffering from a certain condition or disease state treatable by the methods of the present invention.

As used herein, the term "treating" or "treatment" refers to any indicia of success in amelioration of an injury, pathology, or condition, including any objective or subjective parameter such as abatement; inhibition; remission; diminishing of symptoms or making the injury, pathology, or condition more tolerable to the patient; slowing in the rate of degeneration or decline; making the final point of degeneration less debilitating; or improving a subject's physical or mental well-being. The treatment or amelioration of symptoms can be based on objective or subjective parameters; including the results of a physical examination, neurological examination, and/or psychiatric evaluation. "Treating" or "treatment of a disease or condition characterized by chronic inflammation" includes preventing the onset of symptoms in a subject that may be predisposed to an inflammatory disease but does not yet experience or exhibit symptoms of the disease (prophylactic treatment), inhibiting the symptoms of the disease (slowing or arresting its development), providing relief from the symptoms or side-effects of the disease (including palliative treatment), and/or relieving the symptoms of the disease (causing regression). Treating or treatment of any disease or condition disclosed herein includes preventing the onset of symptoms in a subject that may be predisposed to said disease or condition but does not yet experience or exhibit symptoms of the disease or condition (prophylactic treatment), inhibiting the symptoms of the disease or condition (slowing or arresting its development), providing relief from the symptoms or side-effects of the disease or condition (including palliative treatment), and/or relieving the symptoms of the disease or condition (causing regression). Accordingly, the term "treating" includes the administration of the compounds or agents of the present invention to a subject to prevent or delay, to alleviate, or to arrest or inhibit development of the symptoms or conditions associated with a disease state. A skilled medical practitioner will know how to use standard methods to determine whether a patient is suffering from a disease characterized by chronic inflammation and/or increased cytokine expression.

"Concomitant administration" of a known drug or treatment with a pharmaceutical composition of the present invention means administration of the drug (or treatment) and the compound of the present invention at such time that both the known drug (or treatment) and the composition of the present invention will have a therapeutic effect. Such concomitant administration can involve concurrent (i.e. at the same time), prior, or subsequent administration of the drug (or treatment) with respect to the administration of a compound of the present invention. A person of ordinary skill in the art, would have no difficulty determining the appropriate timing, sequence and dosages of administration for particular drugs and compositions of the present invention. For example, the compounds of this invention can be used in combination (administered together or sequentially) with known drugs useful in the treatment of chronic inflammation.

The present invention provides compositions comprising a compound of the present invention in combination with a pharmaceutically acceptable carrier. In a preferred embodiment, the compounds are formulated as pharmaceuticals to diseases associated with chronic inflammation In general, compounds of the present invention can be administered as pharmaceutical compositions by any method known in the art for administering therapeutic drugs including oral, buccal, topical, systemic (e.g., transdermal, intranasal, or by suppository), or parenteral (e.g., intramuscular, subcutaneous, or intravenous injection). Compositions can take the form of tablets, pills, capsules, semisolids, powders, sustained release formulations, solutions, suspensions, emulsions, syrups, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, can be found in such standard references as Alfonso A R: Remington's Pharmaceutical Sciences, 17th ed., Mack Publishing Company, Easton Pa., 1985. Suitable liquid carriers, especially for injectable solutions, include water, aqueous saline solution, aqueous dextrose solution, and glycols. In some embodiments of the present invention, compounds of the present invention suitable for use in the practice of this invention can be administered either singly or in combination with at least one other compound of this invention. Compounds suitable for use in the practice of the present invention can also be administered with at least one other conventional therapeutic agent for the disease being treated.

Aqueous suspensions of the invention can contain a compound of the present invention in admixture with excipients suitable for the manufacture of aqueous suspensions. Such excipients can include, for example, a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol monooleate), or a condensation product of ethylene oxide with a partial ester derived from fatty acid and a hexitol anhydride (e.g., polyoxyethylene sorbitan mono-oleate). The aqueous suspension can also, for example, contain one or more preservatives such as ethyl or n-propyl p-hydroxybenzoate, one or more coloring agents, one or more flavoring agents, and one or more sweetening agents, such as sucrose, aspartame or saccharin. Formulations can be adjusted for osmolarity.

Oil suspensions can be formulated by suspending a compound of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. Where the compounds are sufficiently soluble they can be dissolved directly in normal saline with or without the use of suitable organic solvents, such as propylene glycol or polyethylene glycol. Dispersions of the finely divided compounds can be made-up in aqueous starch or sodium carboxymethyl cellulose solution, or in suitable oil, such as arachis oil. These formulations can be sterilized by conventional, well known sterilization techniques. The formulations can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of compounds of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol. The formulations of commends can be presented in unit-dose or multi-dose sealed containers, such as ampules and vials.

Injection solutions and suspensions can be prepared from sterile powders, granules, and tablets of the kind previously described.

Compounds suitable for use in the practice of this invention can be administered orally. The amount of a compound of the present invention in the composition can vary widely depending on the type of composition, size of a unit dosage, kind of excipients, and other factors well known to those of ordinary skill in the art.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc. suitable for ingestion by the patient. Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions.

Pharmaceutical preparations for oral use can be obtained through combination of the compounds of the present invention with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, or sorbitol; starch from corn, wheat, rice, potato, or other plants; cellulose such as methyl cellulose, hydroxymethyl cellulose, hydroxypropylmethyl-cellulose or sodium carboxymethylcellulose; and gums including arabic and tragacanth; as well as proteins such as gelatin and collagen. If desired, disintegrating or solubilizing agents can be added, such as the cross-linked polyvinyl pyrrolidone, agar, alginic acid, or a salt thereof, such as sodium alginate. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compounds of the present invention can also be administered in the form of suppositories for rectal administration of the drug. These formulations can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

The compounds of the present invention can also be administered by intranasal, intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995).

The compounds of the present invention can be administered in sustained or controlled release dosage forms (e.g., employing a slow release bioerodable delivery system), including depot injections, osmotic pumps (such as the Alzet implant made by Alza), pills, transdermal and transcutaneous (including electrotransport) patches, and the like, for prolonged administration at a predetermined rate, preferably in unit dosage forms suitable for single administration of precise dosages. The compositions will typically include a conventional pharmaceutical carrier or excipient and a compound of the invention. In addition, these compositions can include other active agents, carriers, adjuvants, and the like.

The compounds of the present invention can be delivered transdermally, by a topical route, formulated as applicator sticks, solutions, suspensions, emulsions, gels, creams, ointments, pastes, jellies, paints, powders, and aerosols.

Encapsulating materials can also be employed with the compounds of the present invention and the term "composition" is intended to include the active ingredient in combination with an encapsulating material as a formulation, with or without other carriers. For example, the compounds of the present invention can also be delivered as microspheres for slow release in the body.

In another embodiment, the compounds of the present invention can be delivered by the use of liposomes which fuse with the cellular membrane or are endocytosed. By using liposomes, particularly where the liposome surface carries ligands specific for target cells, or are otherwise preferentially directed to a specific organ, one can focus the delivery of the compound into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989).

In other cases, the preferred preparation can be a lyophilized powder which can contain, for example, any or all of the following: 1 mM-50 mM histidine, 0.1%-2% sucrose, 2%-7% mannitol, at a pH range of 4.5 to 5.5, that is combined with buffer prior to use.

A pharmaceutical composition of the invention can optionally contain, in addition to a compound of the present invention, at least one other therapeutic agent useful in the treatment of a disease or condition associated with chronic inflammation.

The pharmaceutical compositions are generally formulated as sterile, substantially isotonic and in full compliance with all Good Manufacturing Practice (GMP) regulations of the U.S. Food and Drug Administration.

The present invention provides, inter alia, methods of inhibiting cytokine expression, e.g., IL-6 expression, in a subject for the treatment of diseases and conditions associated with increased cytokine activity. In an exemplary embodiment of the present invention, a skilled practitioner will treat a subject having a disease associated with chronic inflammation with the compounds of the present invention.

For treatment purposes, the compositions or compounds disclosed herein can be administered to the subject in a single bolus delivery, via continuous delivery (e.g., continuous transdermal, mucosal, or intravenous delivery) over an extended time period, or in a repeated administration protocol (e.g., by an hourly, daily or weekly, repeated administration protocol). The pharmaceutical formulations of the present invention can be administered, for example, one or more times daily, 3 times per week, or weekly. In an exemplary embodiment of the present invention, the pharmaceutical formulations of the present invention are orally administered once or twice daily.

In this context, a therapeutically effective dosage of the biologically active agent(s) can include repeated doses within a prolonged treatment regimen that will yield clinically significant results to alleviate one or more symptoms or detectable conditions associated with increased cytokine activity. Determination of effective dosages in this context is typically based on animal model studies followed up by human clinical trials and is guided by determining effective dosages and administration protocols that significantly reduce the occurrence or severity of targeted exposure symptoms or conditions in the subject. Suitable models in this regard include, for example, murine, rat, and other accepted animal model subjects known in the art. Alternatively, effective dosages can be determined using in vitro models. Using such models, only ordinary calculations and adjustments are typically required to determine an appropriate concentration and dose to administer a therapeutically effective amount of the biologically active agent(s) (e.g., amounts that are intranasally effective, transdermally effective, intravenously effective, or intramuscularly effective to elicit a desired response). In alternative embodiments, an "effective amount" or "therapeutically effective dose" or "pharmaceutically effective dose" of the biologically active agent(s) will simply inhibit or enhance one or more selected biological activity(ies) correlated with a disease or condition, as set forth above, for either therapeutic or diagnostic purposes.

The actual dosage of biologically active agents will of course vary according to factors such as the extent of exposure and particular status of the subject (e.g., the subject's age, size, fitness, extent of symptoms, susceptibility factors, etc), time and route of administration, as well as other drugs or treatments being administered concurrently. Dosage regimens can be adjusted to provide an optimum prophylactic or therapeutic response. By "therapeutically effective dose" or "pharmaceutically effective dose" is meant a dose that produces effects for which it is administered. More specifically, a therapeutically or pharmaceutically effective dose of the compound(s) of the invention preferably alleviates symptoms, complications, or biochemical indicia of diseases associated with increased cytokine activity. The exact dose will depend on the purpose of the treatment, and will be ascertainable by one skilled in the art using known techniques (see, e.g., Lieberman, Pharmaceutical Dosage Forms (Vols. 1-3, 1992); Lloyd, 1999, The Art, Science, and Technology of Pharmaceutical Compounding; and Pickar, 1999, Dosage Calculations). A therapeutically effective dose or pharmaceutically effective dose is also one in which any toxic or detrimental side effects of the active agent is outweighed in clinical terms by therapeutically beneficial effects. It is to be further noted that for each particular subject, specific dosage regimens should be evaluated and adjusted over time according to the individual need and professional judgment of the person administering or supervising the administration of the compounds.

In an exemplary embodiment of the present invention, unit dosage forms of the compounds are prepared for standard administration regimens. In this way, the composition can be subdivided readily into smaller doses at the physicians direction. For example, unit dosages can be made up in packeted powders, vials or ampoules and preferably in capsule or tablet form.

It is understood that the effective dosage of the active compounds of this invention can vary depending upon the particular compound utilized, the mode of administration, the condition, and severity thereof, of the condition being treated, as well as the various physical factors related to the individual being treated. For treating atherosclerosis, myocardial infarction, congestive heart failure, arthritis and/or inflammatory bowel disease, generally satisfactory results may be obtained, for example, when the compounds of this invention are administered to the individual in need at a daily dosage of from about 0.1 mg to about 1 mg per kilogram of body weight, preferably administered in divided doses two to six times per day, or in a sustained release form. For most large mammals, the total daily dosage is, for example, from about 3.5 mg to about 140 mg, preferably from about 3.5 to about 5 mg. In the case of a 70 kg human adult, the total daily dose will generally be from about 7 mg to about 70 mg and may be adjusted to provide the optimal therapeutic result.

After a pharmaceutical comprising a compound of the present invention has been formulated in a suitable carrier, it can be placed in an appropriate container and labeled for treatment of, for example, a disorder associated with chronic inflammation. Additionally, another pharmaceutical comprising at least one other therapeutic agent useful in the treatment of disorder associated with chronic inflammation can be placed in the container as well and labeled for treatment of the indicated disease. Alternatively, a single pharmaceutical comprising a compound of the present invention and at least one other therapeutic agent useful in the treatment of a disorder associated with chronic inflammation can be placed in an appropriate container and labeled for treatment. For administration of pharmaceuticals comprising compounds of the present invention and of pharmaceuticals comprising, in a single pharmaceutical, compounds of the present invention and at least one other therapeutic agent useful in the treatment of disorder associated with chronic inflammation, such labeling would include, for example, instructions concerning the amount, frequency and method of administration. Similarly, for administration of multiple pharmaceuticals provided in the container, such labeling would include, for example, instructions concerning the amount, frequency and method of administration of each pharmaceutical.

EXAMPLES

Example 1

Synthesis of 4-{[(6R)-8-fluoro-6-methylphenanthridin-5(6H)-yl]carbonyl}phenol

Step A: 8-fluoro-5-(4-methoxybenzoyl)-6-methyl-5,6-dihydrophenanthridine—A solution of 8-fluoro-6-methyl-5,6-dihydrophenanthridine (0.05 g, 0.23 mmol), 4-methoxybenzoyl chloride (0.04 g, 0.23 mmol) and 0.08 mL of diisopropylethylamine in 5 mL of THF was stirred at ambient temperature overnight. The reaction mixture was partitioned with 1N NaOH. The organic phase was washed with brine and dried ($Na_2SO_4$). The reaction mixture was purified by flash chromatography (silica gel 60, methylene chloride) to give the product as a white solid (0.05 g, 40% yield). MS (ESI) m/z 348 ([M+H]$^+$)

Step B: 4-{[(6R)-8-fluoro-6-methylphenanthridin-5(6H)-yl]carbonyl}phenol—To a solution cooled to −78° C. of 8-fluoro-5-(4-methoxybenzoyl)-6-methyl-5,6-dihydrophenanthridine (2.3 g, 6.6 mmol) in 50 mL of methylene chloride containing 2.0 mL of cyclohexene under $N_2$ atmosphere was added boron tribromide (2.9 mL, 26 mmol). The reaction was allowed to warm to ambient temperature and stir overnight. The excess boron tribromide was decomposed by the dropwise addition of methanol to the ice cooled reaction mixture. The reaction mixture was diluted with methylene chloride and partitioned with 2N HCl. The organic phase was separated and concentrated in vacuo. The residual product was purified by flash chromatography (silica gel 60, methylene chloride/ethyl acetate, 19:1) to give 1.85 g of the racemate. Isomer separated by chiral prep HPLC (Chiralcel AD, 25×5 cm, 100% EtOH, 12 mL/min) to give 0.536 g of the product as ° C., 99.86% ee); a white solid (m.p. 165 [α]$_D^{25}$= −756° (c=0.010 G/ML, MeOH); $^1$H NMR (400 MHz, DMSO-d$_6$) δ ppm 0.86 (s, 1 H) 1.19 (d, J=6.98 Hz, 3 H) 5.74 (q, J=6.73 Hz, 1 H) 6.65 (d, J=8.79 Hz, 2 H) 6.68 (d, J=8.28 Hz, 1 H) 7.05 (dt, J=7.70, 1.42 Hz, 1 H) 7.12 (d, J=8.54 Hz, 2 H) 7.18 (m, 1 H) 7.27 (td, J=8.79, 2.85 Hz, 1 H) 7.38 (dd, J=9.31, 2.85 Hz, 1 H) 7.91 (dd, J=7.76, 1.55 Hz, 1 H) 8.04 (dd, J=8.79, 5.43 Hz, 1 H) 9.96 (s, 1 H); .MS (ESI) m/z 334 ([M+H]$^+$); MS (ESI) m/z 332 ([M−H]$^-$);

Example 2

Synthesis of 3-{[(6S)-8-fluoro-6-methylphenanthridin-5(6H)-yl]carbonyl}phenol

Step A: 8-fluoro-5-(3-methoxybenzoyl)-6-methyl-5,6-dihydrophenanthridine—A solution of 8-fluoro-6-methyl-5,6-dihydrophenanthridine (0.05 g, 0.23 mmol), 3-methoxybenzoyl chloride (0.033 mL, 0.23 mmol) and 0.08 mL of diisopropylethylamine in 5 mL of THF was stirred at ambient temperature overnight. The reaction mixture was partitoned with 1N NaOH. The organic phase was washed with brine and dried ($Na_2SO_4$). The reaction mixture was purified by flash chromatography (silica gel 60, methylene chloride) to give the product as a white solid (0.045 g, 56% yield). MS (ESI) m/z 348 ([M+H]$^+$).

Step B: 3-{[(6S)-8-fluoro-6-methylphenanthridin-5(6H)-yl]carbonyl}phenol—To a solution cooled to −78° C. of 8-fluoro-5-(3-methoxybenzoyl)-6-methyl-5,6-dihydrophenanthridine (0.39 g, 1.1 mmol) in 5 mL of methylene chloride containing 0.5 mL of cyclohexene under $N_2$ atmosphere was added boron tribromide (0.495 mL, 4.48 mmol). The reaction was allowed to warm to ambient temperature and stir overnight. The excess boron tribromide was decomposed by the dropwise addition of methanol to the ice cooled reaction mixture. The reaction mixture was diluted with methylene chloride and partitioned with 2N HCl. The organic phase was separated and concentrated in vacuo. The residual product was purified by flash chromatography (silica gel 60, methylene chloride/ethyl acetate, 19:1) to give the product (0.318 g, 85% yield) as a white solid. The pure enantiomer was isolated by chiral HPLC (Xterra MS C18, ethanol/hexane 1:1) to give the product as a white solid (0.047 g, 97.6% ee). mp sinters 92, melts 138° C.; [α]$_D^{25}$=+484° (c=0.010 G/ML, MeOH); $^1$H NMR (400 MHz, DMSO-d$_6$) δ ppm 1.19 (d, J=6.73 Hz, 3 H) 5.76 (broad s, 1 H) 6.65 (d, J=9.05 Hz 2 H) 6.66 (s, 1 H) 6.79 (m, 2 H) 7.08 (m, 2 H) 7.21 (dt, 2 H) 7.28 (dt, 1 H) 7.38 (dd, 1H) 7.91 (dd, J=7.76, 1.29 Hz, 1 H) 8.04 (dd, 1 H) J=8.79, 5.43 Hz, 1 H) 9.59 (s, 1 H); MS (ESI) m/z 334 ([M+H]$^+$); MS (ESI) m/z 332 ([M−H]$^-$).

Example 3

Synthesis of 4-{[(6S)-8-fluoro-6-methylphenanthridin-5(6H)-yl]carbonyl}phenol.

Isomer separated by chiral prep HPLC from Example 1 reaction mixture (Chiralcel AD, 25×5 cm, 100% EtOH, 12 mL/min) to give 0.542 C, 99.9% ee); □g of the product as a white solid (m.p. 175 [α]$_D^{25}$=+562° (c=0.0101 G/ML, MeOH); $^1$H NMR (400 MHz, DMSO-d$_6$) δ ppm 1.19 (d, J=6.73 Hz, 3H) 5.75 (q, J=6.64 Hz, 1 H) 6.65 (d, J=9.05 Hz, 2 H) 6.68 (d, J=8.28 Hz, 1H) 7.05 (dt, J=7.70, 1.42 Hz, 1 H) 7.12 (m, J=8.79 Hz, 2H) 7.19 (dt, 2 H) 7.27 (dt, J=8.79, 2.85 Hz, 1 H) 7.91 (dd, J=7.76, 1.29 Hz, 1 H) 8.04 (dd, 1 H) J=8.79, 5.43 Hz, 1 H) 9.97 (s, 1 H) MS (ESI) m/z 334 ([M+H]$^+$); MS (ESI) m/z 332 ([M−H]$^-$).

Example 4

Synthesis of 3-{[(6R)-8-fluoro-6-methylphenanthridin-5(6H)-yl]carbonyl}phenol.

The pure enantiomer was isolated by chiral HPLC (Xterra MS C18, ethanol/hexane 1:1) to give the product as a white solid (0.20 g, 99.8% ee). mp 162° C.; [α]$_D^{25}$=−566° (c=0.010 G/ML, MeOH); $^1$H NMR (400 MHz, DMSO-d$_6$) δ ppm 1.19 (d, J=6.73 Hz, 3 H) 5.75 (broad s, 1 H) 6.65 (d, J=9.05 Hz, 2 H) 6.66 (m, 1 H) 6.79 (m, 2 H) 7.08 (m, 2 H) 7.21 (dt, 2 H) 7.28 (dt, 1 H) 7.38 (dd, 1H) 7.91 (dd, J=7.76,1.29 Hz, 1 H) 8.04 (dd, 1 H) J=8.79, 5.43 Hz, 1 H) 9.59 (s, 1 H); MS (ESI) m/z 334 ([M+H]$^+$); MS (ESI) m/z 332 ([M−H]$^-$); Anal. calcd for $C_{21}H_{16}FNO_2$.0.20 $H_2O$: C:74.85 H:4.91 N:4.16 Found: C:74.74 H:4.88 N:3.87.

Example 5

Synthesis of 3-fluoro-4-{[(6R)-8-fluoro-6-methylphenanthridin-5(6H)-yl]carbonyl}phenol Step A: 8-fluoro-5-(2-fluoro-4-methoxybenzoyl)-6-methyl-5,6-dihydrophenanthridine—A solution of 8-fluoro-6-methylphenanthridine (0.211 g, 1.0 mmol) and 2-fluoro-4- methoxybenzoyl chloride (0.253 g, 1.35 mmol) in 5 mL of methylene chloride was slowly added over 1 hour to a stirred solution of 1M borane-methyl sulfide complex 1.0 mL in methylene chloride. The reaction mixture was stirred at ambient temperature overnight. The reaction mixture was partitioned with 1N NaOH. The organic phase was washed with brine and dried ($Na_2SO_4$). The crude product was purified by flash chromatography (silica gel 60, methylene chloride) to give the product as a white solid (0.127 g, 35% of theory %) MS (ESI) m/z 366 ([M+H]$^+$).

Step B: 3-fluoro-4-{[(6R)-8-fluoro-6-methylphenanthridin-5(6H)-yl]carbonyl}phenol—To a solution cooled to −78° C. of 8-fluoro-5-(2-fluoro-4-methoxybenzoyl)-6-methyl-5,6-dihydrophenanthridine (0.111 g, 0.3 mmol) in 5 mL of methylene chloride containing 0.2 mL of cyclohexene under $N_2$ atmosphere was added boron tribromide (0.11 mL, 1.0 mmol). The reaction was allowed to warm to ambient temperature and stir overnight. The excess boron tribromide was decomposed by the dropwise addition of methanol to the ice cooled reaction mixture. The reaction mixture was diluted with methylene chloride and partitioned with 2N HCl. The organic phase was separated and concentrated in vacuo. The residual product was purified by flash chromatography (silica gel 60, methylene chloride/ethyl acetate, 19:1) to give 0.10 g of the racemate. Isomer separated by chiral prep HPLC (Pirkle Covalent (R,R) Whelk-01, 250×4.6 mm, EtOH/hexane 1:1) to give 0.038 g of the product as a white solid (99.8% ee) $[\alpha]_D^{25}=-409°$ (c=0.010 G/ML, MeOH); $^1$H NMR (400 MHz, DMSO-$d_6$) δ ppm 1.17 (d, 3 H) 5.81 (broad s, 1 H) 6.34 (broad s, 1H) 6.62 (broad d, 1H) 6.77 (broad s, 1 H) 7.07 (broad m, 1 H) 7.25 (m, 3 H) 7.38 (dd, 1 H) 7.90 (dd, 1 H) 8.04 (dd, 1 H) 10.35 (s, 1H); MS (ESI) m/z 352 ([M+H]$^+$); MS (ESI) m/z 350 ([M−H]$^-$).

Example 6

Synthesis of 3-fluoro-4-{[(6S)-8-fluoro-6-methylphenanthridin-5(6H)-yl]carbonyl}phenol Isolated in the above chiral prep as a white solid (0.035 g, 99.8% ee). $[\alpha]_D^{25}=+472°$ (c=0.0095 G/ML, MeOH); $^1$H NMR (400 MHz, DMSO-$d_6$) δ ppm 1.17 (d, 3 H) 5.8 (broad s, 1 H) 6.35 (broad s, 1 H) 6.62 (broad d, 1 H) 6.77 (broad s, 1 H) 7.07 (broad m, 1 H) 7.25 (m, 3 H) 7.38 (dd, 1 H) 7.90 (dd, 1 H) 8.04 (dd, 1 H) 10.35 (s, 1 H); MS (ESI) m/z 352 ([M+H]$^+$); MS (ESI) m/z 350 ([M−H]$^-$).

Example 7

Synthesis of 4-fluoro-3-{[(6R)-8-fluoro-6-methylphenanthridin-5(6H)-yl]carbonyl }phenol Step A: 8-fluoro-5-(2-fluoro-5-methoxybenzoyl)-6-methyl-5,6-dihydrophenanthridine—A solution of 8-fluoro-6-methylphenanthridine (0.268 g, 1.27 mmol) and 2-fluoro-5-methoxybenzoyl chloride (0.239 mg, 1.27 mmol) in 5 mL of methylene chloride was slowly added over 1 hour to a stirred solution of (S)-2-methyl-CBS-oxazaborolidine (0.11 mL, 1M solution in toluene) and borane-methyl sulfide complex (0.75 mL,1M solution in methylene chloride). The reaction mixture was stirred at ambient temperature overnight. The reaction mixture was partitioned with 1N NaOH. The organic phase was washed with brine and dried ($Na_2SO_4$). The crude product was purified by flash chromatography (silica gel 60, methylene chloride) to give the product as a white solid (0.250 g, 65% of theory, e.e.=37.6% of the R isomer); MS (ESI) n/z 366 ([M+H]$^+$).

Step B: 4-fluoro-3-{[(6R)-8-fluoro-6-methylphenanthridin-5(6H)-yl]carbonyl}phenol—To a solution cooled to −78° C. of 8-fluoro-5-(2-fluoro-5-methoxybenzoyl)-6-methyl-5,6-dihydrophenanthridine (0.206 g, 0.57 mmol) in 5 mL of methylene chloride containing 0.5 mL of cyclohexene under $N_2$ atmosphere was added boron tribromide (0.25 mL, 2.25 mmol). The reaction was allowed to warm to ambient temperature and stir overnight. The excess boron tribromide was decomposed by the dropwise addition of methanol to the ice cooled reaction mixture. The reaction mixture was diluted with methylene chloride and partitioned with 2N HCl. The organic phase was separated and concentrated in vacuo. The residual product was purified by flash chromatography ( silica gel 60, methylene chloride/ethyl acetate, 19:1) to give 0.27 g, of intermediate. The chirally pure enantiomer was isolated by chiral HPLC (Chiralpak AD, 4.6×250 mm, ethanol/hexane 1:1) to give the product as a white solid (0.092 g, 99.94% ee). $[\alpha]_D^{25}=-604°$ (c=0.010 G/ML, MeOH); $^1$H NMR (400 MHz, DMSO-$d_6$) δ 1.09 (s, 1 H) 1.18 (d, J=6.72 Hz, 3 H) 3.38 (s, 1 H) 6.77 (s, 1 H) 7.05 (s, 1 H) 7.26 (td, J=8.77, 2.59 Hz, 4 H) 7.40 (s, 2 H) 7.92 (d, J=7.49 Hz, 1 H) 8.02 (dd, J=8.79, 5.43 Hz, 1 H) 9.62 (br. s, 1 H); MS (ESI) m/z 352 ([M+H]$^+$); MS (ESI) m/z 350 ([M−H]$^-$).

Example 8

Synthesis of 4-fluoro-3-{[(6S)-8-fluoro-6-methylphenanthridin-5(6H)-yl]carbonyl}phenol.

Isolated in the above chiral prep (0.033 g, 99.6% ee); $[\alpha]_D^{25}=+594°$ (c=0.0101 G/ML, MeOH); $^1$H NMR (400 MHz, DMSO-$d_6$) δ:1.09 (s, 1 H) 1.18 (d, J=6.73 Hz, 3H) 3.38 (s, 1 H) 6.77 (s, 1 H) 7.05 (s, 1 H) 7.26 (td, J=8.79, 2.59 Hz, 4 H) 7.40 (s, 2 H) 7.92 (d, J=7.50 Hz, 1 H) 8.02 (dd, J=8.79, 5.43 Hz, 1 H) 9.62 (br. s, 1 H); MS (ESI) m/z 352 ([M+H]$^+$); MS (ESI) m/z 350 ([M−H]$^-$).

Example 9

Synthesis of 2-fluoro-4-{[(6R)-8-fluoro-6-methylphenanthridin-5(6H)-yl]carbonyl}phenol Step A: 8-fluoro-5-(3-fluoro-4-methoxybenzoyl)-6-methyl-5,6-dihydrophenanthridine—A solution of 8-fluoro-6-methylphenanthridine (0.268 g, 1.27 mmol) and 3-fluoro-4-methoxybenzoyl chloride (0.239 g, 1.27 mmol) in 5 mL of methylene chloride was slowly added over 1 hour to a stirred solution of (S)-2-methyl-CBS-oxazaborolidine (0.20 mL, 1M solution in toluene) and borane-methyl sulfide complex (0.75 mL,1M solution in methylene chloride). The reaction mixture was stirred at ambient temperature overnight. The reaction mixture was partitioned with 1N NaOH. The organic phase was washed with brine and dried ($Na_2SO_4$). The crude product was purified by flash chromatography (silica gel 60, methylene chloride) to give the product as a white solid (0.209 g, 57% of theory). MS (ESI) m/z 366 ([M+H]$^+$).

Step B: 2-fluoro-4-{[(6R)-8-fluoro-6-methylphenanthridin-5(6H)-yl]carbonyl}phenol—To a solution cooled to −78° C. of 8-fluoro-5-(3-fluoro-4-methoxybenzoyl)-6-methyl-5,6-dihydrophenanthridine (0.191 g, 0.52 mmol) in 5 mL of methylene chloride containing 0.2 mL of cyclohexene under $N_2$ atmosphere was added boron tribromide (0.231 mL, 2.09 mmol). The reaction was allowed to warm to ambient temperature and stir overnight. The excess boron tribromide was decomposed by the dropwise addition of methanol to the ice cooled reaction mixture. The reaction mixture was diluted with methylene chloride and partitioned with 2N HCl. The organic phase was separated and concentrated in vacuo. The residual product was purified by flash chromatography (silica gel 60, methylene chloride/ethyl acetate, 19:1) to give the product mixture (0.174 g). The chirally pure enantiomer was isolated by chiral HPLC (Chiralpak AD, 4.6×250 mm, ethanol/hexane 1:1) to give the product as a white solid (0.077 g, 99.8% ee). $[\alpha]_D^{25}=-676°$ (c=0.010 G/ML, MeOH); $^1$H NMR (400 MHz, DMSO-d$_6$) δ ppm 1.19 (d, J=6.92 Hz, 3 H) 5.74 (q, J=6.83 Hz, 1 H) 6.73 (d, J=7.69 Hz, 1 H) 6.84 (m, 2 H) 7.08 (m, 2H) 7.22 (dt, J=7.62, 1.15 Hz, 1 H) 7.27 (dt, 1 H) 7.39 (dd, J=9.22, 2.56 Hz, 1 H) 7.93 (dd, J=7.81, 1.41 Hz, 1 H) 8.05 (dd, J=8.71, 5.38 Hz, 1 H); MS (ESI) m/z 352 ([M+H]$^+$); MS (ESI) m/z 350 ([M−H]$^-$).

Example 10

Synthesis of 2-fluoro-4-{[(6S)-8-fluoro-6-methylphenanthridin-5(6H)-yl]carbonyl}phenol.

Isolated in the above chiral prep (0.027 g, 99.8% ee). $^1$H NMR (400 MHz, DMSO-d$_6$) δ ppm 0.84 (s, 1 H) 1.19 (d, J=6.92 Hz, 3 H) 5.73 (q, J=6.66 Hz, 1 H 6.76 (m, 2 H) 6.85 (m, 1 H) 7.07 (m, 2 H) 7.21 (dt, J=7.56, 1.02 Hz, 1 H) 7.27 (dt, J=8.84, 2.82 Hz, 1 H) 7.38 (dd, J=9.22, 2.82 Hz, 1 H) 7.93 (dd, J=7.81, 1.15 Hz, 1 H) 8.05 (dd, J=8.71, 5.64 Hz, 1 H); MS (ESI) m/z 352 ([M+H]$^+$); MS (ESI) m/z 350 ([M−H]$^-$).

Example 11

Synthesis of 2-chloro-5-{[(6R)-8-fluoro-6-methylphenanthridin-5(6H)-yl]carbonyl}phenol Step A: 5-(4-chloro-3-methoxybenzoyl)-8-fluoro-6-methyl-5,6-dihydrophenanthridine—A solution of 8-fluoro-6-methylphenanthridine (0.211 g, 1.0 mmol) and 4-chloro-3-methoxybenzoyl chloride (0.205 g, 1.0 mmol) in 5 mL of methylene chloride was slowly added over 1 hour to a stirred solution of (S)-2-methyl-CBS-oxazaborolidine (0.2 mL, 1M solution in toluene) and borane-methyl sulfide complex (0.7 mL,1M solution in methylene chloride). The reaction mixture was stirred at ambient temperature overnight. The reaction mixture was partitioned with 1N NaOH. The organic phase was washed with brine and dried (Na$_2$SO$_4$). The crude product was purified by flash chromatography (silica gel 60, methylene chloride) to give the product as a white solid (0.087 g, 29% of theory); MS (ESI) m/z 382/384 ([M+H]$^+$).

Step B: 2-chloro-5-{[(6R)-8-fluoro-6-methylphenanthridin-5(6H)-yl]carbonyl}phenol—To a solution cooled to −78° C. of 8-fluoro-5-(4-chloro-3-methoxybenzoyl)-6-methyl-5,6-dihydrophenanthridine (0.076 g, 0.2 mmol) in 5 mL of methylene chloride containing 0.5 mL of cyclohexene under N$_2$ atmosphere was added boron tribromide (0.088 mL, 0.8 mmol). The reaction was allowed to warm to ambient temperature and stir overnight. The excess boron tribromide was decomposed by the dropwise addition of methanol to the ice cooled reaction mixture. The reaction mixture was diluted with methylene chloride and partitioned with 2N HCl. The organic phase was separated and concentrated in vacuo. The residual product was purified by flash chromatography (silica gel 60, methylene chloride/ethyl acetate, 19:1) to give the product mixture (0.70 g). The pure enantiomer was isolated by chiral HPLC (Chiralpak AD, 4.6×250 mm, acetonitrile/ethanol, 9:1) to give the product as a white solid (0.015 g, 99.8% ee).

$^1$H NMR (400 MHz, DMSO-d$_6$) δ ppm 1.19 (d, 3 H) 5.74 (broad s, 1 H) 6.65 (broad d, 1 H) 6.77 (broad s, 1 H) 6.91 (s, 1H) 7.23 (t, 1 H) 7.5 (m, 3 H)) 7.39 (dd, 1 H) 7.93 (dd, 1 H) 8.05 (dd,1 H) 10.42 (s, 1H); MS (ESI) m/z 368/370 ([M+H]$^+$); MS (ESI) m/z 366/368 ([M−H]$^-$).

Example 12

Synthesis of 2-chloro-5-{[(6S)-8-fluoro-6-methylphenanthridin-5(6H)-yl]carbonyl}phenol.

Isolated from the above chiral prep to give 0.02 g (99.8% ee) of the pure enantiomer. $[\alpha]_D^{25}=+577°$ (c=0.0082 G/ML, MeOH); MS (ESI) m/z 368/370 ([M+H]$^+$); MS (ESI) m/z 366/368 ([M−H]$^-$).

Example 13

Synthesis of 2-bromo-4-{[(6R)-8-fluoro-6-methylphenanthridin-5(6H)-yl]carbonyl}phenol.

Step A: 5-(3-bromo-4-methoxybenzoyl)-8-fluoro-6-methyl-5,6-dihydrophenanthridine—A solution of 8-fluoro-6-methylphenanthridine (0.211 g, 1.0 mmol) and 3-bromo-4-methoxybenzoyl chloride (0.249 g, 1.0 mmol) in 5 mL of methylene chloride was slowly added over 1 hour to a stirred solution of (S)-2-methyl-CBS-oxazaborolidine (0.2 mL, 1M solution in toluene) and borane-methyl sulfide complex (0.7 mL,1M solution in methylene chloride). The reaction mixture was stirred at ambient temperature overnight. The reaction mixture was partitioned with 1N NaOH. The organic phase was washed with brine and dried (Na$_2$SO$_4$). The crude product was purified by flash chromatography (silica gel 60, methylene chloride) to give the product as a white solid (0.180 g, 42% of theory); MS (ESI) m/z 426/428 ([M+H]$^+$).

Step B: 2-bromo-4-{[(6R)-8-fluoro-6-methylphenanthridin-5(6H)-yl]carbonyl}phenol—To a solution cooled to −78° C. of 8-fluoro-5-(3-bromo-4-methoxybenzoyl)-6-methyl-5,6-dihydrophenanthridine (0.175 g, 0.41 mmol) in 5 mL of methylene chloride containing 0.1 mL of cyclohexene under N$_2$ atmosphere was added boron tribromide (0.181 mL, 1.63 mmol). The reaction was allowed to warm to ambient temperature and stir overnight. The excess boron tribromide was decomposed by the dropwise addition of methanol to the ice cooled reaction mixture. The reaction mixture was diluted with methylene chloride and partitioned with 2N HCl. The organic phase was separated and concentrated in vacuo. The residual product was purified by flash chromatography (silica gel 60, methylene chloride/ethyl acetate, 19:1) to give the product mixture (0.160 g). The chirally pure enantiomer was isolated by chiral HPLC (Chiralpak AD, 4.6×250 mm, acetonitrile/ethanol, 9:1) to give the product as a white solid (0.041 g, 99.98% ee). $^1$H NMR (400 MHz, DMSO-d$_6$) δ ppm 1.19 (d, 3H) 5.74 (m, 1H) 6.74 (d, 1 H) 6.77 (d, 1 H) 7.01 (dd, 1H) 7.21 dt, 1 H) 7.25 (m, 3 H) 7.39 (dd, 1H) 7.42 (d, 1H) 7.93 (dd, 1 H) 8.05 (dd,1 H) 10.90 (s, 1H); MS (ESI) m/z 412/414 ([M+H]$^+$); MS (ESI) m/z 410/412 ([M−H]$^-$).

Example 14

Synthesis of 2-bromo-4-{[(6S)-8-fluoro-6-methylphenanthridin-5(6H)-yl]carbonyl}phenol.

Isolated from the above chiral prep to give 0.049 g (99.8% ee) of the title compound. $[\alpha]_D^{25}=+533°$ (c=0.0104 G/ML, MeOH); $^1$H NMR (400 MHz, DMSO-d$_6$) δ ppm 1.19 (d, 3 H) 5.74 (m, 1 H) 6.74 (d, 1 H) 6.77 (d, 1 H) 7.01 (dd, 1H) 7.22 dt, 1 H) 7.25 (m, 3 H) 7.39 (dd, 1H) 7.43 (d, 1H) 7.93 (dd, 1 H) 8.05 (dd,1 H) 10.89 (s, 1H); MS (ESI) m/z 412/414 ([M+H]$^+$); MS (ESI) m/z 410/412 ([M−H]$^-$).

Example 15

Synthesis of 4-bromo-3-{[(6R)-8-fluoro-6-methylphenanthridin-5(6H)-yl]carbonyl}phenol.

Step A: 5-(2-bromo-5-methoxybenzoyl)-8-fluoro-6-methyl-5,6-dihydrophenanthridine—A solution of 8-fluoro-6-methylphenanthridine (0.211 g, 1.0 mmol) and 2-bromo-5-methoxybenzoyl chloride (0.231 g, 1.0 mmol) in 5 mL of methylene chloride was slowly added over 1 hour to a stirred solution of (S)-2-methyl-CBS-oxazaborolidine (0.2 mL, 1M solution in toluene) and borane-methyl sulfide complex (0.7 mL, 1M solution in methylene chloride). The reaction mixture was stirred at ambient temperature overnight. The reaction mixture was partitioned with 1N NaOH. The organic phase was washed with brine and dried ($Na_2SO_4$). The crude product was purified by flash chromatography (silica gel 60, methylene chloride) to give the product as a white solid (0.258 g, 60% of theory); MS (ESI) m/z 426/428 ([M+H]$^+$).

Step B: 4-bromo-3-{[(6R)-8-fluoro-6-methylphenanthridin-5(6H)-yl]carbonyl}phenol—To a solution cooled to −78° C. of 8-fluoro-5-(2-bromo-5-methoxybenzoyl)-6-methyl-5,6-dihydrophenanthridine (0.243 g, 0.57 mmol) in 5 mL of methylene chloride containing 0.2 mL of cyclohexene under $N_2$ atmosphere was added boron tribromide (0.252 mL, 2.28 mmol). The reaction was allowed to warm to ambient temperature and stir overnight. The excess boron tribromide was decomposed by the dropwise addition of methanol to the ice cooled reaction mixture. The reaction mixture was diluted with methylene chloride and partitioned with 2N HCl. The organic phase was separated and concentrated in vacuo. The residual product was purified by flash chromatography (silica gel 60, methylene chloride/ethyl acetate, 19:1) to give the product mixture (0.210 g). The pure enantiomer was isolated by chiral HPLC (Whelk-01 (S,S), ethanol/hexane 1:1) to give the product as a white solid (0.080 g, 99.8% ee). $^1$H NMR (400 MHz, DMSO-$d_6$) δ ppm 1.19 (d, J=6.98 Hz, 3 H) 6.06 (d, J=5.69 Hz, 1 H) 6.70 (m, 2 H) 6.85 (dd, 1 H) 7.03 (m, 1 H) 7.22 (m, 2 H) 7.44 (m, 2 H) 7.88 (d, J=7.76 Hz, 1H) 7.99 (m, 2 H) 10.03 (s, 1 H) MS (ESI) m/z 412/414 ([M+H]$^+$); MS (ESI) m/z 410/412 ([M−H]$^-$).

Example 16

Synthesis of 4-bromo-3-{[(6S)-8-fluoro-6-methylphenanthridin-5(6H)-yl]carbonyl}phenol.

Isolated in the above chiral prep to give 0.055 g (98.6% ee) of the title compound. $[α]_D^{25}$=+476° (c=0.0104 G/ML, MeOH); MS (ESI) m/z 412/414 ([M+H]$^+$); MS (ESI) m/z 410/412 ([M−H]$^-$).

Example 17

Synthesis of 4-{[(6R)-8-fluoro-6-methylphenanthridin-5(6H)-yl]carbonyl}-2-methoxyphenol.

A solution of 8-fluoro-6-methylphenanthridine (0.211 g, 1.0 mmol) and 3-methoxy-4-hydroxybenzoyl chloride (0.168 g, 1.0 mmol) in 5 mL of methylene chloride was slowly added over 1 hour to a stirred solution of (S)-2-methyl-CBS-oxazaborolidine (0.2 mL, 1M solution in toluene) and borane-methyl sulfide complex (0.7 mL, 1M solution in methylene chloride). The reaction mixture was stirred at ambient temperature overnight. The reaction mixture was partitioned with 1N NaOH. The organic phase was washed with brine and dried ($Na_2SO_4$). The crude product was purified by flash chromatography (silica gel 60, methylene chloride) to give the product mixture (0.053 g). The pure enantiomer was isolated by chiral HPLC (AD, acetonitrile/ethanol, 9:1) to give the product as a white solid (0.033 g, 99.8% ee). $^1$H NMR (400 MHz, DMSO-$d_6$) δ ppm 1.20 (d, J=6.98 Hz, 3 H) 3.61 (s, 3 H) 5.76 (q, J=6.64 Hz, 1 H) 6.64 (m, 2 H) 6.71 (d, J=8.28 Hz, 1 H) 6.89 (d, J=1.03 Hz, 1 H) 7.06 (td, J=7.70, 1.42 Hz, 1 H) 7.20 (td, J=7.57, 1.16 Hz, 1 H) 7.26 (td, J=8.79, 2.85 Hz, 1 H) 7.39 (dd, J=9.31, 2.85 Hz, 1 H) 7.92 (dd, J=8.02, 1.29 Hz, 1 H) 8.05 (dd, J=8.67, 5.56 Hz, 1 H); MS (ESI) m/z 364 ([M+H]$^+$); MS (ESI) m/z 362 ([M−H]$^-$).

Example 18

Synthesis of 4-{[(6S)-8-fluoro-6-methylphenanthridin-5(6H)-yl]carbonyl}-2-methoxyphenol Isolated from the above chiral prep to give 0.02 g (98.6% ee) of the title compound. $[α]_D^{25}$=+493° (c=0.008 G/ML, MeOH); $_1$H NMR (400 MHz, DMSO-$d_6$) δ ppm 1.19 (d, J=6.73 Hz, 3 H) 3.61 (s, 3 H) 5.76 (q, J=6.64 Hz, 1 H) 6.64 (m, 2 H) 6.71 (d, J=8.02 Hz, 1 H) 6.88 (d, J=1.03 Hz, 1 H) 7.06 (td, J=7.70, 1.42 Hz, 1 H) 7.20 (td, J=7.57, 1.16 Hz, 1 H) 7.26 (td, J=8.79, 2.85 Hz, 1 H) 7.39 (dd, J=9.31, 2.85 Hz, 1 H) 7.92 (dd, J=7.89, 1.42 Hz, 1 H) 8.05 (dd, J=8.79, 5.43 Hz, 1 H) 9.63 (s, 1 H); MS (ESI) m/z 364 ([M+H]$^+$); MS (ESI) m/z 362 ([M−H]$^-$).

Example 19

Synthesis of 4-{[(6S)-6-ethyl-8-fluorophenanthridin-5(6H)-yl]carbonyl}phenol

Step A: 6-Ethyl-8-methyl-phenanthridine—To cold (dry ice/acetone) ethylmagnesium bromide (20 mL of 1.0 M in THF) was added a mixture of 4,2'-difluoro-biphenyl-2-carbonitrile (4.6 mmol, 1.0 g) in 10 mL of THF, dropwise (15 min.). Stirring was continued overnight, and the reaction mixture was diluted with 10% ammonium chloride and ethyl acetate. The organic portion was washed with water and brine and dried over magnesium sulfate. The solvent was removed and the crude product flashed (dichloromethane) giving a white solid: mp 74-75° C. (0.44 g, 52%); MS m/z 216 ([M+H]$^+$).

Step B: 6-ethyl-8-fluoro-5-(4-methoxybenzoyl)-5,6-dihydrophenanthridine—To a mixture of borane methyl sulfide complex (2.5 mL of 1 M solution in dichloromethane), S-2-Methyl-CBS-oxazaborolidine (1 ML of 1 M solution in toluene) and anhydrous dichloromethane (25 mL) was added a solution of 6-Ethyl-8-methyl-phenanthridine (0.906 g, 5 mmol) and 4-Methoxybenzoyl chloride (0.938 g, 5.5 mmol) in dichloromethane (10 mL), dropwise. The reaction mixture was stirred at room temperature overnight. Sodium hydroxide (10 mL of 2 N solution) was added, the organic portion dried over anhydrous magnesium sulfate and the solvent removed to provide a dark liquid. The crude material was purified by flash chromatography (dichloromethane) to afford a white solid (0.95 g, 52%): mp 71-72° C.; MS m/z 362 ([M+H]$^+$).

Step C: 4-{[(6S)-6-ethyl-8-fluorophenanthridin-5(6H)-yl]carbonyl}phenol—To a mixture of neat boron tribromide (1.2 mL) and cyclohexene (2 mL) in anhydrous dichloromethane (20 mL) cooled with dry ice/isopropanol was added a mixture of 6-ethyl-8-fluoro-5-(4-methoxybenzoyl)-5,6-dihydrophenanthridine (0.90 g, 2.5 mmol) in dichloromethane (10 mL), dropwise (20 min.) The reaction mixture was stirred overnight as the temperature rose to room temperature. The excess boron tribromide was decomposed by adding a small quantity of methanol, followed by 2 N HCl (5 mL). The organic portion was dried over anhydrous magnesium sulfate, the solvent was removed and the crude product was purified by chromatography (5% ethyl acetate-dichloromethane) to afford a tan solid (0.583 g), The compound was purified by chiral HPLC to give 0.220 g of title compound. mp 103-104° C.; $^1$H NMR (DMSO-d$_6$): δ 0.86 (3 H, t, J=7.4 Hz), 1.33-1.43 (1H, m), 1.45-1.54 (1H, m), 5.57-5.61 (1 m), 6.62 (2 H, d, J=8.8 Hz), 6.68 (1H, d, J=8.0 Hz), 7.04-7.08(3 H, m), 7.17-7.21 (1 H, m), 7.25-7.30 (1 H, m), 7.38 (1 H, dd, J=9.3 Hz, J=2.7 Hz), 7.91 (1H, dd, J=7.8 Hz, J=1.2 Hz), 8.04 (1H, dd, J=8.7 Hz, J=5.5 Hz), 9.92 (1H, br s); MS m/z 348 ([M+H]$^+$).

Example 20

Synthesis of 4-{[(6R)-6-ethyl-8-fluorophenanthridin-5(6H)-yl]carbonyl}phenol

The minor isomer was also isolated in the above separation. (0.100 g): mp 105-106; $^1$H NMR (DMSO-d$_6$): δ 0.86 (3 H, t, J=7.4 Hz), 1.33-1.43 (1 H, m), 1.45-1.55 (1 H, m), 5.57-5.61 (1 H, m), 6.62 (2 H, d, J=8.8 Hz), 6.68 (1 H, d, J=7.9 Hz 7.04-7.09 (3 H, m), 7.17-7.21 (1 H, m), 7.25-7.30 (1 H, m), 7.38 (1 H, dd, J=9.2 Hz, J=2.7 Hz), 7.91 (1 H, dd, J=7.9 Hz, J=1.3 Hz), 8.04 (1 H, dd, J=8.7 Hz, J=5.5 Hz), 9.92 (1 H, br s); MS m/z 348 ([M+H]+).

Example 21

Synthesis of 3-{[(6R)-6-ethyl-8-fluorophenanthridin-5(6H)-yl]carbonyl}phenol

To a mixture of borane methyl sulfide complex (0.6 mL of 1 M solution in dichloromethane), S-2-Methyl-CBS-oxazaborolidine (0.2 mL of 1 M solution in toluene) and anhydrous dichloromethane (5 mL) was added a solution of 6-Ethyl-8-methyl-phenanthridine (0.225 g, 1 mmol) and 3-methoxybenzoyl chloride (0.188 g, 1.1 mmol) in dichloromethane (5 mL), dropwise. The reaction mixture was stirred at room temperature overnight. Sodium hydroxide (10 mL of 2 N solution) was added, the organic portion dried over anhydrous magnesium sulfate and the solvent removed to provide a dark liquid. The crude material was purified by chromatography (dichloromethane) to afford a white solid (0.08 g, 22%). The material was taken forward without getting analyses. To a mixture of neat boron tribromide (0.2 mL) and cyclohexene (0.2 mL) in anhydrous dichloromethane (10 mL) cooled with dry ice/isopropanol was added a mixture the methoxy derivative above 0.080 g, 0.2 mmol) in dichloromethane (10 mL), dropwise (20 min.) The reaction mixture was stirred overnight as the temperature rose to room temperature. The excess boron tribromide was decomposed by adding a small quantity of methanol, follwed by 2 N HCl (5 mL). The organic portion was dried over anhydrous magnesium sulfate, the solvent was removed and the crude product was purified by chromatography (5% ethyl acetate-dichloromethane) to afford a solid (0.045g), which was purified by chiral HPLC to give the major isomer: 0.030 g: mp 101-102; $_1$H NMR (DMSO-d$_6$): δ 0.86 (3 H, t, J=7.3 Hz), 1.31-1.42 (1 H, m), 1.46-1.54 (1 H, m), 5.59 (1 H, br s), 6.56 (1 H, d, J=7.4 Hz), 6.61 (1 H, s), 6.76 (2H, dd, J=8.1 Hz, J=1.7 Hz), 7.04-7.09 (2 H, m), 7.19-7.23 (1 H, m), 7.26-7.31 (1 H, m), 7.36-7.39 (1 H, m), 7.92 (1 H, dd, J=7.9 Hz, J=1.2 Hz), 8.06 (1 H, dd, J=8.7 Hz, J=5.5 Hz), 9.56 (1 H, s); MS m/z 348 ([M+H]+).

Example 22

Synthesis of 4-{[(6R)-6-ethyl-8-fluorophenanthridin-5(6H)-yl]carbonyl}benzene-1,3-diol Step A: 5-(2,4-dimethoxybenzoyl)-6-ethyl-8-fluoro-5,6-dihydrophenanthridine—To a mixture of borane methyl sulfide complex (0.6 mL of 1 M solution in dichloromethane), S-2-Methyl-CBS-oxazaborolidine (0.2 mL of 1 M solution in toluene) and anhydrous dichloromethane (5 mL) was added a solution of 6-Ethyl-8-methyl-phenanthridine (0.225 g, 1 mmol) and 2,4-dimethoxybenzoyl chloride (0.221 g, 1.1 mmoles) in dichloromethane (5 mL), dropwise. The reaction mixture was stirred at room temperature overnight. Sodium hydroxide (10 mL of 2 N solution) was added, the organic portion dried over anhydrous magnesium sulfate and the solvent removed to provide a dark liquid. The crude material was purified by chromatography (dichloromethane) to afford a white solid (0.18 g, 32%): mp 125-126° C.; MS (ESI) m/z 392 ([M+H]$^+$).

Step B: 4-{[(6R)-6-ethyl-8-fluorophenanthridin-5(6H)-yl]carbonyl}benzene-1,3-diol—To a mixture of neat boron tribromide (0.2 mL) and cyclohexene (0.2 mL) in anhydrous dichloromethane (10 mL) cooled with dry ice/isopropanol was added a solution of 5-(2,4-dimethoxybenzoyl)-6-ethyl-8-fluoro-5,6-dihydrophenanthridine (0.080 g, 0.2 mmol) in dichloromethane (10 mL), dropwise (20 min.) The reaction mixture was stirred overnight as the temperature rose to room temperature. The excess boron tribromide was decomposed by adding a small quantity of methanol, then 2 N HCl was added (5 mL). The organic portion was dried over anhydrous magnesium sulfate, the solvent was removed and the crude product was purified by chromatography (5% ethyl acetate-dichloromethane) to afford a solid (0.05 g), which was submitted for chromatographic separation of the isomers. The major isomer: 0.012 g: mp 98-100; $^1$H NMR (DMSO-d$_6$): δ 0.84 (3 H, t, J=7.3 Hz), 1.34-1.41 (1 H, m), 1.49-1.56 (1 H, m), 5.55 (1 H, br s), 6.10 (1 H, d, J=1.9 Hz), 6.14 (1 H, dd, J=8.4 Hz, J=2.2 Hz), 6.85 (1 H, d, J=8.3 Hz), 7.05 (1 H, t, J=7.4 Hz), 7.15-7.19 (1 H, m), 7.21-7.26 (1 H, m), 7.31-7.33 (2 H, m), 7.85 (1 H, dd, J=7.8 Hz, J=1.3 Hz), 7.96 (1H, dd, J=8.7Hz, J=5.5 Hz), 9.53 (1 H, s), 9.61 (1 H, s); MS m/z 364 ([M+H]+).

Example 23

Synthesis of 4-[(6-ethyl-8-fluorophenanthridin-5(6H)-yl)carbonyl]-3-fluorophenol Step A: 6-ethyl-8-fluoro-5-(2-fluoro-4-methoxybenzoyl)-5,6-dihydrophenanthridine—To a mixture of borane methyl sulfide complex (0.5 mL of 1 M solution in dichloromethane), S-2-Methyl-CBS-oxazaborolidine (0.2 mL of 1 M solution in toluene) and anhydrous dichloromethane (5 mL) was added a solution of 6-Ethyl-8-methyl-phenanthridine (0.225 g, 1 mmol) and 2-fluoro-4-methoxybenzoyl chloride (0.20 g, 1.1 mmol) in dichloromethane (5 mL), dropwise. The reaction mixture was stirred at room temperature overnight. Sodium hydroxide (10 mL of 2 N solution) was added, the organic portion dried over anhydrous magnesium sulfate and the solvent removed to provide a dark liquid. The crude material was purified by chromatography (dichloromethane) to afford a white solid (0.13 g, 33%): MS (ESI) m/z 380 ([M+H]$^+$);

Step B 4-[(6-ethyl-8-fluorophenanthridin-5(6H)-yl)carbonyl]-3-fluorophenol—To a mixture of neat boron tribromide (0.1 mL) and cyclohexene (0.2 mL) in anhydrous dichloromethane (10 mL) cooled with dry ice/isopropanol was added a solution of 6-ethyl-8-fluoro-5-(2-fluoro-4-methoxybenzoyl)-5,6-dihydrophenanthridine (0.120 g, 0.3 mmol) in dichloromethane (10 mL), dropwise (20 min.) The reaction mixture was stirred overnight as the temperature rose to room temperature. The excess boron tribromide was decomposed by adding a small quantity of methanol, then 2 N HCl was added (5 mL). The organic portion was dried over anhydrous magnesium sulfate, the solvent was removed and the crude product was purified by chromatography (10% ethyl acetate-dichloromethane) to afford a solid (0.045 g): mp 109-111° C.; $^1$H NMR (DMSO-$d_6$): δ 0.86 (3 H, t, J=7.2 Hz), 1.27-1.35 (1 H, m), 1.48-1.54 (1 H, m), 5.69 (1 H, br s), 6.33 (1 H, br s), 6.60 (1 H, d, J=6.7 Hz), 7.06 (1 H, br s), 7.19-7.28 (2 H, m), 7.38 (1H, d, J=8.0 Hz), 7.89 (1 H, d, J=7.0 Hz), 8.01 (1 H, dd, J=8.5 Hz, J=5.3 Hz), 10.32 (1 H, br s); MS m/z 366 ([M+H]+).

Example 24

Synthesis of 3-[(3-chloro-6-methylphenanthridin-5 (6H)-yl)carbonyl]phenol

Step A: 1-(4'-chloro-2'-fluoro-1,1'-biphenyl-2-yl)ethanone-2—Acetylphenyl boronic acid (5 g, 30.5 mmol) and 4-chloro-2-fluoroiodobenzene (8.6 g, 33.5 mmol) were dissolved in toluene/ethanol mixture (6:1, 175 mL). An aqueous solution of potassium carbonate (2M, 60 mL) and tetrakis (triphenylphosphine)palladium (0) (1.06 g, 0.91 mmol) were added to the solution and the entire mixture was degassed using vacuum and stirring with intermittent nitrogen purge. The mixture was heated (85° C.) with stirring for 14 h. The mixture was allowed to cool and then water was added. The organic phase was separated from the aqueous phase and the aqueous phase was extracted with ethyl acetate (3×100 mL). The organic phases were combined, dried ($Na_2SO_4$), filtered, and concentrated to a crude oil. The product was isolated via flash column chromatography (Biotage® 40 Mi, 5-20%, methyl tert-butylether in hexane) and afforded 4.07 g (54%) of the desired product as a yellow oil. MS (EI) m/z 248.0/ 250.0 (M+.);

$^1$H NMR (400 MHz, DMSO-$d_6$) δ ppm 2.45 (s, 3 H) 7.37 (m, 3 H) 7.44 (m, 1 H) 7.57 (td, J=7.63, 1.29 Hz, 1 H) 7.65 (td, J=7.57, 1.42 Hz, 1 H) 7.90 (ddd, J=7.63, 1.42, 0.52 Hz, 1 H)

Step B: 1-(4'-Chloro-2'-fluoro-biphenyl-2-yl)-ethylamine—To a stirred solution of 1-(4'-Chloro-2'-fluoro-biphenyl-2-yl)-ethanone (3.2 g, 12.9 mmol) in anhydrous methanol (200 mL) was added solid ammonium acetate (19.8 g, 257 mmol). The reaction mixture was heated (60° C., 1 h) followed by the addition of a methanolic solution of sodium cyanoborohydride (1.62 g, 25.8 mmol). After 16 h, the methanol was removed in vacuo and aqueous ammonium hydroxide was added. The aqueous phase was extracted with diethyl ether (3×200 mL) until the amine was no longer present in the aqueous phase. The organic phase was then washed with 2N aqueous HCl (3×100 mL) and the aqueous phases combined. The solid formed during the acid wash was determined to be the dialkyated amine and was segregated from the aqueous phase. Aqueous sodium hydroxide was then added to the acidic aqueous phase until the solution was basic (pH 8-9). The basic aqueous phase was extracted with diethyl ether until the primary amine was no longer detected in the aqueous phase. The combined organic phases were dried ($Na_2SO_4$), filtered, and concentrated to afford a clear oil that was used without further purification. MS [(ES+), m/z]: 233 [M-16]$^+$, benzylic cation as a result of loss of $NH_2$;

Step C: N-[1-(4'-chloro-2'-fluoro-1,1'-biphenyl-2-yl) ethyl]-3-methoxybenzamide—To a solution of 1-(4'-Chloro-2'-fluoro-biphenyl-2-yl)-ethylamine (1 g, 4 mmol) and triethylamine (614 uL, 4.4 mmol) in acetonitrile was added 3-methoxybenzoyl chloride (683 mg, 4 mmol). The reaction was mixed overnight (16 h) on an orbital mixer at room temperature. The acetonitrile was removed in vacuo and the resulting solid dissolved in dichloromethane and applied directly to a Biotage® (40 Mi) column for flash column chromatography (5-30% methyl tert-butylether in hexane) resulting in the isolation of 1.22 g (79%) of a white solid. mp 176.2-177.9° C.; $^1$H NMR (400 MHz, DMSO-$d_6$) δ ppm 1.31 (d, J=5.69 Hz, 3 H) 3.79 (s, 3 H) 4.96 (m, 1 H) 7.07 (dd, J=8.02, 1.81 Hz, 1 H) 7.16 (d, J=7.24 Hz, 1 H) 7.36 (m, 7 H) 7.60 (m, 2 H) 8.80 (s, 1 H); MS (ESI) m/z 384/386 ([M+H]$^+$); Anal. calcd for $C_{22}H_{19}ClFNO_2$: C:68.84 H:4.99 N:3.65 Found: C:68.88 H:5.25 N:3.64.

Step D: 3-chloro-5-(3-methoxybenzoyl)-6-methyl-5,6-dihydrophenanthridine—N-[1-(4'-Chloro-2'-fluoro-biphenyl-2-yl)-ethyl]-3-methoxy-benzamide (1.04 g, 2.7 mmol) was dissolved in anhydrous THF (10 mL) and the vial was capped and purged with an inert atmosphere. Lithium bis(trimethylsilyl)amide (4.1 mL, 1M in THF) was added to the solution and the mixture heated (70° C). The reaction progress was monitored by LCMS and heating was discontinued upon the expense of the starting material. The THF was removed and the resulting residue was purified by flash column chromatography (Biotage® 40 Mi, 30-50% methyl tert-butylether in hexane) affording 537 mg (54%) of the desired product. MS [(ES+), m/z]: 364/366 [M+H]$^+$, 1 Cl pattern.

Step E: 3-[(3-chloro-6-methylphenanthridin-5(6H)-yl) carbonyl]phenol—To a solution of (3-chloro-6-methyl-6H-phenanthridin-5-yl)-(3-methoxy-phenyl)-methanone (484 mg, 1.33 mmol) in dichloromethane was added cyclohexene (900 uL, 8.9 mmol). The vial was capped and purged with an inert atmosphere followed by the addition of a 1 M solution of boron tribromide in dichloromethane (5.3 mL). The solution was mixed at room temperature using an orbital shaker. After 3 hours the reaction was cooled in an ice bath (0° C.) and quenched upon the slow addition of methanol. The clear solution was concentrated and the resulting residue was immediately purified using a Biotage® 40 Mi column of prepacked silica gel (90 g), eluting with a gradient of 5-30% methyl tert-butylether in hexane at a flow rate of 50 mL/min. The fractions containing the desired product were combined and concentrated to afford 397 mg (85%) of a white solid. $^1$H NMR (400 MHz, DMSO-$d_6$) δ ppm 1.17 (d, J=6.73 Hz, 3 H) 5.60 (d, J=6.21 Hz, 1 H) 6.66 (d, J=7.50 Hz, 1 H) 6.69 (s, 1 H) 6.80 (ddd, J=8.21, 2.52, 0.91 Hz, 1 H) 6.88 (s, 1 H) 7.13 (t, J=7.89 Hz, 1 H) 7.25 (dd, J=8.41, 2.20 Hz, 1 H) 7.38 (m, 3 H) 7.94 (d, J=8.54 Hz, 2 H) 9.63 (s, 1 H); MS (ESI) m/z 350/352 ([M+H]$^+$); MS (ESI) m/z 348/350 ([M−H]$^-$).

Example 25

Synthesis of 3-{[(6R)-3-chloro-6-methylphenanthridin-5(6H)-yl]carbonyl}phenol

The enantiomers of 3-[(3-chloro-6-methylphenanthridin-5 (6H)-yl)carbonyl]phenol (367 mg, 1.05 mmol) were separated by automated, preparative, normal phase, chiral chromatography on a Chiralpak AD (20 mm×250 mm) column eluting with 100% ethanol at a flow rate of 10 mL/min. After combination of fractions and evaporation of the solvent in vacuo, one peak with a retention time of 3.801 minutes was isolated as a white solid (144 mg, 79% based upon a 1:1 ratio of enantiomers with a theoretical maximum amount of 183.5 mg). [α]$_D^{25}$=−398° (c=0.010 g/mL, CHCl$_3$); $^1$H NMR (400 MHz, DMSO-d$_6$) δ ppm 1.21 (d, J=6.73 Hz, 3 H) 5.65 (d, J=6.47 Hz, 1 H) 6.70 (d, J=7.50 Hz, 1 H) 6.73 (s, 1 H) 6.84 (ddd, J=8.15, 2.46, 0.78 Hz, 1 H) 6.92 (s, 1H) 7.17 (t, J=7.89 Hz, 1 H) 7.28 (dd, J=8.41, 2.20 Hz, 1 H) 7.39 (m, 2 H) 7.45 (m, 1H) 7.98 (d, J=8.54 Hz, 2 H) 9.68 (s, 1 H); MS (ESI) m/z 350/352 ([M+H]$^+$); MS (ESI) m/z 348/350 ([M−H]$^−$); HRMS: calcd for C$_{21}$H$_{16}$ClNO$_2$, 349.0870 (M), 350.09424 ([M+H]$^+$); found (ESI+), 350.09353.

Example 26

Synthesis of 3-{[(6S)-3-chloro-6-methylphenanthridin-5(6H)-yl]carbonyl}phenol

The enantiomers of 3-[(3-chloro-6-methylphenanthridin-5(6H)-yl)carbonyl]phenol (367 mg, 1.05 mmol) were separated by automated, preparative, normal phase, chiral chromatography on a Chiralpak AD (20 mm×250 mm) column eluting with 100% ethanol at a flow rate of 10 mL/min. After combination of fractions and evaporation of the solvent in vacuo, one peak (99.9%) with a retention time of 9.771 minutes was isolated as a white solid (135 mg, 74% based upon a 1:1 ratio of enantiomers with a theoretical maximum amount of 183.5 mg). [α]$_D^{25}$=+440° (c=g/mL, CHCl$_3$); $^1$H NMR (400 MHz, DMSO-d$_6$) δ ppm 1.21 (d, J=6.73 Hz, 3 H) 5.64 (d, J=6.21 Hz, 1H) 6.69 (d, J=7.50 Hz, 1H) 6.72 (s, 1 H) 6.83 (dd, J=2.59, 1.03 Hz, 1 H) 6.85 (m, 1 H) 6.92 (s, 1 H) 7.16 (t, J=7.89 Hz, 1 H) 7.28 (dd, J=8.41, 2.20 Hz, 1 H) 7.39 (m, 2 H) 7.45 (m, 1 H) 7.98 (d, J=8.54 Hz, 2 H); MS (ESI) m/z 350/352 ([M+H]$^+$); MS (ESI) m/z 348/350 ([M−H]$^−$); HRMS: calcd for C$_{21}$H$_{16}$ClNO$_2$, 349.0870 (M), 350.09424 ([M+H]$^+$); found (ESI+), 350.09345.

Example 27

Synthesis of 4-[(3-chloro-6-methylphenanthridin-5(6H)-yl)carbonyl]phenol

Step A: N-[1-(4'-chloro-2'-fluoro-1,1'-biphenyl-2-yl)ethyl]-4-methoxybenzamide—The title compound was prepared from 1-(4'-chloro-2'-fluoro-biphenyl-2-yl)-ethylamine (1 g, 4 mmol), triethylamine (614 uL, 4.4 mmol), and 4-methoxybenzoyl chloride (683 mg, 4 mmol) according to the procedure and in the same manner as described in Example 24, step c. The crude residue was immediately purified on a Biotage® (40 Mi) column for flash column chromatography (5-30% methyl tert-butylether in hexane) resulting in the isolation of 1.22 g (79%) of a white solid. mp 165-165.9° C.; $^1$H NMR (400 MHz, DMSO-d$_6$) δ ppm 1.31 (s, 3 H) 3.80 (s, 3 H) 4.94 (s, 1 H) 6.97 (d, J=8.79 Hz, 2 H) 7.15 (d, J=7.50 Hz, 1 H) 7.30 (s, 1 H) 7.43 (m, 2 H) 7.60 (m, 3 H) 7.82 (d, J=7.50 Hz, 2 H) 8.66 (s, 1 H). MS (ESI) m/z 384/386 ([M+H]$^+$); Anal. calcd for C$_{22}$H$_{19}$ClFNO$_2$: C:68.84 H:4.99 N:3.65 Found: C:68.81 H:5.07 N:3.65.

Step B: 3-chloro-5-(4-methoxybenzoyl)-6-methyl-5,6-dihydrophenanthridine—The title compound was prepared from N-[1-(4'-chloro-2'-fluoro-biphenyl-2-yl)-ethyl]-4-methoxy-benzamide (1.04 g, 2.7 mmol), anhydrous THF (10 mL), and lithium bis(trimethylsilyl)amide (4.1 mL, 1M in THF) according to the procedure and in the same manner as described in Example 24, step d. The THF was removed and the resulting residue was purified by flash column chromatography (Biotage® 40 Mi, 30-50% methyl tert-butylether in hexane) affording 738 mg (75%) of the desired product. MS [(ES+), m/z]: 364/366 [M+H]$^+$, 1 Cl pattern;

Step C: 4-[(3-chloro-6-methylphenanthridin-5(6H)-yl)carbonyl]phenol—The title compound was prepared from (3-chloro-6-methyl-6H-phenanthridin-5-yl)-(4-methoxyphenyl)-methanone (622 mg, 1.71 mmol), cyclohexene (900 uL, 8.9 mmol), and 1 M solution of boron tribromide in dichloromethane (6.8 mL) according to the procedure and in the same manner as described in Example 24, step e. The crude residue was immediately purified using a Biotage® 40 Mi column of prepacked silica gel (90 g), eluting with a gradient of 5-30% methyl tert-butylether in hexane at a flow rate of 50 mL/min. The fractions containing the desired product were combined and concentrated to afford 450 mg (75%) of a white solid. $^1$H NMR (400 MHz, DMSO-d$_6$) δ ppm 1.21 (d, J=6.73 Hz, 3 H) 5.67 (q, J=6.73 Hz, 1 H) 6.71 (d, J=8.79 Hz, 2 H) 6.79 (d, J=2.07 Hz, 1 H) 7.17 (d, J=8.54 Hz, 2 H) 7.26 (dd, J=8.54, 2.07 Hz, 1 H) 7.41 (m, 3 H) 7.98 (m, 2 H) 10.03 (s, 1 H); MS (ESI) m/z 350/352 ([M+H]$^+$); MS (ESI) m/z 348/350 ([M−H]$^−$).

Example 28

Synthesis of 4-{[(6R)-3-chloro-6-methylphenanthridin-5(6H)-yl]carbonyl}phenol

The enantiomers of 4-[(3-chloro-6-methylphenanthridin-5(6H)-yl)carbonyl]phenol (400 mg, 1.14 mmol) were separated by automated, on-column solvent change, preparative, normal phase, chiral chromatography on a Chiralpak AD (20 mm×250 mm) column eluting with 20% ethanol in hexane at a flow rate of 12 mL/min with. After combination of fractions and evaporation of the solvent in vacuo, one peak (99.9%) with a retention time of 3.571 minutes was isolated as a white solid (194 mg, 97% based upon a 1:1 ratio of enantiomers with a theoretical maximum amount of 200 mg). mp 273.5-276° C.; [α]$_D^{25}$=−321° (c=0.010 g/mL, CHCl$_3$); $^1$H NMR (400 MHz, DMSO-d$_6$) δ ppm 1.21 (d, J=6.73 Hz, 3 H) 5.67 (q, J=6.90 Hz, 1 H) 6.71 (d, J=8.79 Hz, 2 H) 6.79 (d, J=2.07 Hz, 1 H) 7.17 (m, 2 H) 7.26 (dd, J=8.54, 2.07 Hz, 1 H) 7.41 (m, 3 H) 7.98 (dd, 2 H) 10.04 (s, 1 H); MS (ESI) m/z 350/352 ([M+H]$^+$); MS (ESI) m/z 348/350 ([M−H]$^−$).

Example 29

Synthesis of 4-{[(6S)-3-chloro-6-methylphenanthridin-5(6H)-yl]carbonyl}phenol

The enantiomers of 4-[(3-chloro-6-methylphenanthridin-5(6H)-yl)carbonyl]phenol (400 mg, 1.14 mmol) were separated by automated, on-column solvent change, preparative, normal phase, chiral chromatography on a Chiralpak AD (20 mm×250 mm) column eluting with 20% ethanol in hexane at a flow rate of 12 mL/min with. After combination of fractions and evaporation of the solvent in vacuo, one peak (99.8%) with a retention time of 8.078 minutes was isolated as a white solid (200 mg, 100% based upon a 1:1 ratio of enantiomers with a theoretical maximum amount of 200 mg). mp 273.7-276° C.; [α]$_D^{25}$=+393° (c=0.010 g/mL, CHCl$_3$); $^1$H NMR (400 MHz, DMSO-d$_6$) δ ppm 1.21 (d, J=6.73 Hz, 3 H) 5.67 (q, J=6.73 Hz, 1 H) 6.71 (d, J=8.79 Hz, 2 H) 6.79 (d, J=2.07 Hz, 1 H) 7.17 (d, J=8.54 Hz, 2 H) 7.26 (dd, J=8.41, 2.20 Hz, 1 H) 7.41 (m, 3 H) 7.98 (m, 2 H) 10.04 (s, 1 H); MS (ESI) m/z 350/352 ([M+H]$^+$); MS (ESI) m/z 348/350 ([M−H]$^−$).

Example 30

Synthesis of 4-[3-chloro-6-methylphenanthridin-5(6H)-yl)carbonyl]benzene-1,3-diol Step A: N-[1-(4'-chloro-2'-fluoro-1,1'-biphenyl-2-yl)ethyl]-2,4-dimethoxybenzamide—The title compound was prepared from 1-(4'-chloro-2'-fluoro-biphenyl-2-yl)-ethylamine (500 mg, 2 mmol), triethylamine (293 uL, 2.1 mmol), and 2,4-dimethoxybenzoyl chloride (342 mg, 2 mmol) according to the procedure and in the same manner as described in Example 24, step c. The acetonitrile was removed in vacuo and the resulting solid dissolved in dichloromethane and applied directly to a Biotage® (40 Mi) column for flash column chromatography (5-30% methyl tert-butylether in hexane) resulting in the isolation of 820 mg (99%) of a white solid. MS (ESI) m/z 414/416 ([M+H]+.

Step B: 3-chloro-5-(2,4-dimethoxybenzoyl)-6-methyl-5,6-dihydrophenanthridine—The title compound was prepared from N-[1-(4'-chloro-2'-fluoro-biphenyl-2-yl)-ethyl]-4-methoxy-benzamide (800 mg, 1.9 mmol), anhydrous THF (10 mL), and lithium bis(trimethylsilyl)amide (3.8 mL, 1M in THF) according to the procedure and in the same manner as described in Example 24, step d. The THF was removed and the resulting residue was purified by flash column chromatography (Biotage® 40 Mi, 30-50% methyl tert-butylether in hexane) affording 564 mg (75%) of the desired product. MS [(ES+), m/z]: 394/396 [M+H]+, 1 Cl pattern;

Step C: 4-[3-chloro-6-methylphenanthridin-5(6H)-yl]carbonyl]benzene-1,3-diol—The title compound was prepared from (3-chloro-6-methyl-6H-phenanthridin-5-yl)-(4-methoxy-phenyl)-methanone (564 mg, 1.43 mmol), cyclohexene (1.45 mL, 14.5 mmol), and 1 M solution of boron tribromide in dichloromethane (8.59 mL) according to the procedure and in the same manner as described in Example 1, step e. The resulting residue was immediately purified using a Biotage® 40 Mi column of prepacked silica gel (90 g), eluting with a gradient of 5-50% methyl tert-butylether in hexane at a flow rate of 50 mL/min. The fractions containing the desired product were combined and concentrated to afford 516 mg (98%) of an oil. MS [(ES+), m/z]: 366/368 [M+H]+, 1 Cl pattern; MS [(ESI−) m/z]: 364/366 ([M−H]−), 1 Cl pattern.

Example 31

Synthesis of 4-{[(6R)-3-chloro-6-methylphenanthridin-5(6H)-yl]carbonyl}benzene-1,3-diol The enantiomers of 4-[3-chloro-6-methylphenanthridin-5(6H)-yl]carbonyl]benzene-1,3-diol (410 mg, 1.12 mmol) were separated by automated, preparative, normal phase, chiral chromatography on a Chiralpak AS (20 mm×250 mm) column eluting with 15% isopropyl alcohol in hexane at a flow rate of 20 ml/min. After combination of fractions and evaporation of the solvent in vacuo, one peak (99.9%) with a retention time of 7.479 minutes was isolated as a white solid (114 mg, 28% based upon a 1:1 ratio of enantiomers with a theoretical maximum amount of 205 mg). $[\alpha]_D^{25}$=−367.6° (c=0.0101 g/mL, CHCl$_3$); $^1$H NMR (400 MHz, DMSO-d$_6$) δ ppm 1.16 (d, J=6.98 Hz, 3 H) 5.64 (d, J=6.73 Hz, 1 H) 6.16 (d, J=1.81 Hz, 1 H) 6.23 (dd, J=8.41, 2.20 Hz, 1 H) 6.99 (d, J=8.02 Hz, 2 H) 7.23 (dd, J=8.54, 2.07 Hz, 1 H) 7.35 (m, 2 H) 7.40 (m, 1 H) 7.92 (m, 2 H) 9.60 (s, 1 H) 9.69 (s, 1 H); MS (ESI) m/z 366/368 ([M+H]+); MS (ESI) m/z 364/366 ([M−H]−); HRMS: calcd for C$_{21}$H$_{16}$ClNO$_3$, 365.0819 (M), 366.08915 ([M+H]+); found (ESI+), 366.08918.

Example 32

Synthesis of 4-{[(6S)-3-chloro-6-methylphenanthridin-5(6H)-yl]carbonyl}benzene-1,3-diol The enantiomers of 4-[3-chloro-6-methylphenanthridin-5(6H)-yl]carbonyl]benzene-1,3-diol (410 mg, 1.12 mmol) were separated by automated, preparative, normal phase, chiral chromatography on a Chiralpak AS (20 mm×250 mm) column eluting with 15% isopropyl alcohol in hexane at a flow rate of 20 mL/min. After combination of fractions and evaporation of the solvent in vacuo, one peak (99.6%) with a retention time of 9.360 minutes was isolated as a white solid (115 mg, 28% based upon a 1:1 ratio of enantiomers with a theoretical maximum amount of 205 mg). $[\alpha]_D^{25}$ =+359.5° (c=0.010 g/mL, CHCl$_3$); $^1$H NMR (400 MHz, DMSO-d$_6$) δ ppm 1.16 (d, J=6.73 Hz, 3 H) 5.64 (d, J=6.47 Hz, 1 H) 6.16 (d, J=1.55 Hz, 1 H) 6.23 (dd, J=8.28, 2.33 Hz, 1 H) 6.99 (d, J=8.28 Hz, 2 H) 7.23 (dd, J=8.54, 2.07 Hz, 1 H) 7.35 (m, 2 H) 7.40 (m, 2H) 7.92 (dd, 2 H) 9.60 (s, 1 H) 9.69 (s, 1 H); MS (ESI) m/z 366/368 ([M+H]+); MS (ESI) m/z 364/366 ([M−H]−); HRMS: calcd for C$_{21}$H$_{16}$ClNO$_3$, 365.0819 (M), 366.08915 ([M+H]+); found (ESI+), 366.0892.

Example 33

Synthesis of 3-[(3-fluoro-6-methylphenanthridin-5(6H)-yl)carbonyl]phenol

Step A: 1-(2',4'-difluoro-1,1'-biphenyl-2-yl)ethanone—2,4-Difluorophenyl boronic acid (9.47 g, 60 mmol), tetrabutylammonium bromide (16.1 g, 50 mmol), and potassium carbonate (20.7 g, 150 mmol) were added to a flask followed by water (50 mL). The contents were mixed until most of the dissolvable solids were in solution. To the remaining slurry was added 2'-bromoacetophenone (9.95 g, 50 mmol) and palladium acetate (1.12 g, 5 mmol). The flask was equipped with a condenser and the contents were heated (70° C.) with stirring while the system was immersed with a nitrogen atmosphere. After 12 h, TLC analysis indicated the formation of a single product at the expense of 2'-bromoacetophenone. Heating was discontinued and the reaction was allowed to cool. Ethyl acetate (500 mL) was added and the organic phase was extracted with water (3×100 mL). The combined water phase was extracted once with additional ethyl acetate and the organic phases were combined, dried (Na$_2$SO$_4$), filtered and concentrated to provide a crude oil. The product was isolated via flash column chromatography (Biotage® 40 Mi, 5-20%, methyl tert-butyl ether in hexane) and afforded 5.7 g (49%) of the desired product as a yellow oil. MS (EI) m/z 233 (M+.); $^1$H NMR (400 MHz, DMSO-d$_6$) δ ppm 2.42 (s, 3 H) 7.16 (m, 1 H) 7.27 (ddd, J=10.57, 9.29, 2.43 Hz, 1 H) 7.39 (m, 2 H) 7.56 (td, J=7.56, 1.54 Hz, 1 H) 7.64 (td, J=7.49, 1.41 Hz, 1 H) 7.86 (dd, J=7.43, 1.28 Hz, 1H).

Step B: 1-(-2',4'-difluoro-biphenyl-2-yl)-ethylamine—The title compound was prepared from 1-(2',4'-difluoro-1,1'-biphenyl-2-yl)ethanone (3.67 g, 15.8 mmol), anhydrous methanol (200 mL), ammonium acetate (12.2 g, 158 mmol), and sodium cyanoborohydride (1.99 g, 31.6 mmol) according to the procedure and in the same manner as described in Example 24, step b resulting in the isolation of a clear oil that was used without further purification. MS [(ES+), m/z]: 217 [M-16]+, benzylic cation as a result of the loss of NH$_2$.

Step C: N-[1-(2',4'-difluoro-1,1'-biphenyl-2-yl)ethyl]-3-methoxybenzamide—3-Methoxybenzoyl chloride (731 mg, 4.28 mmol) was added to a solution of 1-(-2',4'-difluoro-biphenyl-2-yl)-ethylamine (1.0 g, 4.28 mmol) and triethylamine (717 uL, 5.1 mmol) in dichloromethane (10 mL). The reaction was mixed overnight (16 h) on an orbital mixer at room temperature. The volume of dichloromethane was reduced in vacuo by 50% and the reaction contents were applied directly to a Biotage® (40 Mi) column for flash column chromatography (5-30% methyl tert-butylether in hexane) resulting in the isolation of 1.52 g (97%) of a white solid. mp 163.9-165° C.; ¹H NMR (400 MHz, DMSO-d6) δ ppm 1.30 (br d, J=6.21 Hz, 3 H) 3.79 (s, 3 H) 4.96 (br m, 1 H) 7.07 (dd, J=8.02, 1.81 Hz, 1 H) 7.15 (d, J=7.50 Hz, 2 H) 7.32 (m, 4 H) 7.44 (m, 2 H) 7.63 (s, 2 H) 8.79 (s, 1 H); MS (ESI) m/z 368 ([M+H]$^+$); Anal. Calcd for $C_{22}H_{19}F_2NO_2$: C:71.92 H:5.21 N:3.81 Found: C:71.54 H:5.27 N:3.73

Step D: 3-fluoro-5-(3-methoxybenzoyl)-6-methyl-5,6-dihydrophenanthridine—N-[1-(2',4'-difluoro-1,1'-biphenyl-2-yl)ethyl]-3-methoxybenzamide (1.29 g, 3.5 mmol) was dissolved in anhydrous THF (10 mL) and the vial was capped and purged with an inert atmosphere. Lithium bis(trimethylsilyl)amide (4.0 mL, 1 M in THF) was added to the solution and the mixture heated (70° C). The reaction progress was monitored by LCMS and heating was discontinued upon the expense of the starting material. The THF was removed and 2N aqueous HCl was added. The product was extracted with ethyl acetate (3×) and the combined organic phases were dried (Na$_2$SO$_4$), filtered, and concentrated to provide a crude oil. The residue was purified by flash column chromatography (Biotage® 40 Mi, 30-50% methyl tert-butylether in hexane) affording 1.0 g (82%) of the desired product. ¹H NMR (400 MHz, DMSO-d$_6$) δ ppm 1.22 (d, J=6.76 Hz, 3 H) 3.71 (s, 3 H) 5.67 (s, 1 H) 6.77 (d, J=7.28 Hz, 2 H) 6.93 (s, 1 H) 7.03 (ddd, J=8.32, 2.73, 0.91 Hz, 1 H) 7.10 (td, J=8.71, 2.60 Hz, 1 H) 7.26 (t, J=7.93 Hz, 1 H) 7.40 (m, 3 H) 7.97 (d, J=7.54 Hz, 1 H) 8.01 (dd, J=8.84, 6.24 Hz, 1H); MS (ESI) m/z 348 ([M+H]$^+$); HRMS: calcd for $C_{22}H_{18}FNO_2$, 347.1322 (M), 348.13944 ([M+H]$^+$); found (ESI_FT), 348.13903; Anal. Calcd for $C_{22}H_{18}FNO_2$: C, 76.07; H, 5.22; N, 4.03. Found: C, 76.02; H, 5.32; N, 3.97.

Step E: 3-[(3-fluoro-6-methylphenanthridin-5(6H)-yl)carbonyl]phenol—To a solution of 3-fluoro-5-(3-methoxybenzoyl)-6-methyl-5,6-dihydrophenanthridine (878 mg, 2.5 mmol) in dichloromethane was added cyclohexene (1.0 mL, 10.1 mmol). The vial was capped and purged with an inert atmosphere followed by the addition of a 1 M solution of boron tribromide in dichloromethane (10 mL). The solution was mixed at room temperature using an orbital shaker. After 3 hours the reaction was cooled in an ice bath (0° C.) and quenched upon the slow addition of methanol. The clear solution was concentrated and the resulting residue was immediately purified using a Biotage® 40 Mi column of prepacked silica gel (90 g), eluting with a gradient of 5-30% methyl tert-butylether in hexane at a flow rate of 50 mL/min. The fractions containing the desired product were combined and concentrated to afford 731 mg (85%) of a white solid. ¹H NMR (400 MHz, DMSO-d$_6$) δ ppm 1.21 (d, J=6.73 Hz, 3 H) 5.66 (q, 1 H) 6.71 (m, 3 H) 6.84 (ddd, J=8.21, 2.52, 0.91 Hz, 1 H) 7.09 (td, J=8.54, 2.59 Hz, 1 H) 7.16 (t, J=7.76 Hz, 1 H) 7.37 (m, 2 H) 7.44 (td, J=7.37, 1.81 Hz, 1 H) 7.97 (d, J=7.50 Hz, 1 H) 8.00 (dd, J=8.79, 6.21 Hz, 1 H) 9.66 (s, 1 H); MS (ESI) m/z 334 ([M+H]$^+$); MS (ESI) m/z 332 ([M−H]$^-$).

Example 34

Synthesis of 3-{[(6R)-3-fluoro-6-methylphenanthridin-5(6H)-yl]carbonyl}phenol

The enantiomers of 3-[(3-fluoro-6-methylphenanthridin-5(6H)-yl)carbonyl]phenol (660 mg, 1.98 mmol) were separated by automated, preparative, normal phase, chiral chromatography on a Chiralpak AD (20 mm×250 mm) column eluting with 100% acetonitrile at a flow rate of 20 mL/min with. The fractions containing the first peak were combined and concentrated in vacuo, to provide one peak (99.9%) with a retention time of 2.708 minutes was isolated as a white solid (270 mg, 82% based upon a 1:1 ratio of enantiomers with a theoretical maximum amount of 330 mg). $[\alpha]_D^{25}$ =−545° (c=0.0105 g/mL, CHCl$_3$); ¹H NMR (400 MHz, DMSO-d$_6$) δ ppm 1.21 (d, J=6.98 Hz, 3 H) 5.66 (q, J=6.38 Hz, 1 H) 6.69 (d, J=7.24 Hz, 2 H) 6.72 (s, 1 H) 6.83 (ddd, J=8.15, 2.46, 0.78 Hz, 1 H) 7.09 (td, J=8.67, 2.59 Hz, 1 H) 7.16 (t, J=7.89 Hz, 1 H) 7.37 (m, 2 H) 7.44 (td, 1 H) 7.96 (d, J=7.76 Hz, 1 H) 8.00 (dd, J=8.79, 6.47 Hz, 1 H) 9.66 (s, 1 H) MS (ESI) m/z 334 ([M+H]$^+$); MS (ESI) m/z 332 ([M−H]$^-$); HRMS: calcd for $C_{21}H_{16}FNO_2$, 333.1165 (M), 334.12379 ([M+H]$^+$); found (ESI+), 334.12345.

Example 35

Synthesis of 3-{[(6S)-3-fluoro-6-methylphenanthridin-5(6H)-yl]carbonyl}phenol

The enantiomers of 3-[(3-fluoro-6-methylphenanthridin-5(6H)-yl)carbonyl]phenol (660 mg, 1.98 mmol) were separated by automated, preparative, normal phase, chiral chromatography on a Chiralpak AD (20 mm×250 mm) column eluting with 100% acetonitrile at a flow rate of 20 mL/min with. The fractions containing the second peak were combined and concentrated in vacuo, affording a white solid (270 mg, 82% based upon a 1:1 ratio of enantiomers with a theoretical maximum amount of 330 mg one peak (99.9%) with a retention time of 3.894 minutes; $[\alpha]_D^{25}$=+490° (c=0.0102 g/mL, CHCl$_3$); ¹H NMR (400 MHz, DMSO-d$_6$) δ ppm 1.21 (d, J=6.98 Hz, 3 H) 5.66 (q, 1 H) 6.69 (d, J=7.50 Hz, 2 H) 6.72 (s, 1 H) 6.83 (ddd, J=8.15, 2.46, 1.03 Hz, 1 H) 7.09 (m, 1 H) 7.16 (t, J=7.89 Hz, 1 H) 7.37 (m, 2 H) 7.44 (m, J=7.37, 7.37, 1.81 Hz, 1 H) 7.96 (d, J=7.50 Hz, 1 H) 8.00 (dd, J=8.79, 6.21 Hz, 1 H) 9.66 (s, 1 H); MS (ES1) m/z 334 ([M+H]$^+$); MS (ESI) m/z 332 ([M−H]$^-$); HRMS: calcd for $C_{21}H_{16}FNO_2$, 333.1165 (M), 334.12379 ([M+H]$^+$); found (ESI+), 334.12344.

Example 36

Synthesis of 4-[(3-fluoro-6-methylphenanthridin-5(6H)-yl)carbonyl]phenol

Step A: N-[1-(2',4'-difluoro-1,1'-biphenyl-2-yl)ethyl]-4-methoxybenzamide—The title compound was prepared from 4-methoxybenzoyl chloride (731 mg, 4.28 mmol), 1-(-2',4'-difluoro-biphenyl-2-yl)-ethylamine (1 g, 4.28 mmol), and triethylamine (717 uL, 5.1 mmol) according to the procedure and in the same manner as described in Example 33, step c. The product was isolated from a Biotage® (40 Mi) column for flash column chromatography (5-30% methyl tert-butylether in hexane) resulting in the isolation of a white solid, 1.53 g (97%). mp 134.5-135° C.; ¹H NMR (400 MHz, DMSO-d$_6$) δ ppm 1.29 (d, J=5.43 Hz, 3 H) 3.80 (s, 3 H) 4.96 (m, J=5.95 Hz, 1 H) 6.97 (d, J=9.05 Hz, 2 H) 7.18 (m, 2 H) 7.36 (m, 3 H) 7.64 (d, J=4.14 Hz, 2 H) 7.83 (d, J=7.50 Hz, 2 H) 8.66 (s, 1 H); MS (ESI) m/z 368 ([M+H]$^+$); Anal. calcd for $C_{22}H_{19}F_2NO_2$: C:71.92 H:5.21 N:3.81 Found: C:72.11 H:5.23 N:3.77

Step B: 3-fluoro-5-(4-methoxybenzoyl)-6-methyl-5,6-dihydrophenanthridine—_The title compound was prepared from N-[1-(2',4'-difluoro-1,1'-biphenyl-2-yl)ethyl]-4-methoxybenzamide (1.29 g, 3.5 mmol), anhydrous THF (10 mL), and lithium bis(trimethylsilyl)amide (4.0 mL, 1M in THF) according to the procedure and in the same manner as described in Example 33, step d. The residue was purified by flash column chromatography (Biotage® 40 Mi, 30-50% methyl tert-butylether in hexane) affording 1.1 g (90%) of the desired product. ¹H NMR (400 MHz, DMSO-d$_6$) δ ppm 1.21

(d, J=6.76 Hz, 3 H) 3.77 (s, 3 H) 5.68 (q, J=6.67 Hz, 1 H) 6.60 (dd, J=10.39, 2.60 Hz, 1 H) 6.90 (d, J=8.84 Hz, 2 H) 7.07 (td, J=8.64, 2.73 Hz, 1 H) 7.27 (d, J=8.58 Hz, 2 H) 7.40 (m, 3 H) 7.97 (m, 1 H) 8.00 (dd, J=8.84, 6.24 Hz, 1 H); MS (ESI) m/z 348 ([M+H]$^+$); HRMS: calcd for $C_{22}H_{18}FNO_2$, 347.1322 (M), 348.13944 ([M+H]$^+$); found (ESI_FT), 348.13914.

Step C: 4-[(3-fluoro-6-methylphenanthridin-5(6H)-yl)carbonyl]phenol—The title compound was prepared 3-fluoro-5-(4-methoxybenzoyl)-6-methyl-5,6-dihydrophenanthridine (977 mg, 2.8 mmol), cyclohexene (1.2 mL, 11.3 mmol), and 1 M solution of boron tribromide in dichloromethane (11.3 mL) according to the procedure and in the same manner as described in Example 33, step e. The crude residue was immediately purified using a Biotage® 40 Mi column of prepacked silica gel (90 g), eluting with a gradient of 5-30% methyl tert-butylether in hexane at a flow rate of 50 mL/min. The fractions containing the desired product were combined and concentrated to afford 773 mg (90%) of a white solid.

$^1$H NMR (400 MHz, DMSO-$d_6$) δ ppm 1.21 (d, J=6.98 Hz, 3 H) 5.67 (q, J=6.73 Hz, 1 H) 6.56 (dd, J=10.60, 2.59 Hz, 1 H) 6.70 (d, J=8.79 Hz, 2 H) 7.06 (td, J=8.54, 2.59 Hz, 1 H) 7.16 (d, J=8.28 Hz, 2 H) 7.39 (m, 3 H) 7.96 (d, J=7.76 Hz, 1 H) 7.99 (dd, J=8.92, 6.34 Hz, 1 H) 10.03 (s, 1 H); MS (ESI) m/z 334 ([M+H]$^+$); MS (ESI) m/z 332 ([M−H]$^-$).

Example 37

Synthesis of 4-{[(6R)-3-fluoro-6-methylphenanthridin-5(6H)-yl]carbonyl}phenol

The enantiomers of 4-[(3-fluoro-6-methylphenanthridin-5(6H)-yl)carbonyl]phenol (720 mg, 2.16 mmol) were separated by automated, on-column solvent change, preparative, normal phase, chiral chromatography on a Chiralpak AD (20 mm×250 mm) column eluting with 35% hexane in ethanol at a flow rate of 15 mL/min with. The fractions containing the first peak were combined and concentrated in vacuo, to provide one peak (99.9%) with a retention time of 3.620 minutes was isolated as a white solid (318 mg, 88% based upon a 1:1 ratio of enantiomers with a theoretical maximum amount of 360 mg). mp 235.7-236.8° C.; $[\alpha]D_{25}$=−648° (c=0.010 g/mL, CHCl$_3$); $^1$H NMR (400 MHz, DMSO-$d_6$) δ ppm 1.21 (d, J=6.98 Hz, 3 H) 5.68 (q, J=6.73 Hz, 1 H) 6.56 (dd, J=10.48, 2.46 Hz, 1 H) 6.70 (d, J=8.79 Hz, 2 H) 7.06 (td, J=8.60, 2.72 Hz, 1 H) 7.16 (m, 2 H) 7.35 (m, 1 H) 7.42 (m, 2 H) 7.98 (td, J=8.73, 7.11 Hz, 2 H) 10.04 (s, 1H) MS (ESI) m/z 334 ([M+H]$^+$); MS (ESI) m/z 332 ([M−H]$^-$).

Example 38

Synthesis of 4-{[(6S)-3-fluoro-6-methylphenanthridin-5(6H)-yl]carbonyl}phenol

The enantiomers of 4-[(3-fluoro-6-methylphenanthridin-5(6H)-yl)carbonyl]phenol (720 mg, 2.16 mmol) were separated by automated, on-column solvent change, preparative, normal phase, chiral chromatography on a Chiralpak AD (20 mm×250 mm) column eluting with 35% hexane in ethanol at a flow rate of 15 mL/min with. The fractions containing the second peak were combined and concentrated in vacuo, to provide one peak (99.8%) with a retention time of 8.095 minutes was isolated as a white solid (345 mg, 96% based upon a 1:1 ratio of enantiomers with a theoretical maximum amount of 360 mg). mp 236.6-237.8° C.; $[\alpha]_D^{25}$=+581° (c=0.0107 g/mL, CHCl$_3$); $^1$H NMR (400 MHz, DMSO-$d_6$) δ ppm 1.21 (d, J=6.73 Hz, 3 H) 5.68 (q, J=6.73 Hz, 1 H) 6.56 (dd, J=10.39, 2.60 Hz, 1 H) 6.70 (d, J=8.79 Hz, 2 H) 7.06 (td, J=8.54, 2.59 Hz, 1 H) 7.16 (m, 2 H) 7.35 (m, 1 H) 7.42 (m, 2 H) 7.98 (td, J=8.79, 6.98 Hz, 2 H) 10.04 (s, 1H) MS (ESI) m/z 334 ([M+H]$^+$); MS (ESI) m/z 332 ([M−H]$^-$).

Example 39

Synthesis of 4-[(3-fluoro-6-methylphenanthridin-5(6H)-yl)carbonyl]benzene-1,3-diol Step A: N-1-(2',4'-difluoro-1,1'-biphenyl-2-yl)ethyl]-2,4-dimethoxybenzamide—The title compound was prepared from 2,4-dimethoxybenzoyl chloride (860 mg, 4.28 mmol), 1-(-2',4'-difluoro-biphenyl-2-yl)-ethylamine (1 g, 4.28 mmol), and triethylamine (717 uL, 5.1 mmol) according to the procedure and in the same manner as described in Example 33, step c resulting in the isolation of 1.47 g (86%) of a white solid. mp 134.8-135.2° C.; $^1$H NMR (400 MHz, DMSO-$d_6$) δ ppm 1.29 (d, J=5.95 Hz, 3 H) 3.81 (s, 3 H) 3.92 (s, 3 H) 4.93 (d, J=6.73 Hz, 1 H) 6.59 (dd, J=8.79, 2.33 Hz, 1 H) 6.64 (d, J=2.33 Hz, 1 H) 7.18 (m, 2 H) 7.49 (m, 6 H) 8.29 (s, 1 H); MS (ESI) m/z 398 ([M+H]$^+$); Anal. calcd for $C_{23}H_{21}F_2NO_3$: C:69.51 H:5.33 N:3.52 Found: C:69.27 H:5.30 N:3.39

Step B: 3-fluoro-5-(2,4-dimethoxybenzoyl)-6-methyl-5,6-dihydrophenanthridine—The title compound was prepared from N-[1-(2',4'-difluoro-1,1'-biphenyl-2-yl)ethyl]-2,4-dimethoxybenzamide (1.29 g, 3.2 mmol), anhydrous THF (10 mL), and lithium bis(trimethylsilyl)amide (4.0 mL, 1M in THF) according to the procedure and in the same manner as described in Example 33, step d. The resulting residue was purified by flash column chromatography (Biotage® 40 Mi, 30-50% methyl tert-butylether in hexane) affording 1.2 g (99%) of the desired product. $^1$H NMR (400 MHz, DMSO-$d_6$) δ ppm 1.16 (d, J=6.76 Hz, 3 H) 3.79 (br m, 6 H) 3.92 (s, 1 H) 6.28 (s, 1 H) 6.62 (m, 1H) 7.06 (s, 1 H) 7.34 (br m, 1 H) 7.42 (br m, 3 H) 7.52 (br d, J=7.54 Hz, 1 H) 7.96 (m, 2 H); MS (ESI) m/z 378 ([M+H]$^+$); HRMS: calcd for $C_{23}H_{20}FNO_3$, 377.1427 (M), 378.15000 ([M+H]$^+$); found (ESI_FT), 378.14878

Step C: 4-[(3-fluoro-6-methylphenanthridin-5(6H)-yl)carbonyl]benzene-1,3-diol—The title compound was 3-fluoro-5-(2,4-dimethoxybenzoyl)-6-methyl-5,6-dihydrophenanthridine (1.25 mg, 3.3 mmol), cyclohexene (1.74 mL, 16.5 mmol), and 1 M solution of boron tribromide in dichloromethane (16.5 mL) according to the procedure and in the same manner as described in Example 33, step e. The crude residue was immediately purified using a Biotage® 40 Mi column of prepacked silica gel (90 g), eluting with a gradient of 5-30% methyl tert-butylether in hexane at a flow rate of 50 mL/min. The fractions containing the desired product were combined and concentrated to afford 1.0 g (85%) of a white solid. $^1$H NMR (400 MHz, DMSO-$d_6$) δ ppm 1.16 (d, J=6.98 Hz, 3 H) 5.65 (d, J=6.73 Hz, 1 H) 6.16 (d, J=1.81 Hz, 1 H) 6.22 (dd, J=8.41, 2.20 Hz, 1 H) 6.75 (d, J=9.83 Hz, 1 H) 6.98 (d, J=8.28 Hz, 1 H) 7.04 (td, J=8.60, 2.72 Hz, 1 H) 7.36 (m, 3 H) 7.90 (d, J=7.50 Hz, 1 H) 7.94 (dd, J=8.92, 6.34 Hz, 1 H) 9.62 (s, 1 H) 9.70 (s, 1 H) MS (ESI) m/z 350 ([M+H]$^+$); MS (ESI) m/z 348 ([M−H]$^-$); HRMS: calcd for $C_{21}H_{16}FNO_3$, 349.1114 (M), 348.10414 ([M+H]$^+$); found (ESI−), 348.10418.

Example 40

Synthesis of 4-{[(6R)-3-fluoro-6-methylphenanthridin-5(6H)-yl]carbonyl}benzene-1,3-diol The enantiomers of 4-[(3-fluoro-6-methylphenanthridin-5(6H)-yl)carbonyl]benzene-1,3-diol (800 mg, 2.29 mmol)

were separated by automated, preparative, normal phase, chiral chromatography on a Chiralpak AS (20 mm×250 mm) column eluting with 15% isopropyl alcohol in hexane at a flow rate of 20 mL/min with. The fractions containing the first peak were combined and concentrated in vacuo, to provide one peak (99.9%) with a retention time of 7.971 minutes was isolated as a white solid (224 mg, 56% based upon a 1:1 ratio of enantiomers with a theoretical maximum amount of 400 mg). mp 184-187° C.; $[\alpha]_D^{25}$=−665° (c=0.0104 g/mL, CHCl$_3$); 1H NMR (400 MHz, DMSO-d$_6$) δ ppm 1.16 (d, J=6.73 Hz, 3 H) 5.65 (m, J=6.73 Hz, 1 H) 6.16 (d, J=1.81 Hz, 1 H) 6.22 (dd, J=8.41, 2.20 Hz, 1 H) 6.75 (d, J=9.83 Hz, 1 H) 6.98 (d, J=8.28 Hz, 1 H) 7.04 (td, J=8.67, 2.59 Hz, 1 H) 7.33 (m, 2 H) 7.39 (m, 1 H) 7.90 (d, J=7.76 Hz, 1 H) 7.94 (dd, J=8.79, 6.21 Hz, 1 H) 9.62 (s, 1 H) 9.70 (s, 1 H); MS (ESI) m/z 350 ([M+H]$^+$); MS (ESI) m/z 348 ([M−H]$^−$); HRMS: calcd for C$_{21}$H$_{16}$FNO$_3$, 349.1114 (M), 350.1187 ([M+H]$^+$); found (ESI+), 350.1181.

Example 41

Synthesis of 4-{[(6S)-3-fluoro-6-methylphenanthridin-5(6H)-yl]carbonyl}benzene-1,3-diol The enantiomers of 4-[(3-fluoro-6-methylphenanthridin-5(6H)-yl)carbonyl]benzene-1,3-diol (800 mg, 2.29 mmol) were separated by automated, preparative, normal phase, chiral chromatography on a Chiralpak AS (20 mm×250 mm) column eluting with 15% isopropyl alcohol in hexane at a flow rate of 20 mL/min with. The fractions containing the second peak were combined and concentrated in vacuo, to provide one peak (99.3%) with a retention time of 9.345 minutes was isolated as a white solid (220 mg, 55% based upon a 1:1 ratio of enantiomers with a theoretical maximum amount of 400 mg). mp 182-184° C.; $[\alpha]_D^{25}$=+618° (c=0.0101 g/mL, CHCl$_3$); 1H NMR (400 MHz, DMSO-d$_6$) δ ppm 1.16 (d, J=6.73 Hz, 3 H) 5.65 (d, J=6.73 Hz, 1 H) 6.16 (d, J=1.81 Hz, 1 H) 6.22 (dd, J=8.41, 2.20 Hz, 1 H) 6.75 (d, J=10.35 Hz, 1 H) 6.98 (d, J=8.28 Hz, 1 H) 7.04 (td, J=8.60, 2.72 Hz, 1 H) 7.33 (m, 2 H) 7.39 (ddd, J=7.70, 6.79, 2.07 Hz, 1 H) 7.90 (d, J=7.50 Hz, 1 H) 7.94 (dd, J=8.79, 6.47 Hz, 1 H) 9.62 (s, 1 H) 9.70 (s, 1 H) MS (ESI) m/z 350 ([M+H]$^+$); MS (ESI) m/z 348 ([M−H]$^−$); HRMS: calcd for C$_{21}$H$_{16}$FNO$_3$, 349.1114 (M), 350.1187 ([M+H]$^+$); found (ESI+), 350.11817.

Example 42

Synthesis of 4-[(3,8-difluoro-6-methylphenanthridin-5(6H)-yl)carbonyl]phenol

Step A: 4-Methoxy-N-[1-(2',4,4'-trifluoro-1,1'-biphenyl-2-yl)ethyl]benzamide—A stirred solution of 1-(2',4,4'-trifluoro-1,1'-biphenyl-2-yl)ethylamine (0.71 g, 2.84 mmol) in dichloromethane (5 mL) was treated with 4-methoxybenzoyl chloride (0.51 g, 3.0 mmol), and N,N-diisopropylethylamine (0.77 g, 6.0 mmol). The reaction was stirred at room temperature for twelve hours, and the solvent evaporated in vacuo to a crude oil. The crude oil was purified by preparative liquid chromatography on a Biotage® 40 Mi column of pre-packed silica gel (90 g), eluting with a gradient of between 5% and 50% methyl tert-butyl ether in hexane at a flow rate of 40 mL/min to afford, after evaporation of the solvent, a colorless oil. Crystallization of the colorless oil from ethyl acetate-hexane yielded the title compound (0.98 g, 2.54 mmol, 90%) as a homogeneous, colorless, crystalline solid, m.p. 163-165° C.; MS [(+ESI), m/z]: 386 [M+H]$^+$; IR (Solid), v$_{max}$: 3257, 1620, 1606, 1503, 1329, 1249, 1175, 1032, 844, 777, 670 cm$^{−1}$; $^1$H NMR (400 MHz, DMSO-d$_6$) δ: 1.29 (d, J=5.4 Hz, 3H), 3.80 (s, 3H), 4.93 (broad s, 1H), 6.93 (d, J=8.8 Hz, 2H), 7.14 (td, J=8.5, 2.7 Hz, 1H), 7.22 (dd, J=8.5, 5.9 Hz, 2H), 7.37 (t, 2H), 7.46 (d, J=9.1 Hz, 1H), 7.61 (d, J=4.7 Hz, 1H), 7.83 (d, J=7.2 Hz, 2H), 8.66 (d, J=3.9 Hz, 1H), exists as approximate 2:1 mixture of rotamers; Anal. calcd for C$_{22}$H$_{18}$F$_3$NO$_2$: C, 68.57; H, 4.71; N, 3.63. Found: C, 68.65; H, 4.80 N, 3.48.

Step B: 3,8-Difluoro-5-(4-methoxybenzoyl)-6-methyl-5,6-dihydrophenanthridine—A stirred solution of 4-methoxy-N-[1-(2',4,4'-trifluoro-1,1'-biphenyl-2-yl)ethyl]benzamide (0.95 g, 2.46 mmol) in tetrahydrofuran was treated under nitrogen with a 1.0 M solution of lithium bis(trimethylsilyl)amide in tetrahydrofuran (5 mL, 5.0 mmol) and heated at 70° C. for fifteen hours. The reaction mixture was cooled to room temperature and the solvent removed in vacuo to afford a residue. The residue was dissolved in ethyl acetate and washed sequentially with a 1 N hydrochloric acid solution and water. The organic phase was dried over anhydrous sodium sulfate, filtered, and the solvent removed in vacuo to afford a crude solid. The crude solid was purified by preparative liquid chromatography on a Biotage® 40 Mi column of pre-packed silica gel (90 g), eluting with a gradient of between 3% and 15% methyl tert-butyl ether in hexane to afford, after crystallization from ethyl acetate-hexane, the title compound (0.36 g, 0.99 mmol, 40%) as a homogeneous, colorless, crystalline solid, m.p. 98-100° C.; MS [(+ESI), m/z]: 366 [M+H]$^+$; IR (Solid), v$_{max}$: 2920, 1630, 1600, 1580, 1510, 1495, 1385, 1320, 1250, 870, 840, 810 cm$^{−1}$; $^1$H NMR (400 MHz, DMSO-d$_6$) δ: 1.22 (d, J=7.0 Hz, 3H), 3.77 (s, 3H), 5.73 (q, J=6.7 Hz, 1H), 6.59 (dd, J=10.3, 2.3 Hz, 1H), 6.90 (d, J=8.8 Hz, 2H), 7.07 (td, J=8.6, 2.7 Hz, 1H), 7.27 (d, J=8.3 Hz, 2H), 7.27 (td, J=8.5, 3.2 Hz, 1H), 7.39 (dd, J=9.2, 2.7 Hz, 1H), 7.98 (dd, J=8.9, 6.3 Hz, 1H), 8.02 (dd, J=8.5, 5.4 Hz, 1H); Anal. calcd for C$_{22}$H$_{17}$F$_2$NO$_2$: C, 72.32; H, 4.69; N, 3.83. Found: C, 71.82; H, 4.52; N, 3.76.

Step C: 4-[(3,8-Difluoro-6-methylphenanthridin-5(6H)-yl)carbonyl]phenol—A stirred suspension of 3,8-difluoro-5-(4-methoxybenzoyl)-6-methyl-5,6-dihydrophenanthridine (0.20 g, 0.55 mmol) and cyclohexene (1.64 g, 20.0 mmol) was treated at room temperature under nitrogen with a solution of 1.0 M boron tribromide in dichloromethane (4.0 mL, 4.0 mmol). After stirring for approximately two hours at room temperature, the reaction was cooled to −20° C. and quenched with methanol (5 mL). The solvent was evaporated in vacuo to a dark oil. The dark oil was purified by preparative liquid chromatography on a Biotage® 40 Mi column of pre-packed silica gel (90 g), eluting with a gradient of between 5% and 30% methyl tert-butyl ether in hexane at a flow rate of 50 mL/min to afford, after evaporation of the solvent in vacuo and trituration with diethyl ether-hexane, the title compound (0.19 g, 0.54 mmol, 99%) as a homogeneous, colorless, racemic solid, m.p. 193-195° C.; MS [(+ESI), m/z]: 352 [M+H]$^+$; MS [(−ESI), m/z]: 350 [M−H]$^−$; $^1$H NMR (400 MHz, DMSO-d$_6$) δ: 1.21 (d, J=7.0 Hz, 3H), 5.71 (q, J=6.8 Hz, 1H), 6.55 (dd, J=10.5, 2.5 Hz, 1H), 6.70 (d, J=8.6 Hz, 2H), 7.06 (td, J=8.6, 2.6 Hz, 1H), 7.16 (d, J=8.6 Hz, 2H), 7.27 (td, J=8.8, 2.7 Hz, 1 H), 7.38 (dd, J=9.2, 2.7 Hz, 1H), 7.97 (dd, J=9.0, 6.4 Hz, 1H), 8.01 (dd, J=9.1, 6.0 Hz, 1H), 10.04 (s, 1H).

Example 43

Synthesis of 4-{[(6R)-3,8-Difluoro-6-methylphenanthridin-5(6H)-yl]carbonyl}phenol*

The enantiomers of 4-[(3,8-difluoro-6-methylphenanthridin-5(6H)-yl)carbonyl]phenol (0.15 g, 0.43 mmol) were separated by automated, preparative, normal phase, chiral chromatography on a Chiralpak AD-H® (2×25 cm) column eluting with ethanol at a flow rate of 10 ml/min. After evaporation of the solvent in vacuo, peak one with a retention time at 6.0 minutes and monitored by ultraviolet detection yielded, after trituration with diethyl ether-hexane, 4-{[(6R)-3,8-difluoro-6-methylphenanthridin-5(6H)-yl]carbonyl}phenol* (0.05 g, 0.14 mmol, 33%) as a homogeneous, colorless, amorphous solid, m.p. 138-140° C.; $T_R$=6.0 minutes; $[\alpha]_D^{25}$= −560° (c=10.0 mg/mL in $CHCl_3$); MS [(+ESI), m/z]: 352[M+H]$^+$; MS [(−ESI), m/z]: 350 [M−H]$^-$; IR (Solid), $v_{max}$: 3300, 1606, 1570, 1510, 1495, 1390, 1330, 1265, 1225, 870, 810 cm$^{-1}$; $^1$H NMR (400 MHz, DMSO-$d_6$) δ: 1.21 (d, J=6.8 Hz, 3H), 5.71 (q, J=6.8 Hz, 1H), 6.55 (dd, J=10.5, 2.5 Hz, 1H), 6.70 (d, J=8.8 Hz, 2H), 7.06 (td, J=8.6, 2.6 Hz, 1H), 7.16 (d, J=8.6Hz, 2H), 7.27 (td, J=8.8, 2.7 Hz, 1H), 7.38 (dd, J=9.2, 2.7 Hz, 1H), 7.07 (dd, J=9.0, 6.4 Hz, 1H), 8.01 (dd, J=9.0, 5.6 Hz, 1H), 10.06 (s, 1H); Anal. calcd for $C_{21}H_{15}F_2NO_2$: C, 71.79; H, 4.30; N, 3.99. Found: C, 71.83; H, 4.96; N, 3.54. *The stereochemical configuration is not absolute and was assigned arbitrarily.

Example 44

Synthesis of 4-{[(6S)-3,8-Difluoro-6-methylphenanthridin-5(6H)-yl]carbonyl}phenol*

The enantiomers of 4-[(3,8-difluoro-6-methylphenanthridin-5(6H)-yl)carbonyl]phenol (0.15 g, 0.43 mmol) were separated by automated, preparative, normal phase, chiral chromatography on a Chiralpak AD-H® (2×25 cm) column eluting with ethanol at a flow rate of 10 mL/min. After evaporation of the solvent in vacuo, peak two with a retention time at 9.5 minutes and monitored by ultraviolet detection yielded, after trituration with hexane, 4-{[(6S)-3,8-difluoro-6-methylphenanthridin-5(6H)-yl]carbonyl}phenol* (0.04 g, 0.11 mmol, 26%) as a homogeneous, colorless, amorphous solid, m.p. 135-138° C.; $T_R$=9.5 minutes; $[\alpha]_D^{25}$ =+561° (c=10.0 mg/mL in $CHCl_3$); MS [(+ESI), m/z]: 352 [M+H]$^+$; MS [(−ESI), m/z]: 350 [M−H]$^-$; IR (Solid), $V_{max}$: 3300, 1606, 1570, 1510, 1495, 1390, 1330, 1265, 1225, 870, 810 cm$^{-1}$; $^1$H NMR (400 MHz, DMSO-$d_6$) δ 1.21 (d, J=6.8 Hz, 3H), 5.71 (q, J=6.8 Hz, 1H), 6.55 (dd, J=10.4, 2.6 Hz, 1H), 6.70 (d, J=8.6 Hz, 2H), 7.06 (td, J=8.7, 2.6 Hz, 1H), 7.16 (d, J=8.6 Hz, 2H), 7.27 (td, J=8.8, 2.7 Hz, 1H), 7.38 (dd, J=9.1, 2.6 Hz, 1H), 7.97 (dd, J=8.7, 6.4 Hz, 1H), 8.01 (dd, J=8.8, 5.5 Hz, 1H), 10.05 (m, 1H); Anal. calcd for $C_{21}H_{15}F_2NO_2$: C, 71.79; H, 4.30; N, 3.99. Found: C, 70.68; H, 4.50; N, 3.69. * The stereochemical configuration is not absolute and was assigned arbitrarily.

Example 45

Synthesis of 4-{[(6R)-3,8-difluoro-6-methylphenanthridin-5(6H)-yl]carbonyl}-2-fluorophenol 4-{[(6R)-3,8-difluoro-6-methylphenanthridin-5(6H)-yl]carbonyl}-2-fluorophenol was prepared in a similar fashion as outlined in example 42. It was purified by chiral HPLC.

[a]D25=−453.7° (c=10 mg/mL, MeOH); MS (ES) m/z 369.8.

Example 46

Representative compounds of this invention were evaluated in the following standard pharmacological test procedures which demonstrated antiinflammatory activity. The test procedures used and the results obtained are briefly described below.

Test Procedures:

Cells

T-175 flasks of 100% confluent HAECT-1 cells (immortalized human aortic endothelial cells) were washed with 8 ml of HBSS (HEPES buffered saline solution) and infected for four hours with 6 ml of a 1:10 dilution of Ad5-wt-hERα virus (an adenovirus transfection vector that mediates CMV promoter driven expression of human ERα) in phenol red free Endothelial Cell Basal medium (Clonetics, San Diego Calif., Catalog # CC-3129) containing 0.25% bovine serum albumin (EBM-BSA). After four hours, cells were washed with EBM-BSA and incubated overnight in the same medium. Following overnight incubation, cells were washed with EBM-BSA and infected for 2 hours with 6 ml of a 1:10 dilution of Ad5-3x (NFκB).Luc virus (Adenovirus luciferase expression vector driven by 3 repeats of the MHC NFκb site 5' to the thymidine kinase promoter) in EBM-BSA. After two hours, cells were washed and incubated at 34° C. for 1 hour. Cells were then washed, trypsinized, counted and resuspended in 95% FBS/ 5% dimethylsulfoxide at a concentration of 4×10$^6$ cells/ml, frozen as 1 or 5 ml aliquots in cryo-vials and stored at −150° C. Control (no ER infection) cells were processed as above without Ad5-wt-hERα virus infection.

IL-6 and Creatine Kinase Assays

ERα infected HAECT-1 cells or control cells were thawed, diluted 42× in warm EBM-BSA, plated into 96-well plates at 0.1 ml/well and incubated for 4 h at 34° C. Test compounds were added to the cells as 2× stocks in EBM-BSA containing 2 ng/ml IL-1β Ad5-IL-6(1250 bp).Luc virus and plates were returned to the incubator (34° C.). After 15-20 h, cells are lysed with 50 ul of Promega Cell Culture Lysis reagent for ~5 min at room temp on shaker. After lysing, 15 ul of lysate is transferred to luminometer plates for luciferase determination. Luciferase activity is evaluated using a Perkin Elmer Victor2 1420 multilabel counter. Creatine kinase was determined from the rate of increase in $A_{340}$ following addition of 100 uL of CK assay reagent (Sigma, cat. No 47-10) to the remainder of the cell lysate.

Data Analyses

For $IC_{50}$ and $EC_{50}$ calculations, mean IL-6, luciferase or CK values versus $log_{10}$ of the compound concentration were fitted to a four parameter logistic equation. The $IC_{50}/EC_{50}$ value, 'Hill slope', upper and lower limits of the curve were iteratively estimated.

Mice

Ovariectomized C57BL/6 mice (16-20 g) (Taconic) were separated into groups of 8. After 5-7 days of recuperation, the mice were fed a chow diet or an atherogenic diet (15.75% fat, 1.25% cholesterol and 0.5% sodium cholate) (Purina diet #21539). EE or test compound was administered once daily by gavage in a methylcellulose/tween vehicle (0.1 ml per mouse) for 5 weeks. At the end of the experimental period, the liver was collected and uterine wet weight was recorded.

RNA Analysis

Liver total RNA was prepared by using Trizol reagent (BRL). Estrogen and compound regulation of NF-κB target genes were verified by real time RT-PCR using an ABI PRISM 7700 Sequence Detection System according to the manufacturer's protocol (Applied Biosystems). The data was analyzed using the Sequence Detector v1.7 software (Applied Biosystems) and normalized to GAPDH using the Applied Biosystems primer set.

The following table summarizes the results obtained in the standard pharmacological test procedures described above:

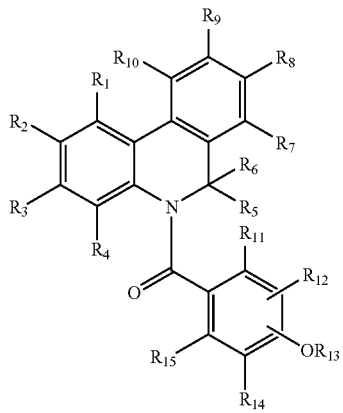

| Example # | Stereo | R2 | R7 | R9 | R10 | R11 | R12 | R13 | IL6-luc IC$_{50}$ nM (% E2) | CK EC$_{50}$ nM (% E2) |
|---|---|---|---|---|---|---|---|---|---|---|
| 3 | 1 | | F | Me | | OH | | | 414 114%) | |
| 2 | 1 | | F | Me | | | OH | | 38 (53%) | IA |
| 1 | 1 | | F | Me | | | OH | | 5 (100%) | IA |
| 31 | 1 | Cl | | Me | OH | | OH | | 3 (87%) | IA |
| 32 | 1 | Cl | | Me | OH | | OH | | 789 (125%) | IA |
| 20 | 1 | | F | Et | | | OH | | 6 (95%) | IA |
| 19 | 1 | | F | Et | | | OH | | 85 (88%) | IA |
| 4 | 1 | | F | Me | | OH | | | 47 (102%) | IA |
| 5 | 1 | | F | Me | F | | OH | | 9 (97%) | IA |
| 6 | 1 | | F | Me | F | | OH | | 403 (90%) | IA |
| 24 | racemic | Cl | | Me | | OH | | | Not tested | |
| 25 | 1 | Cl | | Me | | OH | | | 9 (103%) | 141 (26%) |
| 26 | 1 | Cl | | Me | | OH | | | 377 (49%) | IA |
| 27 | racemic | Cl | | Me | | | OH | | Not tested | |
| 28 | 1 | Cl | | Me | | | OH | | 6 (120%) | 69 (32%) |
| 29 | 1 | Cl | | Me | | | OH | | 1000 (75%) | IA |
| 7 | 1 | | F | Me | F | | | OH | 263 (70%) | IA |
| 8 | 1 | | F | Me | F | | | OH | IA | IA |
| 33 | racemic | F | | Me | | OH | | | Not tested | |
| 34 | 1 | F | | Me | | OH | | | 11 (188%) | IA |
| 35 | 1 | F | | Me | | OH | | | IA | |
| 36 | racemic | F | | Me | | | OH | | Not tested | |
| 37 | 1 | F | | Me | | | OH | | 6 (114%) | 28 (20%) |
| 38 | 1 | F | | Me | | | OH | | IA | |
| 39 | racemic | F | | Me | OH | | OH | | Not tested | |
| 40 | 1 | F | | Me | OH | | OH | | 1 (107%) | 8 (20%) |
| 41 | 1 | F | | Me | OH | | OH | | 272 (88%) | IA |
| 22 | 1 | | F | Et | OH | | OH | | 2 (106%) | 3 (38%) |
| 21 | 1 | | F | Et | | OH | | | 40 (134%) | 50% @ 1 µM |
| 10 | 1 | | F | Me | | F | OH | | 1473 (68%) | IA |
| 9 | 1 | | F | Me | | F | OH | | 31 (81%) | IA |
| 23 | racemic | | F | Et | F | | OH | | 1 (107%) | IA |
| 17 | 1 | | F | Me | | O-Me | OH | | 364 (113%) | IA |
| 18 | 1 | | F | Me | | O-Me | OH | | IA | |
| 11 | 1 | | F | Me | | OH | Cl | | 271 (107%) | 307 (−29%) |
| 12 | 1 | | F | Me | | OH | Cl | | IA | |
| 13 | 1 | | F | Me | | Br | OH | | 51 (102%) | IA |
| 14 | 1 | | F | Me | | Br | OH | | IA | |
| 15 | 1 | | F | Me | Br | | | OH | 301 (76%) | IA |
| 16 | 1 | | F | Me | Br | | | OH | 832 (91%) | IA |
| 42 | racemic | F | F | Me | | | OH | | 4.5 (95%) | 90 (37%) |
| 43 | 1 | F | F | Me | | | OH | | 1.5 (147%) | |
| 44 | 1 | F | F | Me | | | OH | | 130 (132%) | |

If not otherwise indicated, the R$_1$-R$_{14}$ substituent represents hydrogen.

E2 inhibits NF-κB and IL-6 expression in Ad5-wt-ER infected HAECT-1 cells with an IC$_{50}$ value around 1 nM and induces expression of creatine kinase in the same cells with similar potency (5.8 nM). In contrast, preferred compounds of the present invention potently and efficaciously inhibit NF-κB and IL-6 expression in Ad5-wt-ER infected HAECT-1 cells but do not induce CK expression in an ER-dependent manner. The ability of preferred compounds of the present invention to inhibit NF-κB and IL-6 expression without inducing CK activity demonstrates anti-inflammatory activity in the absence of classic estrogenic activity.

Based on the results obtained in the standard pharmacological test procedures, the compounds of this invention are selective anti-inflammatory compounds useful for the treatment and prevention of chronic inflammatory diseases with out stimulating uterine and breast cell proliferation as found with classic estrogens.

Example 47

The processes detailed below are illustrative of processes for evaluating the compounds of the present invention.

Evaluation of Test Compound Using an ERE-Reporter Test Procedure in MCF-7 Breast Cancer Cells Stock solutions of test compounds (usually 0.1 M) are prepared in DMSO and then diluted 10 to 100-fold with DMSO to make working solutions of 1 or 10 mM. The DMSO stocks are stored at either 4° C. (0.1 M) or −20° C. (<0.1 M). MCF-7 cells are passaged twice a week with growth medium [D-MEM/F-12 medium containing 10% (v/v) heat-inactivated fetal bovine serum, 1% (v/v) Penicillin-Streptomycin, and 2 mM glutaMax-1]. The cells are maintained in vented flasks at 37° C. inside a 5% $CO_2$/95% humidified air incubator. One day prior to treatment, the cells are plated with growth medium at 25,000 cells/well into 96 well plates and incubated at 37° C. overnight.

The cells are infected for 2 hr at 37° C. with 50 µl/well of a 1:10 dilution of adenovirus 5-ERE-tk-luciferase in experimental medium [phenol red-free D-MEM/F-12 medium containing 10% (v/v) heat-inactived charcoal-stripped fetal bovine serum, 1% (v/v) Penicillin-Streptomycin, 2 mM glutaMax-1, 1 mM sodium pyruvate]. The wells are then washed once with 150 µl of experimental medium. Finally, the cells are treated for 24 hr at 37° C. in replicates of 8 wells/treatment with 150µl/well of vehicle (≦0.1% v/v DMSO) or compound that is diluted ≧1000-fold into experimental medium.

Initial screening of test compounds is done at a single dose of 1 µM that is tested alone (estrogen receptor agonist mode) or in combination with 0.1 nM 17β-estradiol (EC80; estrogen receptor antagonist mode). Each 96 well plate also includes a vehicle control group (0.1% v/v DMSO) and an estrogen receptor agonist control group (either 0.1 or 1 nM 17β-estradiol). Dose-response experiments are performed in either the estrogen receptor agonist and/or estrogen receptor antagonist modes on active compounds in log increases from $10^{-14}$ to $10^{-5}$ M. From these dose-response curves, $EC_{50}$ and $IC_{50}$ values, respectively, are generated. The final well in each treatment group contains 5 µl of $3 \times 10^{-5}$ M ICI-182,780 ($10^{-6}$ M final concentration) as an estrogen receptor antagonist control.

After treatment, the cells are lysed on a shaker for 15 min with 25 µl/well of 1× cell culture lysis reagent (Promega Corporation). The cell lysates (20 µl) are transferred to a 96 well luminometer plate, and luciferase activity is measured in a MicroLumat LB 96 P luminometer (EG & G Berthold) using 100 µl/well of luciferase substrate (Promega Corporation). Prior to the injection of substrate, a 1 second background measurement is made for each well. Following the injection of substrate, luciferase activity is measured for 10 seconds after a 1 second delay. The data are transferred from the luminometer to a Macintosh personal computer and analyzed using the JMP software (SAS Institute); this program subtracts the background reading from the luciferase measurement for each well and then determines the mean and standard deviation of each treatment.

The luciferase data are transformed by logarithms, and the Huber M-estimator is used to down-weight the outlying transformed observations. The JMP software is used to analyze the transformed and weighted data for one-way ANOVA (Dunnett's test). The compound treatments are compared to the vehicle control results in the estrogen receptor agonist mode, or the positive estrogen receptor agonist control results (0.1 nM 17β-estradiol) in the estrogen receptor antagonist mode. For the initial single dose experiment, if the compound treatment results are significantly different from the appropriate control (p<0.05), then the results are reported as the percent relative to the 17β-estradiol control [i.e., ((compound−vehicle control)/(17β-estradiol control−vehicle control))×100]. The JMP software is also used to determine the $EC_{50}$ and/or $IC_{50}$ values from the non-linear dose-response curves.

Evaluation of Uterotrophic Activity

Uterotrophic activity of a test compound can be measured according to the following standard pharmacological test procedures.

Procedure 1: Sexually immature (18 days of age) Sprague-Dawley rats are obtained from Taconic and provided unrestricted access to a casein-based diet (Purina Mills 5K96C) and water. On day 19, 20 and 21 the rats are dosed subcutaneously with 17α-ethinyl-17β-estradiol (0.06 µg/rat/day), test compound or vehicle (50% DMSO/50% Dulbecco's PBS). To assess estrogen receptor antagonist, compounds are coadministered with 17α-ethinyl-17β-estradiol (0.06 µg/rat/day). There are six rats/group and they are euthanized approximately 24 hours after the last injection by $CO_2$ asphyxiation and pneumothorax. Uteri are removed and weighed after trimming associated fat and expressing any internal fluid. A tissue sample can also be snap frozen for analysis of gene expression (e.g. complement factor 3 mRNA).

Procedure 2: Sexually immature (18 days of age) 129 SvE mice are obtained from Taconic and provided unrestricted access to a casein-based diet (Purina Mills 5K96C) and water. On day 22, 23, 24 and 25 the mice are dosed subcutaneously with compound or vehicle (corn oil). There are six mice/group and they are euthanized approximately 6 hours after the last injection by $CO_2$ asphyxiation and pneumothorax. Uteri are removed and weighed after trimming associated fat and expressing any internal fluid.

Evaluation of Osteoporosis and Lipid Modulation (Cardioprotection)

Female Sprague-Dawley rats, ovariectomized or sham operated, are obtained 1 day after surgery from Taconic Farms (weight range 240-275 g). They are housed 3 or 4 rats/cage in a room on a 12/12 (light/dark) schedule and provided with food (Purina 5K96C rat chow) and water ad libitum. Treatment for all studies begin 1 day after arrival and rats are dosed 7 days per week as indicated for 6 weeks. A group of age matched sham operated rats not receiving any treatment serve as an intact, estrogen replete control group for each study.

All test compounds are prepared in a vehicle of 50% DMSO (JT Baker, Phillipsburg, N.J.)/1× Dulbecco's phosphate saline (GibcoBRL, Grand Island, N.Y.) at defined concentrations so that the treatment volume is 0.1 mL/100 g body weight. 17β-estradiol is dissolved in corn oil (20 µg/mL) and delivered subcutaneously, 0.1 mL/rat. All dosages are adjusted at three week intervals according to group mean body weight measurements, and given subcutaneously.

Five weeks after the initiation of treatment and one week prior to the termination of the study, each rat is evaluated for bone mineral density (BMD). The total and trabecular density of the proximal tibia are evaluated in anesthetized rats using an XCT-960M (pQCT; Stratec Medizintechnik, Pforzheim, Germany). The measurements are performed as follows: Fifteen minutes prior to scanning, each rat is anesthetized with an intraperitoneal injection of 45 mg/kg ketamine, 8.5 mg/kg xylazine, and 1.5 mg/kg acepromazine.

The right hind limb is passed through a polycarbonate tube with a diameter of 25 mm and taped to an acrylic frame with the ankle joint at a 90° angle and the knee joint at 180°. The polycarbonate tube is affixed to a sliding platform that maintains it perpendicular to the aperture of the pQCT. The platform is adjusted so that the distal end of the femur and the proximal end of the tibia is in the scanning field. A two dimensional scout view is run for a length of 10 mm and a line resolution of 0.2 mm. After the scout view is displayed on the monitor, the proximal end of the tibia is located. The pQCT scan is initiated 3.4 mm distal from this point. The pQCT scan is 1 mm thick, has a voxel (three dimensional pixel) size of 0.140 mm, and consists of 145 projections through the slice.

After the pQCT scan is completed, the image is displayed on the monitor. A region of interest including the tibia but excluding the fibula is outlined. The soft tissue is mathematically removed using an iterative algorithm. The density of the remaining bone (total density) is reported in mg/cm$^3$. The outer 55% of the bone is mathematically peeled away in a concentric spiral. The density of the remaining bone (Trabecular density) is reported in mg/cm$^3$.

One week after BMD evaluation the rats are euthanized by $CO_2$ asphyxiation and pneumothorax, and blood is collected for cholesterol determination. The uteri are also removed and the weighed after trimming associated fat and expressing any luminal fluid. Total cholesterol is determined using a Boehringer-Mannheim Hitachi 911 clinical analyzer using the Cholesterol/HP kit. Statistics were compared using one-way analysis of variance with Dunnet's test.

Evaluation of Antioxidant Activity

Porcine aortas are obtained from an abattoir, washed, transported in chilled PBS, and aortic endothelial cells are harvested. To harvest the cells, the intercostal vessels of the aorta are tied off and one end of the aorta clamped. Fresh, sterile filtered, 0.2% collagenase (Sigma Type I) is placed in the vessel and the other end of the vessel then clamped to form a closed system. The aorta is incubated at 37° C. for 15-20 minutes, after which the collagenase solution is collected and centrifuged for 5 minutes at 2000×g. Each pellet is suspended in 7 mL of endothelial cell culture medium consisting of phenol red free DMEM/Ham's F12 media supplemented with charcoal stripped FBS (5%), NuSerum (5%), L-glutamine (4 mM), penicillin-streptomycin (1000 U/ml, 100 μg/ml) and gentamycin (75 μg/ml), seeded in 100 mm petri dish and incubated at 37° C. in 5% $CO_2$. After 20 minutes, the cells are rinsed with PBS and fresh medium added, this was repeated again at 24 hours. The cells are confluent after approximately 1 week. The endothelial cells are routinely fed twice a week and, when confluent, trypsinized and seeded at a 1:7 ratio. Cell mediated oxidation of 12.5 μg/mL LDL is allowed to proceed in the presence of the compound to be evaluated (5 μM) for 4 hours at 37° C. Results are expressed as the percent inhibition of the oxidative process as measured by the TBARS (thiobarbituric acid reactive substances) method for analysis of free aldehydes (Yagi, Biochemical Medicine 15: 212-6 (1976)).

Progesterone Receptor mRNA Regulation Standard Pharmacological Test Procedure

This test procedure can be used to evaluate the estrogenic or antiestrogenic activity of compounds from this invention (Shughrue, et al., Endocrinology 138: 5476-5484 (1997)).

Rat Hot Flush Test Procedure

The effect of test compounds on hot flushes can be evaluated in a standard pharmacological test procedure which measures the ability of a test compound to blunt the increase in tail skin temperature which occurs as morphine-addicted rats are acutely withdrawn from the drug using naloxone (Merchenthaler, et al., Maturitas 30: 307-16 (1998)). It can also be used to detect estrogen receptor antagonist activity by co-dosing test compound with the reference estrogen.

Evaluation of Vasomotor Function in Isolated Rat Aortic Rings

Sprague-Dawley rats (240-260 grams) are divided into 4 groups:
1. Normal non-ovariectomized (intact)
2. Ovariectomized (ovex) vehicle treated
3. Ovariectomized 17β-estradiol treated (1 mg/kg/day)
4. Ovariectomized animals treated with test compound (various doses).

Animals are ovariectomized approximately 3 weeks prior to treatment. Each animal receives either 17-β estradiol sulfate (1 mg/kg/day) or test compound suspended in distilled, deionized water with 1% tween-80 by gastric gavage. Vehicle treated animals received an appropriate volume of the vehicle used in the drug treated groups.

Animals are euthanized by $CO_2$ inhalation and exsanguination. Thoracic aortae are rapidly removed and placed in 37° C. physiological solution with the following composition (mM): NaCl (54.7), KCl (5.0), $NaHCO_3$ (25.0), $MgCl_2$ $2H_2O$ (2.5), D-glucose (11.8) and $CaCl_2$ (0.2) gassed with $CO_2$—$O_2$, 95%/5% for a final pH of 7.4. The advantitia is removed from the outer surface and the vessel is cut into 2-3 mm wide rings. Rings are suspended in a 10 mL tissue bath with one end attached to the bottom of the bath and the other to a force transducer. A resting tension of 1 gram is placed on the rings. Rings are equilibrated for 1 hour, signals are acquired and analyzed.

After equilibration, the rings are exposed to increasing concentrations of phenylephrine ($10^{-8}$ to $10^{-4}$M) and the tension recorded. Baths are then rinsed 3 times with fresh buffer. After washout, 200 mM L-NAME is added to the tissue bath and equilibrated for 30 minutes. The phenylephrine concentration response curve is then repeated.

Evaluation of Cardioprotective Activity

Apolipoprotein E-deficient C57/B1J (apo E KO) mice are obtained from Taconic Farms. All animal procedures are performed under strict compliance to IACUC guidelines. Ovariectomized female apo E KO mice, 4-7 weeks of age, are housed in shoe-box cages and were allowed free access to food and water. The animals are randomized by weight into groups (n=12-15 mice per group). The animals are dosed with test compounds or estrogen (17β-estradiol sulfate at 1 mg/kg/day) in the diet using a Precise-dosing Protocol, where the amount of diet consumed is measured weekly, and the dose adjusted accordingly, based on animal weight. The diet used is a Western-style diet (57U5) that is prepared by Purina and contains 0.50% cholesterol, 20% lard and 25 IU/KG Vitamin E. The animals are dosed/fed using this paradigm for a period of 12 weeks. Control animals are fed the Western-style diet and receive no compound. At the end of the study period, the animals are euthanized and plasma samples obtained. The hearts are perfused in situ, first with saline and then with neutral buffered 10% formalin solution.

For the determination of plasma lipids and lipoproteins, total cholesterol and triglycerides are determined using enzymatic methods with commercially available kits from Boehringer Mannheim and Wako Biochemicals, respectively and analyzed using the Boehringer Mannheim Hitachii 911 Analyzer. Separation and quantification of plasma lipoproteins were performed using FPLC size fractionation. Briefly, 50-100 mL of serum is filtered and injected into Superose 12 and Superose 6 columns connected in series and eluted at a constant flow rate with 1 mM sodium EDTA and 0.15 M NaCl. Areas of each curve representing VLDL, LDL and HDL are integrated using Waters Millennium™ software, and each lipoprotein fraction is quantified by multiplying the Total Cholesterol value by the relative percent area of each respective chromatogram peak.

For the quantification of aortic atherosclerosis, the aortas are carefully isolated and placed in formalin fixative for 48-72 hours before handling. Atherosclerotic lesions are identified using Oil Red O staining. The vessels are briefly destained, and then imaged using a Nikon SMU800 microscope fitted with a Sony 3CCD video camera system in concert with IMAQ Configuration Utility (National Instrument) as the image capturing software. The lesions are quantified en face along the aortic arch using a custom threshold utility software package (Coleman Technologies). Automated lesion assessment is performed on the vessels using the threshold function of the program, specifically on the region contained within the aortic arch from the proximal edge of the brachio-cephalic trunk to the distal edge of the left subclavian artery. Aortic atherosclerosis data are expressed as percent lesion involvement strictly within this defined luminal area.

Evaluation of Cognition Enhancement

Ovariectomized rats (n=50) are habituated to an 8-arm radial arm maze for 10-min periods on each of 5 consecutive days. Animals are water-deprived prior to habituation and testing. A 100 μL aliquot of water placed at the ends of each arm serves as reinforcement. Acquisition of a win-shift task in the radial arm maze is accomplished by allowing the animal to have access to one baited arm. After drinking, the animal exits the arm and re-enters the central compartment, where it now has access to the previously visited arm or to a novel arm. A correct response is recorded when the animal chooses to enter a novel arm. Each animal is given 5 trials per day for 3 days. After the last acquisition trial, the animals are assigned to one of the following 4 groups:

1. Negative controls: injected with 10% DMSO/sesame oil vehicle once daily for 6 days (1 mL/kg, SC)
2. Positive controls: injected with 17β-estradiol benzoate for 2 days and tested 4 days after the second injection (17β-estradiol benzoate at 10 μg/0.1 mL per rat)
3. Estradiol: 17β-estradiol will be injected daily for 6 days (20 μg/kg, SC)
4. Test compound: injected daily for 6 days (doses vary).

All injections will begin after testing on the last day of acquisition. The last injection for groups 1, 3, and 4 will take place 2 hours before testing for working memory.

The test for working memory is a delayed non-matching-to-sample task (DNMS) utilizing delays of 15, 30, or 60 seconds. This task is a variation of the acquisition task in which the rat is placed in the central arena and allowed to enter one arm as before. A second arm is opened once the rat traverses halfway down the first arm, and again the rat is required to choose this arm. When it has traveled halfway down this second arm, both doors are closed and the delay is instituted. Once the delay has expired, both of the original two doors, and a third novel door, are opened simultaneously. A correct response is recorded when the animal travels halfway down the third, novel arm. An incorrect response is recorded when the animal travels halfway down either the first or second arms. Each animal will receive 5 trials at each of the three delay intervals for a total of 15 trials per subject.

Evaluation of Effect on Pleurisy

The ability to reduce the symptoms of experimentally-induced pleurisy in rats can be evaluated according to the procedure of Cuzzocrea (Endocrinology 141: 1455-63 (2000)).

Evaluation of Protection Against Glutamate-Induced Cytotoxicity (Neuroprotection)

The neuroprotective activity of compounds of this invention can be evaluated in an in vitro standard pharmacological test procedure using glutamate challenge (Zaulyanov, et al., Cellular & Molecular Neurobiology 19: 705-18 (1999); Prokai, et al., Journal of Medicinal Chemistry 44: 110-4 (2001)).

Evaluation in the Mammary End Bud Test Procedure

Estrogens are required for full ductal elongation and branching of the mammary ducts, and the subsequent development of lobulo-alveolar end buds under the influence of progesterone. In this test procedure, the mammotrophic activity of selected compounds of the invention can be evaluated according to the following standard pharmacological test procedure. Twenty-eight day old Sprague-Dawley rats (Taconic Farms, Germantown, N.Y.) are ovariectomized and rested for nine days. Animals are housed under a 12-hour light/dark cycle, fed a casein-based Purina Laboratory Rodent Diet 5K96 (Purina, Richmond, Ind.) and allowed free access to water. Rats were then dosed subcutaneously for six days with vehicle (50% DMSO (JT Baker, Phillipsburg, N.J.)/50% 1× Dulbecco's Phosphate buffered saline (GibcoBRL, Grand Island, N.Y.), 17β-estradiol (0.1 mg/kg) or test compound (20 mg/kg). For the final three days, rats are also dosed subcutaneously with progesterone (30 mg/kg). On the seventh day, rats are euthanised and a mammary fat pad excised. This fat pad is analyzed for casein kinase II mRNA as a marker of end bud proliferation. Casein kinase II mRNA is analyzed by real-time RT-PCR. Briefly, RNA is isolated following Trizol (GibcoBRL, Grand Island, N.Y.) according to the manufacture's directions, Samples are treated with DNAse I using DNA-free kit (Ambion), and casein kinase II mRNA levels are measured by real-time RT-PCR using the Taqman Gold procedure (PE Applied Biosystems). A total of 50 ng of RNA is analyzed in triplicate using casein kinase II specific primer pair (5' primer, CACACGGATGGCGCATACT (SEQ ID NO. 1); 3' primer, CTCGGGATGCACCATGAAG (SEQ ID NO. 2)) and customized probe (TAMRA-CGGCACTGGTTTC-CCTCACATGCT-FAM (SEQ ID NO. 3)). Casein kinase II mRNA levels are normalized to 18s ribosomal RNA contained within each sample reaction using primers and probe supplied by PE Applied Biosystems.

Evaluation in the HLA Rat Standard Pharmacological Test Procedure for Inflammatory Bowel Disease Representative compounds can be evaluated in the HLA rat standard pharmacological test procedure which emulates inflammatory bowel disease in humans. The following briefly describes the procedure used and results obtained. Male HLA-B27 rats are obtained from Taconic and provided unrestricted access to food (PMI Lab diet 5001) and water. Rats are dosed subcutaneously once per day with either vehicle (50% DMSO/50% 1× Dulbecco's Phosphate Buffered Saline) or test compound (0.1 to 10 mg/kg) for at least one week. Stool quality is observed daily and graded according to the following scale: Diarrhea=3; soft stool=2; normal stool=1. At the end of the study, serum is collected and stored at −70° C. A section of colon is prepared for histological analysis and an additional segment is analyzed for myeloperoxidase activity.

For histological analysis, colonic tissue is immersed in 10% neutral buffered formalin. Each specimen of colon is separated into four samples for evaluation. The formalin-fixed tissues are processed in a Tissue Tek vacuum infiltration processor (Miles, Inc; West Haven, Conn.) for paraffin embedding. The samples are sectioned at 5 μm and then stained with hematoxylin and eosin (H&E) for blinded histologic evaluations using a scale modified after Boughton-Smith. After the scores are completed the samples are unblinded, and data are tabulated and analyzed by ANOVA linear modeling with multiple mean comparisons. Sections of colonic tissue are evaluated for several disease indicators and given relative scores.

Evaluation in Three Models of Arthritis

Lewis rat assay of adjuvant-induced arthritis. Sixty, female, 12 weeks old, Lewis rats are housed according to standard facility operating procedures. They receive a standard regimen of food and water ad libitum. Each animal is identified by a cage card indicating the project group and animal number. Each rat number is marked by indelible ink marker on the tail. At least 10-21 days before study they are anesthetized and ovariectomized by standard aseptic surgical techniques.

Freund's Adjuvant-Complete (Sigma Immuno Chemicals, St. Louis, Mo.) is used to induce arthritis, each mL containing 1 mg *Mycobacterium tuberculosis* heat killed and dried, 0.85 mL mineral oil and 0.15 mL mannide monooleate Lot No. 084H8800.

The following are examples of two test procedures. Inhibition test procedure: Thirty rats are injected intradermally with 0.1 mL of Freund's Adjuvant-Complete at the base of the tail. The animals are randomized to four groups, each group containing six rats. Each day, the groups receive vehicle (50% DMSO (JT Baker, Phillipsburg, N.J.)/1× Dulbecco's phosphate saline (GibcoBRL, Grand Island, N.Y.)) or test compound (0.1-10 mg/kg, administered subcutaneously). All rats begin treatment on Day 1.

Treatment test procedure: Thirty rats are injected intradermally with 0.1 mL of Freund's Adjuvant-Complete at the base of the tail. The animals are randomized to four groups, each group containing six rats. Each day, the groups receive vehicle (50% DMSO (JT Baker, Phillipsburg, N.J.)/1× Dulbecco's phosphate saline (GibcoBRL, Grand Island, N.Y.)) or test compound (0.1-10 mg/kg, administered subcutaneously). All rats begin treatment on Day 8 after adjuvant injection.

Statistical analysis is performed using Abacus Concepts SuperANOVA. (Abacus Concepts, Inc., Berkeley, Calif.). All of the parameters of interest are subjected to Analysis of Variance with Duncan's new multiple range post hoc testing between groups. Data are expressed throughout as mean ± standard deviation (SD), and differences are deemed significant if $p<0.05$.

The degree of arthritis severity is monitored daily in terms of the following disease indices: Hindpaw erythema, hindpaw swelling, tenderness of the joints, and movements and posture. An integer scale of 0 to 3 is used to quantify the level of erythema (0=normal paw, 1=mild erythema, 2=moderate erythema, 3=severe erythema) and swelling (0=normal paw, 1=mild swelling, 2=moderate swelling, 3=severe swelling of the hind paw). The maximal score per day is 12.

At the end of the study the rats are euthanized with $CO_2$, hindlimbs removed at necropsy and fixed in 10% buffered formalin, and the tarsal joints decalcified and embedded in paraffin. Histologic sections are stained with Hematoxylin and Eosin or Saffranin O-Fast Green stain.

Slides are coded so that the examiner is blinded to the treatment groups. Synovial tissue from tarsal joints is evaluated based on synovial hyperplasia, inflammatory cell infiltration, and pannus formation (Poole and Coombs, International Archives of Allergy & Applied Immunology 54: 97-113 (1977)) as outlined below.

| Category | Grade |
| --- | --- |
| 1. Synovial lining cells | |
| a. No change | 0 |
| b. Cells enlarged, slightly thickened | 1 |
| c. Cells enlarged, increase in numbers, moderately thickened. No villus present | 2 |
| d. Cells enlarged, thickened. Villlus present | 3 |
| 2. Fibroplasia | |
| a. No change | 0 |
| b. Fibroplasia present under lining cells | 1 |
| c. Small areas of areolar tissue replaced by fibrous tissue | 2 |
| d. Replacement of areolar tissue by fibrous tissue | 3 |
| 3. Inflammatory cells | |
| a. Occasionally seen, scattered throughout selection | 0 |
| b. Cells present in small numbers in or just under lining cell layer and/or around blood vessels. | 1 |
| c. Small focal collection of cells may be present | 2 |
| d. Large numbers of cells present in capsule and in or under lining cell layers. Large foci often seen. | 3 |
| 4. Pannus | |
| a. Not detectable | 0 |
| b. Detectable | 1 |

In addition, articular cartilage and bone is evaluated using Mankin's histological grading system (Mankin, et al., Journal of Bone & Joint Surgery—American Volume 53: 523-37 (1971)) as shown below.

| Category | Grade |
| --- | --- |
| 1. Structure | |
| a. Normal | 0 |
| b. Surface irregularity | 1 |
| c. Pannus and surface irregularity | 2 |
| d. Clefts to transitional zone | 3 |
| e. Clefts to radial zone | 4 |
| f. Clefts to calcified zone | 5 |
| g. Complete disorganization | 6 |
| 2. Cells | |
| a. Normal | 0 |
| b. Diffuse hypercellularity | 1 |
| c. Cloning | 2 |
| d. Hypocellularity | 3 |
| 3. Safranin-O staining | |
| a. Normal | 0 |
| b. Slight reduction | 1 |
| c. Modest reduction | 2 |
| d. Severe reduction | 3 |
| e. No dye noted | 4 |
| 4. Tidemark integrity | |
| a. Intact | 0 |
| b. Crossed by blood vessels | 1 |

Evaluation in the HLA-B27 Rat Model of Arthritis.

Representative compounds are evaluated in the HLA-B27 rat standard pharmacological test procedure which emulates arthritis in humans. The following briefly describes the procedure used. Male HLA-B27 rats are obtained from Taconic and provided unrestricted access to a food (PMI Lab diet 5001) and water. Rats are dosed subcutaneously once per day with either vehicle (50% DMSO/50% 1× Dulbecco's Phosphate Buffered Saline) or test compound (0.1 to 10 mg/kg) for at least one week. Joint scores and histology are evaluated as described above for the Lewis rat model of adjuvant-induced arthritis.

Evaluation in the Collagen Induced Arthritis Models.

Compounds are evaluated in BALB/c mice, 6-8 weeks of age, in which arthritis is induced by monoclonal antibodies raised against type II collagen, plus lipopolysaccharide (LPS). The animals are administered intravenously with a combination of 4 different mAbs totaling 4 mg/mouse on day 0, and followed by intravenous 25 µg of LPS 72 hours later (day 3). From day 3, one hour after LPS application, tested compounds are give orally once daily for 15 days. For each animal, increase in volume of both hind paws is measured using a plethysmometer with water cell (12 mm diameter) on days 0, 5, 7, 10, 14 and 17. Percent inhibition of increase in volume is calculated.

Evaluation in vivo Models of Carcinogeneisis

The ability of compounds of this invention to treat and inhibit various malignancies or hyperprolific disorders can be evaluated in standard pharmacological test procedures that are readily available in the literature, and include the following two procedures.

Breast cancer. Athymic nu/nu (nude) mice are obtained ovariectomized from Charles River Laboratories (Wilmington, Mass.). One day prior to tumor cell injection, animals are implanted with time-release pellets containing 0.36-1.7 mg 17β-estradiol (60 or 90 day release, Innovative Research of America, Sarasota, Fla.) or a placebo. The pellet is introduced subcutaneously into the intrascapular region using a 10-gauge precision trochar. Subsequently, mice are injected subcutaneously into the breast tissue with either $1 \times 10^7$ MCF-7 cells or $1 \times 10^7$ BG-1 cells. The cells are mixed with an equal volume of matrigel, a basement membrane matrix preparation to enhance tumor establishment. Test compounds can be evaluated either by dosing one day after tumor cell implantation (inhibition regimen) or after tumors have reached a certain size (treatment regimen). Compounds are administered either intraperitoneally or orally in a vehicle of 1% tween-80 in saline each day. Tumor size is evaluated every three or seven days.

Colon cancer. The ability to treat or inhibit colon cancer can be evaluated in the test procedure of Smirnoff (Oncology Research 11: 255-64 (1999)).

Evaluation of Neuroprotection in Two in vivo Test Procedures

Transient global ischemia in the Mongolian gerbil. The effect of test compounds on preventing or treating brain injury in response to oxygen deprivation/reperfusion can be measured using the following test procedure.

Female Mongolian gerbils (60-80 g; Charles River Laboratories, Kingston, N.Y.) are housed in the Wyeth-Ayerst animal care facility (AAALAC certified) with a 12-hour light, 12-hour dark photoperiod and free access to tap water and a low-estrogen casein diet (Purina; Richmond, Ind.). After acclimation (3-5 days), gerbils are anesthetized with isoflurane (2-3% mixture with $O_2$), ovariectomized (Day 0). Beginning the following morning (Day 1), gerbils are treated subcutaneously each day with either vehicle (10% ETOH/corn oil), 17β-estradiol (1 mg/kg) or an experimental compound (0.1-20 mg/kg). On Day 6, gerbils (n=4-5/group) are anesthetized with isoflurane, the common carotid arteries visualized via a mid-line neck incision and both arteries simultaneously occluded for 5 minutes with non-traumatic micro aneurysm clips. After occlusion, the clips are removed to allow cerebral reperfusion and the neck incision closed with wound clips. All animals are fasted overnight prior to the global ischemia surgery, a step that facilitates consistent ischemic injury. On Day 12, gerbils are exposed to a lethal dose of $CO_2$, and the brains frozen on dry ice and stored at $-80°$ C.

The degree of neuronal protection is evaluated by in situ hybridization analysis of neurogranin mRNA. Briefly, 20 µm coronal cryostat sections are collected on gelatin-coated slides, dried and stored at $-80°$ C. At the time of processing, the desiccated slide boxes are warmed to room temperature, the slides postfixed in 4% paraformaldehyde, treated with acetic anhydride and then delipidated and dehydrated with chloroform and ethanol. Processed section-mounted slides are then hybridized with 200 µl ($6 \times 10^6$ DPM/slide) of an antisense or sense (control) riboprobe for Neurogranin ($^{35}$S-UTP-labeled NG-241; bases 99-340). in a 50% formamide hybridization mix and incubated overnight at $55°$ C. in a humidified slide chamber without coverslipping. The following morning, the slides are collected in racks, immersed in 2×SSC (0.3 M NaCl, 0.03 M sodium citrate; pH 7.0)/10 mM DTT, treated with RNase A (20 µg/ml) and washed (2×30 min) at $67°$ C. in 0.1×SSC to remove nonspecific label. After dehydration, the slides are opposed to BioMax (BMR-1; Kodak) X-ray film overnight.

The level of neurogranin hybridization signal is used to quantitatively assess the degree of neuronal loss in the CA1 region after injury and to evaluate the efficacy of 17β-estradiol and experimental compounds. Neurogranin mRNA is selected for these studies because it is highly expressed in the hippocampal neurons including CA1, but absent in glia and other cell types present in this brain region. Therefore, measurement of the amount of neurogranin mRNA present represents surviving neurons. Relative optical density measurements of neurogranin hybridization signal are obtained from film autoradiograms with a computer based image analysis system (C-Imaging Inc., Pittsburgh, Pa.). The results from 6 sections (40 µm apart) per animal are averaged and statistically evaluated. Numerical values are reported as the mean ±SEM. One-way analysis of variance is used to test for differences in the level of neurogranin mRNA and all statements of non-difference in the results section imply that $p>0.05$.

Middle cerebral artery occlusion in mice. Neuroprotection can be evaluated according to the test procedures described by Dubal (see, Dubal, et al., Proceedings of the National Academy of Sciences of the United States of America 98: 1952-1957 (2001), Dubal, et al., Journal of Neuroscience 19: 6385-6393 (1999)).

Ovulation Inhibition Standard Pharmacological Test Procedure

The test procedure is used to determine whether test compounds can inhibit or change the timing of ovulation. It can also be used to determine the number of oocytes ovulated [Lundeen, et al., J Steroid Biochem Mol Biol 78: 137-143 (2001)].

Transplantation Rejection

To test the ability of the test compounds to prevent transplant rejection. Compounds can be tested in animal models of heart transplantation (Stetson et al. Circulation 104:676-682 (2001) or transplant atherosclerosis (Deitrich et al. Arterioscler. Thromb. Vasc Biol. 20:343-352 (2000), Lou et al., Circulation 94:3355-3361 (1996).

Prevention of Restenosis

The test procedure is used to determine whether test compounds can inhibit vascular smooth muscle cell proliferation after carotid artery injury similar to what occurs after balloon angioplasty. The test compounds can be tested in animal models previously described (Karas et al. Circ Res. 89:534-539 (2001), Cerek et al. Atherosclerosis 131:59-66 (1997).

Treatment of Myocardial Infarction

Test compounds can be tested in animal models of ischemia/reperfusion to determine whether they would inhibit cell death occurring during a myocardial infarction. The compounds can be tested in models described previously (Delyani et al. J Mol & Cell Cardiology 28:1001-1008 (1996), Izumi et al. J Clin Invest. 108:203-213 (2001) & Chandrasekar et al. Circulation 103:2296-2302 (2001)).

Treatment for Myocarditis and Congestive Heart Failure

Test compounds can be tested in models of heart failure to determine whether compounds could be an effective therapy and improve cardiac function. Compounds can be tested in animals as described previously (Yokoseki et al. Circ Res. 89:1-9 (2001), Wallen et al. Hypertension 36:774-779 (2000) & Toshiaki et al. Circulation 104:1094-1103 (2001)).

Treatment for Diabetes

Test compounds can be tested in models of diabetes to determine their effect on reversal of obesity and diet-induced insulin resistance. Compounds can be tested in animal models as previously described (Yuan et al. Science 293:1673-1677 (2001).

Treatment for Asthma

Pulmonary Inflammation Model Mice are sensitized with OVA emulsified in alum on days 0 and 14 (ip injection). On days 28 and 29, mice are challenged with an aerosol of OVA for 20 min (1%-5% OVA) and then on Day 30 the animals are sacrificed and harvest BAL and/or lung tissue for analysis of pulmonary inflammation.

Airway Hyperresponsiveness. This model is similar to that described above however animals are challenged on 3 consecutive days with an aerosol of OVA and airway hyperresponsiveness is measured 48 h after the last challenge. BAL can also be taken at this stage if required.

To look more directly at the effects of mast cells in conjunction with ER, a passive cutaneous anaphylaxis model in which IgE is injected into the ear and then 24 hours later DNP-HSA iv is injected DNP-HSA iv can be used. Ear thickness and an early and late phase reaction are measured. Tissues are fixed in K2. embedded in Epoxy resin and cut into 1 μum sections. These can be stained for mast cells and the degree of mast cell degranulation can be quantified.

What is claimed is:

1. A compound of Formula 1:

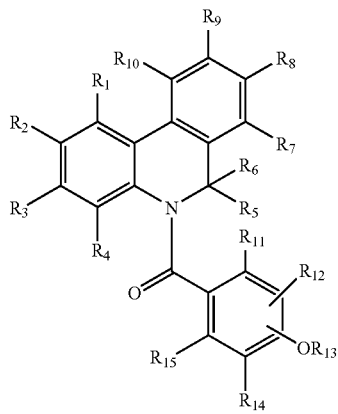

Formula 1 or a pharmaceutically acceptable salt or ester form thereof, wherein:

$R_1$, $R_2$, $R_3$, and $R_4$, are, independently, hydrogen, lower alkyl, halogen, or aryl;

$R_7$, $R_8$, $R_9$, and $R_{10}$, are, independently, hydrogen, lower alkyl or halogen;

$R_{11}$, $R_{12}$, $R_{14}$, and $R_{15}$ are, independently, hydrogen, hydroxy, lower alkyl, alkoxy, or halogen;

$R_5$ and $R_6$ are, independently, hydrogen or lower alkyl; wherein when $R_5$ is hydrogen, $R_6$ is lower alkyl, and when $R_6$ is hydrogen $R_5$ is lower alkyl;

$R_{13}$ is hydrogen, —(C=O)$R_{16}$, —S(O)$_2R_{17}$, —S(O)$_2$N($R_{18}$)($R_{19}$), or D-glucuronidate;

$R_{16}$ is alkyl or aralkyl;

$R_{17}$ is alkyl, cycloalkyl, alkenyl, cycloalkenyl, or alkynyl; and $R_{18}$ and $R_{19}$ are, independently, hydrogen, alkyl, alkenyl, alkynyl, cycloalkyl, monofluoroalkyl, perfluoroalkyl, cycloalkenyl, hydroxy-($C_2$-$C_6$)alkyl, alkoxyalkyl, alkylthioalkyl, carbonyl, acyl, alkoxycarbonyl, —C(O)NH$_2$, alkylaminocarbonyl, dialkylaminocarbonyl, alkylaminoalkyl, or dialkylaminoalkyl.

2. A compound of claim 1 having Formula 2 or Formula 3:

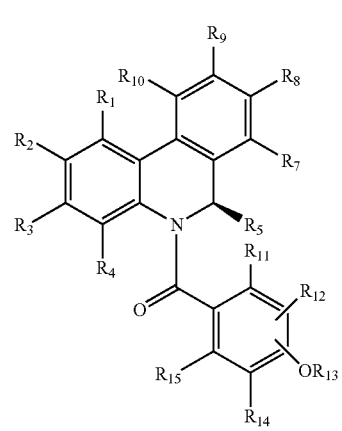

Formula 2

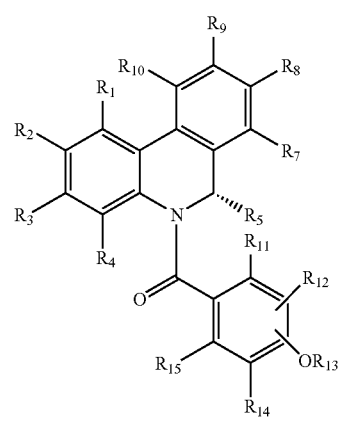

Formula 3 or a pharmaceutically acceptable salt or ester form thereof.

3. A compound of claim 1 having Formula 4:

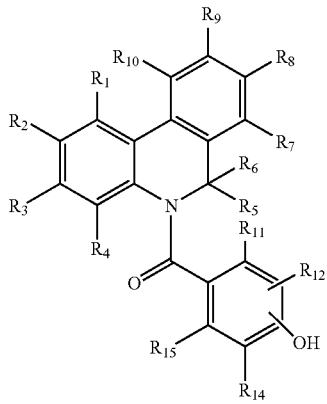

Formula 4 or a pharmaceutically acceptable salt or ester form thereof.

4. A compound of claim 3 having Formula 5 or 6:

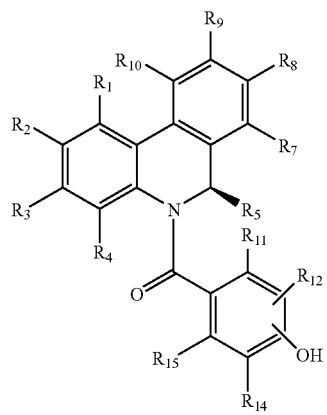

Formula 5

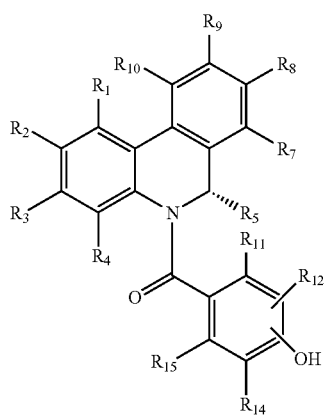

Formula 6 or a pharmaceutically acceptable salt or ester form thereof.

5. A compound of claim 1 having Formula 7:

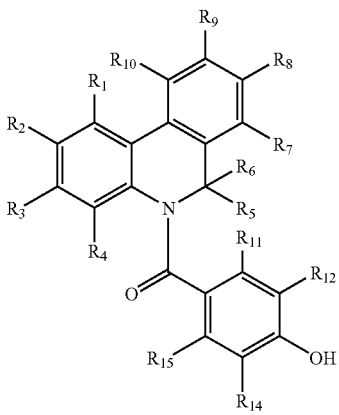

Formula 7 or a pharmaceutically acceptable salt or ester form thereof.

6. A compound of claim 5 having Formula 8 or 9:

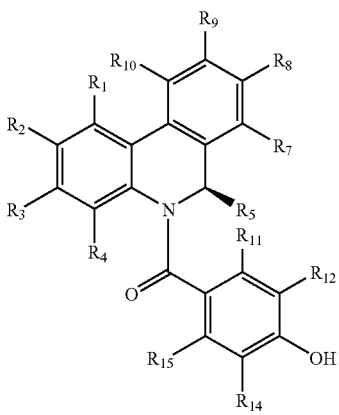

Formula 8

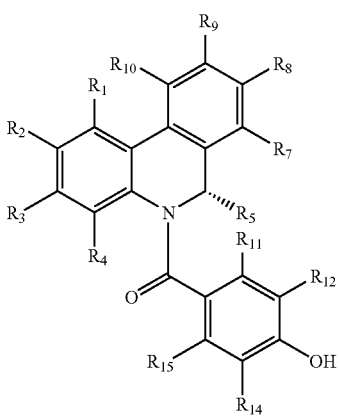

Formula 9 or a pharmaceutically acceptable salt or ester form thereof.

7. A compound of claim 1 having formula 10:

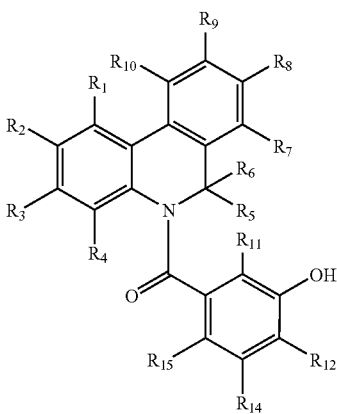

Formula 10 or a pharmaceutically acceptable salt or ester form thereof.

8. A compound of claim 7 having Formula 11 or 12:

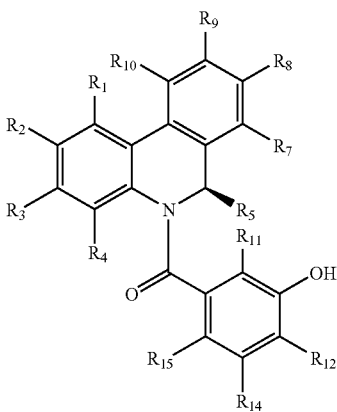

Formula 11

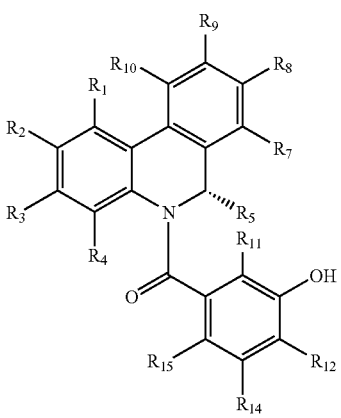

Formula 12 or a pharmaceutically acceptable salt or ester form thereof.

9. A compound of claim 1 wherein at least one of $R_1$, $R_2$, $R_3$, $R_4$, $R_7$, $R_8$, $R_9$, and $R_{10}$ is halogen.

10. A compound of claim 9 wherein $R_1$, $R_2$, $R_3$, $R_4$, $R_7$, $R_8$, $R_9$, and $R_{10}$ are, independently, hydrogen or halogen.

11. A compound of claim 10 wherein at least one of $R_3$ or $R_8$ is halogen.

12. A compound of claim 10 wherein $R_3$ and $R_8$ are halogen.

13. A compound of claim 10 wherein $R_3$ or $R_8$ is chlorine or fluorine.

14. A compound of claim 1 wherein $R_{11}$, $R_{12}$, $R_{14}$, and $R_{15}$ are, independently, hydrogen, halogen, hydroxy, or alkoxy.

15. A compound of claim 14 wherein $R_{11}$, $R_{12}$, $R_{14}$, and $R_{15}$ are, independently, hydrogen, chlorine, bromine, fluorine, hydroxy, or methoxy.

16. A compound of claim 1 wherein at least one of $R_1$, $R_2$, $R_3$, $R_4$, $R_7$, $R_8$, $R_9$, and $R_{10}$ is halogen; $R_{11}$, $R_{12}$, $R_{14}$, and $R_{15}$ are, independently, hydrogen, chlorine, bromine, fluorine, hydroxy, or methoxy; and $R_{13}$ is hydrogen.

17. A compound of claim 1 that is 4-{[(6R)-8-fluoro-6-methylphenanthridin-5(6H)-yl]carbonyl}phenol; 3-{[(6S)-8-fluoro-6-methylphenanthridin-5(6H)-yl]carbonyl}phenol; 4-{[(6S)-8-fluoro-6-methylphenanthridin-5(6H)-yl]carbonyl}phenol; 3-{[(6R)-8-fluoro-6-methylphenanthridin-5(6H)-yl]carbonyl}phenol; 3-fluoro-4-{[(6R)-8-fluoro-6-methylphenanthridin-5(6H)-yl]carbonyl}phenol; or 3-fluoro-4-{[(6S)-8-fluoro-6-methylphenanthridin-5(6H)-yl]carbonyl}phenol, or a pharmaceutically acceptable salt, or ester thereof.

18. A compound of claim 1 that is 4-fluoro-3-{[(6R)-8-fluoro-6-methylphenanthridin-5(6H)-yl]carbonyl}phenol; 4-fluoro-3-{[(6S)-8-fluoro-6-methylphenanthridin-5(6H)-yl]carbonyl}phenol; 2-fluoro-4-{[(6R)-8-fluoro-6-methylphenanthridin-5(6H)-yl]carbonyl}phenol; 2-fluoro-4-{[(6S)-8-fluoro-6-methylphenanthridin-5(6H)-yl]carbonyl}phenol; or 2-chloro-5-{[(6R)-8-fluoro-6-methylphenanthridin-5(6H)-yl]carbonyl}phenol, or a pharmaceutically acceptable salt, or ester thereof.

19. A compound of claim 1 that is 2-chloro-5-{[(6S)-8-fluoro-6-methylphenanthridin-5(6H)-yl]carbonyl}phenol; 2-bromo-4-{[(6R)-8-fluoro-6-methylphenanthridin-5(6H)-yl]carbonyl}phenol; 2-bromo-4-{[(6S)-8-fluoro-6-methylphenanthridin-5(6H)-yl]carbonyl}phenol; 4-bromo-3-{[(6R)-8-fluoro-6-methylphenanthridin-5(6H)-yl]carbonyl}phenol; or 4-bromo-3-{[(6S)-8-fluoro-6-methylphenanthridin-5(6H)-yl]carbonyl}phenol, or a pharmaceutically acceptable salt, or ester thereof.

20. A compound of claim 1 that is 4-{[(6R)-8-fluoro-6-methylphenanthridin-5(6H)-yl]carbonyl}-2-methoxyphenol; 4-{[(6S)-8-fluoro-6-methylphenanthridin-5(6H)-yl]carbonyl}-2-methoxyphenol; 4-{[(6S)-6-ethyl-8-fluorophenanthridin-5(6H)-yl]carbonyl}phenol; 4-{[(6R)-6-ethyl-8-fluorophenanthridin-5(6H)-yl]carbonyl}phenol; or 3-{[(6R)-6-ethyl-8-fluorophenanthridin-5(6H)-yl]carbonyl}phenol, or a pharmaceutically acceptable salt, or ester thereof.

21. A compound of claim 1 that is 4-{[(6R)-6-ethyl-8-fluorophenanthridin-5(6H)-yl]carbonyl}benzene-1,3-diol; 4-[(6-ethyl-8-fluorophenanthridin-5(6H)-yl) carbonyl]-3-fluorophenol; 3-[(3-chloro-6-methylphenanthridin-5(6H)-yl)carbonyl]phenol; 3-{[(6R)-3-chloro-6-methylphenanthridin-5(6H)-yl]carbonyl}phenol; or 3-{[(6S)-3-chloro-6-methylphenanthridin-5(6H)-yl]carbonyl}phenol, or a pharmaceutically acceptable salt, or ester thereof.

22. A compound of claim 1 that is 4-[(3-chloro-6-methylphenanthridin-5(6H)-yl)carbonyl]phenol; 4-{[(6R)-3-chloro-6-methylphenanthridin-5(6H)-yl]carbonyl}phenol; 4-{[(6S)-3-chloro-6-methylphenanthridin-5(6H)-yl]carbonyl}phenol; 4-[3-chloro-6-methylphenanthridin-5(6H)-yl]carbonyl]benzene-1,3-diol; or 4-{[(6R)-3-chloro-6-methylphenanthridin-5(6H)-yl]carbonyl}benzene-1,3-diol, or a pharmaceutically acceptable salt, or ester thereof.

23. A compound of claim 1 that is 4-{[(6S)-3-chloro-6-methylphenanthridin-5(6H)-yl]carbonyl}benzene-1,3-diol; 3-[(3-fluoro-6-methylphenanthridin-5(6H)-yl)carbonyl]

phenol; 3-{[(6R)-3-fluoro-6-methylphenanthridin-5(6H)-yl]carbonyl}phenol; 3-{[(6S)-3-fluoro-6-methylphenanthridin-5(6H)-yl]carbonyl}phenol; or 4-[(3-fluoro-6-methylphenanthridin-5(6H)-yl)carbonyl]phenol, or a pharmaceutically acceptable salt, or ester thereof.

24. A compound of claim 1 that is 4-{[(6R)-3-fluoro-6-methylphenanthridin-5(6H)-yl]carbonyl}phenol; 4-{[(6S)-3-fluoro-6-methylphenanthridin-5(6H)-yl]carbonyl}phenol; 4-[(3-fluoro-6-methylphenanthridin-5(6H)-yl)carbonyl]benzene-1,3-diol; 4-{[(6R)-3-fluoro-6-methylphenanthridin-5(6H)-yl]carbonyl}benzene-1,3-diol; or 4-{[(6S)-3-fluoro-6-methylphenanthridin-5(6H)-yl]carbonyl}benzene-1,3-diol, or a pharmaceutically acceptable salt, or ester thereof.

25. A compound of claim 1 that is 4-[(3,8-difluoro-6-methylphenanthridin-5(6H)-yl)carbonyl]phenol; 4-{[(6R)-3,8-Difluoro-6-methylphenanthridin-5(6H)-yl]carbonyl}phenol; or 4-{[(6S)-3,8-Difluoro-6-methylphenanthridin-5(6H)-yl]carbonyl}phenol, or a pharmaceutically acceptable salt, or ester thereof.

26. A compound of claim 1 that is 4-[(3,8-difluoro-6-methylphenanthridin-5(6H)-yl)carbonyl]phenol; 4-{[(6R)-3,8-Difluoro-6-methylphenanthridin-5(6H)-yl]carbonyl}phenol; 4-{[(6S)-3,8-Difluoro-6-methylphenanthridin-5(6H)-yl]carbonyl}phenol; or 4-{[(6R)-3,8-difluoro-6-methylphenanthridin-5(6H)-yl]carbonyl}-2-fluorophenol, or a pharmaceutically acceptable salt, ester, or solvate form thereof.

27. A composition comprising a compound of claim 1 or a pharmaceutically acceptable salt thereof, and a pharmaceutically acceptable carrier.

\* \* \* \* \*

UNITED STATES PATENT AND TRADEMARK OFFICE
CERTIFICATE OF CORRECTION

PATENT NO. : 7,585,871 B2 Page 1 of 1
APPLICATION NO. : 11/215333
DATED : September 8, 2009
INVENTOR(S) : Steffan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 949 days.

Signed and Sealed this

Fourteenth Day of September, 2010

David J. Kappos
*Director of the United States Patent and Trademark Office*